United States Patent
Kwon et al.

(10) Patent No.: US 10,626,183 B2
(45) Date of Patent: Apr. 21, 2020

(54) IFN-γ-INDUCIBLE REGULATORY T CELL CONVERTIBLE ANTI-CANCER (IRTCA) ANTIBODY AND USES THEREOF

(71) Applicant: Eutilex Co., Ltd., Seoul (KR)

(72) Inventors: Byoung S Kwon, Gwangmyeong-si (KR); Seoung-Joo Lee, Gwangmyeong-si (KR); Joong Won Lee, Gwangmyeong-si (KR); Seunghyun Lee, Gwangmyeong-si (KR)

(73) Assignee: Eutilex Co., Ltd., Seoul (KR)

( * ) Notice: Subject to any disclaimer, the term of this patent is extended or adjusted under 35 U.S.C. 154(b) by 0 days.

(21) Appl. No.: 16/255,690

(22) Filed: Jan. 23, 2019

(65) Prior Publication Data

US 2019/0233535 A1   Aug. 1, 2019

Related U.S. Application Data

(63) Continuation of application No. PCT/IB2018/000201, filed on Feb. 9, 2018.

(60) Provisional application No. 62/457,422, filed on Feb. 10, 2017.

(51) Int. Cl.

| | |
|---|---|
| *C07K 16/30* | (2006.01) |
| *A61P 37/02* | (2006.01) |
| *A61K 38/20* | (2006.01) |
| *A61P 35/02* | (2006.01) |
| *C07K 16/28* | (2006.01) |
| *A61P 35/04* | (2006.01) |
| *G01N 33/68* | (2006.01) |
| *A61P 35/00* | (2006.01) |
| *A61K 39/00* | (2006.01) |
| *A61K 45/06* | (2006.01) |
| *G01N 33/50* | (2006.01) |
| *A61K 38/19* | (2006.01) |

(52) U.S. Cl.
CPC ............ *C07K 16/30* (2013.01); *A61K 38/193* (2013.01); *A61K 38/208* (2013.01); *A61K 45/06* (2013.01); *A61P 35/00* (2018.01); *A61P 35/02* (2018.01); *A61P 35/04* (2018.01); *A61P 37/02* (2018.01); *C07K 16/2878* (2013.01); *G01N 33/505* (2013.01); *G01N 33/5011* (2013.01); *G01N 33/6866* (2013.01); *A61K 2039/505* (2013.01); *C07K 2317/14* (2013.01); *C07K 2317/24* (2013.01); *C07K 2317/34* (2013.01); *C07K 2317/52* (2013.01); *C07K 2317/55* (2013.01); *C07K 2317/565* (2013.01); *C07K 2317/75* (2013.01); *C07K 2317/76* (2013.01); *C07K 2317/92* (2013.01); *C07K 2317/94* (2013.01); *G01N 2800/52* (2013.01)

(58) Field of Classification Search
CPC combination set(s) only.
See application file for complete search history.

(56) References Cited

U.S. PATENT DOCUMENTS

| | | | |
|---|---|---|---|
| 6,218,149 B1 | 4/2001 | Morrison et al. | |
| 6,472,511 B1 | 10/2002 | Leung | |
| 6,602,684 B1 | 8/2003 | Umana et al. | |
| 6,794,132 B2 | 9/2004 | Buechler et al. | |
| 7,812,135 B2 | 10/2010 | Smith et al. | |
| 9,255,151 B2 | 2/2016 | Kwon | |
| 9,255,152 B2 | 2/2016 | Kwon | |
| 9,309,321 B2 | 4/2016 | Kwon | |
| 2002/0028486 A1 | 3/2002 | Morrison et al. | |
| 2002/0187526 A1 | 12/2002 | Ruben et al. | |
| 2003/0091995 A1 | 5/2003 | Buechler et al. | |
| 2003/0115614 A1 | 6/2003 | Kanda et al. | |
| 2007/0098719 A1 | 5/2007 | Smith et al. | |
| 2014/0065152 A1 | 3/2014 | Kwon | |
| 2014/0072565 A1 | 3/2014 | Kwon | |
| 2014/0072566 A1 | 3/2014 | Kwon | |
| 2016/0024177 A1 | 1/2016 | Kwon | |
| 2016/0046691 A1 | 2/2016 | Kwon | |
| 2016/0244503 A1 | 8/2016 | Kwon | |
| 2018/0170997 A1 | 6/2018 | Kwon | |

FOREIGN PATENT DOCUMENTS

| | | |
|---|---|---|
| EP | 0359096 | 3/1990 |
| JP | 2008278814 | 11/2008 |
| WO | WO 2000/061739 | 10/2000 |
| WO | WO 2001/029246 | 4/2001 |
| WO | WO 2002/030954 | 4/2002 |
| WO | WO 2002/031140 | 4/2002 |

(Continued)

OTHER PUBLICATIONS

Rudikoff et al., Single amino acid substitution altering antigen-binding specificity, PNAS 79-1979-1983, 1982. (Year: 1982).*
Giusti et al., Somatic diversification of S107 from an antiphosphocholine to an anti-DNA autoantibody is due to a single base change in its heavy chain variable region. PNAS, 84, 2926-2930, 1987. (Year: 1987).*
U.S. Appl. No. 10/277,370, filed Oct. 22, 2002, Presta.
U.S. Appl. No. 10/113,929, filed Apr. 2, 2002, Reff & Davis.
Bae et al., "Glucocorticoid-induced tumour necrosis factor receptor-related protein-mediated macrophage stimulation may induce cellular adhesion and cytokine expression in rheumatoid arthritis," Clinical and Experimental Immunology, 2007, 148:410-418.

(Continued)

*Primary Examiner* — Elly-Gerald Stoica
(74) *Attorney, Agent, or Firm* — Fish & Richardson P.C.

(57) ABSTRACT

Provided are IFN-γ-Inducible Regulatory T Cell Convertible Anti-Cancer (IRTCA) antibodies and antigen-binding fragment thereof that bind to an activation-inducible TNFR (AITR) polypeptide. Various in vitro and in vivo methods and compositions related to IRTCA antibodies described herein are also provided. Methods include, for example, changing cytokine secretion from T cells in vivo or in vitro and prevention and/or therapeutic treatment of cancer using an IRTCA antibody or fragment thereof.

30 Claims, 40 Drawing Sheets

Specification includes a Sequence Listing.

(56) References Cited

FOREIGN PATENT DOCUMENTS

| WO | WO 2003/035835 | 5/2003 |
|---|---|---|
| WO | WO 2011/028683 | 3/2011 |
| WO | WO 2015/184099 A1 | 3/2015 |

OTHER PUBLICATIONS

Barbas et al, "Combinatorial lmmunoglobulin Libraries on the Surface of Phage (Phabs): Rapid Selection of Antigen-Specific Fabs," METHODS: A Companion to Methods in Enzymology, 1991, 2(2):119-124.
Basso et al., "More stories on Th17 cells," Cell Res, 2009, 4:399-411.
Chan et al, "Signaling by the TNF Receptor Superfamily and T Cell Homeostasis," Immunity, 2000, 13:419-422.
Chattopadhyay et al, "Evolution of GITRL immune function: murine GITRL exhibits unique structural and biochemical properties within the TNF superfamily," PNAS, 2008, 105(2):635-640.
Davies et al, "Expression of GnTIII in a Recombinant Anti-CD20 CHO Production Cell Line: Expression of Antibodies with Altered Glycoforms Leads to an Increase in ADCC Through Higher Affinity for FcgRIII," Biotechnol Bioeng, 2001, 74:288-294.
Dolff et al., "Disturbed Th1, Th2, Th17 and Treg balance in patients with systemic lupus ervthematosus," Clin Immunol., 2011, 141(2):197-204.
Elliott et al, "Repeated therapy with monoclonal antibody to tumour necrosis factor α (cA2) in patients with rheumatoid arthritis," Lancet, Oct. 22, 1994, 344:1125-1127.
Fawcett, J. et al., Mapping the homotypic binding sites in CD31 and the role of CD31 adhesion in the formation of interendothelial cell contacts, J Cell Biol., 128(6): 1229-1241 (1995).
Gurney, A.L., et al., Identification of a new member of the tumor necrosis factor family and its receptor, a human ortholog of mouse GITR, Current Biology, 9(4) :215-218 (1999).
Ha, H., TRAF-Mediated TNFR-Family Signaling, Curr Protoc lmmunol., Chapter II: Unit 11.9D.1-11.9D.19 (Nov. 2009).
Haabeth et al, "Inflammation driven by tumour-specific Th1 cells protects against B-cell cancer," Nat Commun, 2011, 2:240.
Hanabuchi et al., "Human plasmacytoid predendritic cells activate NK cells through glucocorticoid-induced tumor necrosis factor receptor-ligand (GITRL)," Blood, 2006, 107: 3617-3623.
Harlow et al. (Using Antibodies: a Laboratory Manual, Cold Spring Harbor Laboratory Press, 1999, p. 4).
Hermann-Kleiter & Baier, "NFAT pulls the strings during CD4+ T helper cell effector functions," Blood, 2010, 115(15):2989-2997.
Horn et al, "Selection of phage-displayed Fab antibodies on the active conformation of Ras yields a high affinity conformation-specific antibody preventing the binding of c-Raf kinase to Ras," FEBS Letters, 1999, 463:115-120.
Ikeda et al, "The roles of IFN gamma in protection against tumor development and cancer immunoeditinq," Cvtokine Growth Factor Rev., 2002, 13(2):95-109.
Kim et al., "Regulatory T Cells in the Human Immune System," Korean J Otorhinolaryngology—Head Neck Surg, 2010, 53(12):737-748.
Kwon et al, "Identification of a Novel Activation-inducible Protein of the Tumor Necrosis Factor Receptor Superfamily and Its Ligand," J Biol Chem, Mar. 5, 1999, 274:6056-6061.
Kwon, Byoung Se, The 2012 Spring Conference of The Korean Association of Immunology, English Abstract and Presentation Program presented at Seoul Kyoyuk Munhwa Hoekwar, pp. 1-5, Apr. 12-13, 2012.
Lafaille & Lafaille, "Natural and Adaptive Foxp3+ Regulatory T Cells: More of the Same or a Division of Labor?," Immunity, May 22, 2009, 30:626-635.
Lee et al, "E3 Ubiquitin Ligase VHL Regulates Hypoxia-Inducible Factor-1α to Maintain Regulatory T Cell Stability and Suppressive Capacity," Immunity, 2015, 42:1062-1074, 2015.
Liu et al, "Tumor Regulatory T Cells Potently Abrogate Antitumor Immunity," J Immunol, 2009, 182(10): 6160-6167.
Macian, "NFAT proteins: key regulators of T-cell development and function," Nat Rev lmmunol., 2005, 5(6):472-484.
Memorandum from Andrew H. Hirshfeld, Deputy Commissioner for Patent Examination Policy, United States Patent and Trademark Office, 19 pages (dated Mar. 4, 2014).
Nair & Jacob, "A simple practice guide for dose conversion between animals and human," J Basic Clin Pharm. Mar. 2016-May 2016, 7(2):27-31.
Okazaki et al, "Fucose Depletion from Human IgG1 Oligosaccharide Enhances Binding Enthalpy and Association Rate Between IgG1 and FcγRIIIa," JMB, 2004, 336:1239-1249.
Recombinant DNA, Wikipedia, pp. 1-9 (dated May 8, 2012). URL: https://web.archive.org/web/20120508143225/http://en.wikipedia.org/wiki/Recombinant DNA.
Rodriguez-Reyna et al., "Th17 peripheral cells are increased in diffuse cutaneous systemic sclerosis compared with limited illness: a cross-sectional study," Rheumatol Int., 2011, 32:2653-2660.
Sakaguchi et al, "Regulatory T Cells and Immune Tolerance," Cell, 2008, 133:775-787.
Sakaguchi, "Regulatory T Cells: Key Controllers of Immunologic Self-Tolerance," Cell, 101:455-458, 2000.
Shields et al, "Lack of Fucose on Human IgG1 N-Linked Oligosaccharide Improves Binding to Human Fc RIII and Antibody-dependent Cellular Toxicity," Jul. 26, 2002, J Biol Chem, 277:26733-26740.
Shimizu et al, "Stimulation of CD25+CD4+ regulatory T cells through GITR breaks immunological self-tolerance," Nat Immunol., Jan. 22, 2002, 3:135-142.
Shinkawa et al, "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," J Biol Chem, 2003, 278:3466-3473.
Stockinger & Veldhoen, "Differentiation and function of Th17 T cells," Curr Opin lmmunol., 2007, 19(3):281-286.
Truchetet et al, "Increased frequency of circulating Th22 in addition to Th17 and Th2 lymphocytes in systemic sclerosis: association with interstitial lung disease," Arthritis Research & Therapy, 2011, 13:R166, pp. 1-9.
Umana et al, "Engineered glycoforms of an antineuroblastoma IgG1 with optimized antibodydependent cellular cytotoxic activity," Nat. Biotechnol, Feb. 1999, 17:176-180.
United States Patent and Trademark Office Department of Commerce, "Subject Matter Eligibility Examples: Life Sciences," 2014 Interim Guidance on Subject Matter Eligibility (2014 IEG), pp. 1-31 (May 2016).
United States Patent and Trademark Office Department of Commerce, 2014 Interim Guidance on Subject Matter Eligibility (2014 IEG), pp. 1-44 (issued Dec. 16, 2014).
United States Patent and Trademark Office Department of Commerce, Evaluating subject Matter Eligibility Under 35 U.S.C. § 101, pp. 1-93 (updated Mar. 19, 2014).
Winter et al., "Making antibodies by phage display technology," Ann. Rev.lmmunol., 1994, 12: 433-455.
Zhou et al, "Foxp3 instability leads to the generation of pathogenic memory T cells in vivo," Nature immunology, Sep. 2009, 10:1000-1007.
Zhou et al, "Human glucocorticoid-induced TNF receptor ligand regulates its signaling activity through multiple oligomerization states," PNAS, Apr. 8, 2008, 105:5465-5470.
Zhu & Paul, "CD4 T cells: fates, functions, and faults," Blood, 2008, 112: 1557-1569.
Zwick et al, "Identification and Characterization of a Peptide That Specifically Binds the Human, Broadly Neutralizing Anti-Human Immunodeficiency Virus Type 1 Antibody b12," J. Viral., 2001, 75(14):6692-6699.
Search Report in EP Application No. 18751349.4 dated Jan. 28, 2020, 11 pages.

* cited by examiner a. Parental IRTCA-A Fab

QSVVTQPPSVSAAPGQKVTISCSGSGSTSNIGNNYVSWYQQLPGTAPKLLIYDNKRPSGIPDRFSGSKSGTSATLGITG
LRTIGDEADYFCGTWDSSLNAWVFGGGTKLTVL (Variable light)
RTVAAPSVFIFPPSDEQLKSGTASVVCLLNNFYPREAKVQWKVDNALQSGNSQESVTEQDSKDSTYSLSSTLTLSKAD
YEKHKVYACEVTHQGLSSPVTKSFNRGEC (Constant Kappa)-F-IIN-
EEFKMKYLLPTAAAGLLLLAAQPAMA (pel-B region)
QVQLVQSGTQVKMPGASVKVSCKASGYTFDDYGIGWVRQAPGQGLEWMGWISPYTHRTNSSPKLQDRVTMTTDTSTST
AYMELRSLRSDDTAVYYCARDGTYDFWSGYFDNGAFDIWGQGTLVTVSS (Variable heavy)
ASTKGPSVFPLAPSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTSGQAGQ (Constant heavy)
HHHHHH (6-Histidine)

b. Parental IRTCA-A Fab with stop codon

QSVVTQPPSVSAAPGQKVTISCSGSGSTSNIGNNYVSWYQQLPGTAPKLLIYDNKRPSGIPDRFSGSKSGTSATLGITG
LRTIGDEADYF*GTWDSSLNAWVFGGGTKLTVL (Variable light)
RTVAAPSVFIFPPSDEQLKSGTASVVCLLNNFYPREAKVQWKVDNALQSGNSQESVTEQDSKDSTYSLSSTLTLSKAD
YEKHKVYACEVTHQGLSSPVTKSFNRGEC (Constant Kappa)-F-IIN-
EEFKMKYLLPTAAAGLLLLAAQPAMA (pel-B region)
QVQLVQSGTQVKMPGASVKVSCKASGYTFDDYGIGWVRQAPGQGLEWMGWISPYTHRTNSSPKLQDRVTMTTDTSTST
AYMELRSLRSDDTAVYY*ARDGTYDFWSGYFDNGAFDIWGQGTLVTVSS (Variable heavy)
ASTKGPSVFPLAPSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTSGQAGQ (Constant heavy)
HHHHHH (6-Histidine)
* : stop codon

FIG. 1

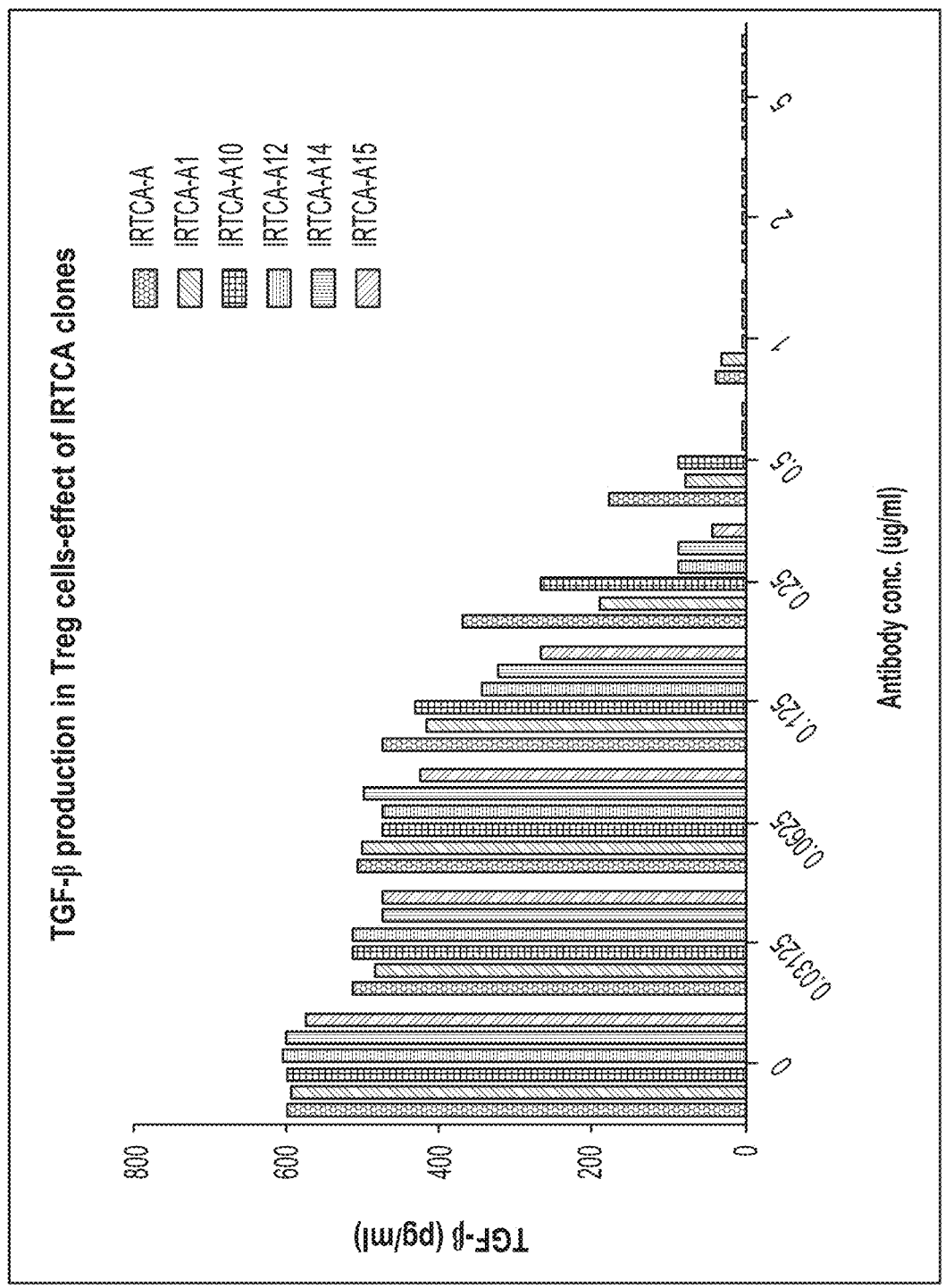

SEQUENCE LISTING

```
<160> NUMBER OF SEQ ID NOS: 32

<210> SEQ ID NO 1
<211> LENGTH: 128
<212> TYPE: PRT
<213> ORGANISM: Artificial Sequence
<220> FEATURE:
<223> OTHER INFORMATION: Chemically synthesized peptide
```

<400> SEQUENCE: 1

Gln Val Gln Leu Val Gln Ser Gly Thr Gln Val Lys Met Pro Gly Ala
1               5                   10                  15

Ser Val Lys Val Ser Cys Lys Ala Ser Gly Tyr Thr Phe Asp Asp Tyr
            20                  25                  30

Gly Ile Gly Trp Val Arg Gln Ala Pro Gly Gln Gly Leu Glu Trp Met
        35                  40                  45

Gly Trp Ile Ser Pro Tyr Thr His Arg Thr Asn Ser Ser Pro Lys Leu
50                  55                  60

Gln Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Thr Tyr Tyr Asp Phe Trp Ser Gly Tyr Phe Asp Asn
            100                 105                 110

Gly Ala Phe Asp Ile Trp Gly Gln Gly Thr Leu Val Thr Val Ser Ser
        115                 120                 125

<210> SEQ ID NO 2
<211> LENGTH: 110
<212> TYPE: PRT
<213> ORGANISM: Artificial Sequence
<220> FEATURE:
<223> OTHER INFORMATION: Chemically synthesized peptide

<400> SEQUENCE: 2

Gln Ser Val Val Thr Gln Pro Pro Ser Val Ser Ala Ala Pro Gly Gln
1               5                   10                  15

Lys Val Thr Ile Ser Cys Ser Gly Ser Thr Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Tyr Lys Arg Pro Ser Gly Ile Pro Asp Arg Phe Ser
50                  55                  60

Gly Ser Lys Ser Gly Thr Ser Ala Thr Leu Gly Ile Thr Gly Leu Arg
65                  70                  75                  80

Thr Gly Asp Glu Ala Asp Tyr Phe Cys Gly Thr Trp Asp Ser Ser Leu
                85                  90                  95

Asn Ala Trp Val Phe Gly Gly Gly Thr Lys Leu Thr Val Leu
            100                 105                 110

<210> SEQ ID NO 3
<211> LENGTH: 128
<212> TYPE: PRT
<213> ORGANISM: Artificial Sequence
<220> FEATURE:
<223> OTHER INFORMATION: Chemically synthesized peptide

<400> SEQUENCE: 3

Gln Val Gln Leu Val Gln Ser Gly Thr Gln Val Lys Met Pro Gly Ala
1               5                   10                  15

Ser Val Lys Val Ser Cys Lys Ala Ser Gly Tyr Thr Phe Asp Asp Tyr
            20                  25                  30

Gly Ile Gly Trp Val Arg Gln Ala Pro Gly Gln Gly Leu Glu Trp Met
        35                  40                  45

Gly Trp Ile Ser Pro Tyr Thr His Arg Thr Asn Ser Ser Pro Lys Leu
50                  55                  60

```
Gln Asp Arg Val Thr Met Thr Thr Asp Thr Ser Thr Ser Thr Ala Tyr
 65                  70                  75                  80

Met Glu Leu Arg Ser Leu Arg Ser Asp Thr Ala Val Tyr Tyr Cys
                 85                  90                  95

Ala Arg Asp Gly Thr Tyr Tyr Asp Phe Trp Ser Gly Tyr Phe Asp Asn
            100                 105                 110

Ala Ala Phe Asp Ser Trp Gly Gln Gly Thr Leu Val Thr Val Ser Ser
            115                 120                 125

<210> SEQ ID NO 4
<211> LENGTH: 128
<212> TYPE: PRT
<213> ORGANISM: Artificial Sequence
<220> FEATURE:
<223> OTHER INFORMATION: Chemically synthesized peptide

<400> SEQUENCE: 4

Gln Val Gln Leu Val Gln Ser Gly Thr Gln Val Lys Met Pro Gly Ala
 1               5                  10                  15

Ser Val Lys Val Ser Cys Lys Ala Ser Gly Tyr Thr Phe Asp Asp Tyr
                 20                  25                  30

Gly Ile Gly Trp Val Arg Gln Ala Pro Gly Gln Gly Leu Glu Trp Met
             35                  40                  45

Gly Trp Ile Ser Pro Tyr Thr His Arg Thr Asn Ser Ser Pro Lys Leu
 50                  55                  60

Gln Asp Arg Val Thr Met Thr Thr Asp Thr Ser Thr Ser Thr Ala Tyr
 65                  70                  75                  80

Met Glu Leu Arg Ser Leu Arg Ser Asp Thr Ala Val Tyr Tyr Cys
                 85                  90                  95

Ala Arg Asp Gly Thr Tyr Tyr Asp Phe Trp Ser Gly Tyr Phe Asp Asn
            100                 105                 110

Ala Thr Phe Asp Phe Trp Gly Gln Gly Thr Leu Val Thr Val Ser Ser
            115                 120                 125

<210> SEQ ID NO 5
<211> LENGTH: 128
<212> TYPE: PRT
<213> ORGANISM: Artificial Sequence
<220> FEATURE:
<223> OTHER INFORMATION: Chemically synthesized peptide

<400> SEQUENCE: 5

Gln Val Gln Leu Val Gln Ser Gly Thr Gln Val Lys Met Pro Gly Ala
 1               5                  10                  15

Ser Val Lys Val Ser Cys Lys Ala Ser Gly Tyr Thr Phe Asp Asp Tyr
                 20                  25                  30

Gly Ile Gly Trp Val Arg Gln Ala Pro Gly Gln Gly Leu Glu Trp Met
             35                  40                  45

Gly Trp Ile Ser Pro Tyr Thr His Arg Thr Asn Ser Ser Pro Lys Leu
 50                  55                  60

Gln Asp Arg Val Thr Met Thr Thr Asp Thr Ser Thr Ser Thr Ala Tyr
 65                  70                  75                  80

Met Glu Leu Arg Ser Leu Arg Ser Asp Thr Ala Val Tyr Tyr Cys
                 85                  90                  95

Ala Arg Asp Gly Thr Tyr Tyr Asp Phe Trp Ser Gly Tyr Phe Asp Asn
            100                 105                 110

Asn Ala Phe Asp Ile Trp Gly Gln Gly Thr Leu Val Thr Val Ser Ser
```

<210> SEQ ID NO 6
<211> LENGTH: 128
<212> TYPE: PRT
<213> ORGANISM: Artificial Sequence
<220> FEATURE:
<223> OTHER INFORMATION: Chemically synthesized peptide

<400> SEQUENCE: 6

Gln Val Gln Leu Val Gln Ser Gly Thr Gln Val Lys Met Pro Gly Ala
1               5                   10                  15

Ser Val Lys Val Ser Cys Lys Ala Ser Gly Tyr Thr Phe Asp Asp Tyr
            20                  25                  30

Gly Ile Gly Trp Val Arg Gln Ala Pro Gly Gln Gly Leu Glu Trp Met
        35                  40                  45

Gly Trp Ile Ser Pro Tyr Thr His Arg Thr Asn Ser Ser Pro Lys Leu
    50                  55                  60

Gln Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Thr Tyr Tyr Asp Phe Trp Ser Gly Tyr Phe Asp Thr
            100                 105                 110

Ala Ala Phe Asp Ile Trp Gly Gln Gly Thr Leu Val Thr Val Ser Ser
        115                 120                 125

<210> SEQ ID NO 7
<211> LENGTH: 110
<212> TYPE: PRT
<213> ORGANISM: Artificial Sequence
<220> FEATURE:
<223> OTHER INFORMATION: Chemically synthesized peptide

<400> SEQUENCE: 7

Gln Ser Val Val Thr Gln Pro Pro Ser Val Ser Ala Ala Pro Gly Gln
1               5                   10                  15

Lys Val Thr Ile Ser Cys Ser Gly Ser Thr Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Tyr Lys Arg Pro Ser Gly Ile Pro Asp Arg Phe Ser
    50                  55                  60

Gly Ser Lys Ser Gly Thr Ser Ala Thr Leu Gly Ile Thr Gly Leu Arg
65                  70                  75                  80

Thr Gly Asp Glu Ala Asp Tyr Phe Cys Gly Ser Trp Glu Ser Gly Ser
                85                  90                  95

Asn Ala Tyr Lys Phe Gly Gly Gly Thr Lys Leu Thr Val Leu
            100                 105                 110

<210> SEQ ID NO 8
<211> LENGTH: 8
<212> TYPE: PRT
<213> ORGANISM: Artificial Sequence
<220> FEATURE:
<223> OTHER INFORMATION: Chemically synthesized peptide

<400> SEQUENCE: 8

Gly Tyr Thr Phe Asp Asp Tyr Gly
1               5

<210> SEQ ID NO 9
<211> LENGTH: 8
<212> TYPE: PRT
<213> ORGANISM: Artificial Sequence
<220> FEATURE:
<223> OTHER INFORMATION: Chemically synthesized peptide

<400> SEQUENCE: 9

Ile Ser Pro Tyr Thr His Arg Thr
1               5

<210> SEQ ID NO 10
<211> LENGTH: 21
<212> TYPE: PRT
<213> ORGANISM: Artificial Sequence
<220> FEATURE:
<223> OTHER INFORMATION: Chemically synthesized peptide

<400> SEQUENCE: 10

Ala Arg Asp Gly Thr Tyr Tyr Asp Phe Trp Ser Gly Tyr Phe Asp Asn
1               5                   10                  15

Gly Ala Phe Asp Ile
            20

<210> SEQ ID NO 11
<211> LENGTH: 8
<212> TYPE: PRT
<213> ORGANISM: Artificial Sequence
<220> FEATURE:
<223> OTHER INFORMATION: Chemically synthesized peptide

<400> SEQUENCE: 11

Thr Ser Asn Ile Gly Asn Asn Tyr
1               5

<210> SEQ ID NO 12
<211> LENGTH: 3
<212> TYPE: PRT
<213> ORGANISM: Artificial Sequence
<220> FEATURE:
<223> OTHER INFORMATION: Chemically synthesized peptide

<400> SEQUENCE: 12

Asp Asn Tyr
1

<210> SEQ ID NO 13
<211> LENGTH: 11
<212> TYPE: PRT
<213> ORGANISM: Artificial Sequence
<220> FEATURE:
<223> OTHER INFORMATION: Chemically synthesized peptide

<400> SEQUENCE: 13

Gly Thr Trp Asp Ser Ser Leu Asn Ala Trp Val
1               5                   10

<210> SEQ ID NO 14
<211> LENGTH: 21
<212> TYPE: PRT
<213> ORGANISM: Artificial Sequence
<220> FEATURE:
<223> OTHER INFORMATION: Chemically synthesized peptide

<400> SEQUENCE: 14

```
Ala Arg Asp Gly Thr Tyr Tyr Asp Phe Trp Ser Gly Tyr Phe Asp Asn
1               5                   10                  15

Ala Ala Phe Asp Ser
            20

<210> SEQ ID NO 15
<211> LENGTH: 21
<212> TYPE: PRT
<213> ORGANISM: Artificial Sequence
<220> FEATURE:
<223> OTHER INFORMATION: Chemically synthesized peptide

<400> SEQUENCE: 15

Ala Arg Asp Gly Thr Tyr Tyr Asp Phe Trp Ser Gly Tyr Phe Asp Asn
1               5                   10                  15

Ala Thr Phe Asp Phe
            20

<210> SEQ ID NO 16
<211> LENGTH: 21
<212> TYPE: PRT
<213> ORGANISM: Artificial Sequence
<220> FEATURE:
<223> OTHER INFORMATION: Chemically synthesized peptide

<400> SEQUENCE: 16

Ala Arg Asp Gly Thr Tyr Tyr Asp Phe Trp Ser Gly Tyr Phe Asp Asn
1               5                   10                  15

Asn Ala Phe Asp Ile
            20

<210> SEQ ID NO 17
<211> LENGTH: 21
<212> TYPE: PRT
<213> ORGANISM: Artificial Sequence
<220> FEATURE:
<223> OTHER INFORMATION: Chemically synthesized peptide

<400> SEQUENCE: 17

Ala Arg Asp Gly Thr Tyr Tyr Asp Phe Trp Ser Gly Tyr Phe Asp Thr
1               5                   10                  15

Ala Ala Phe Asp Ile
            20

<210> SEQ ID NO 18
<211> LENGTH: 11
<212> TYPE: PRT
<213> ORGANISM: Artificial Sequence
<220> FEATURE:
<223> OTHER INFORMATION: Chemically synthesized peptide

<400> SEQUENCE: 18

Gly Ser Trp Glu Ser Gly Ser Asn Ala Tyr Lys
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Chemically synthesized peptide

<400> SEQUENCE: 19

His Cys Gly Asp Pro Cys Cys Thr Thr Cys
1               5                   10
```

<210> SEQ ID NO 20
<211> LENGTH: 128
<212> TYPE: PRT
<213> ORGANISM: Artificial Sequence
<220> FEATURE:
<223> OTHER INFORMATION: Chemically synthesized peptide

<400> SEQUENCE: 20

```
Gln Val Gln Leu Val Gln Ser Gly Ala Gln Val Lys Met Pro Gly Glu
1               5                   10                  15
Ser Leu Lys Val Ser Cys Lys Ala Ser Gly Tyr Thr Phe Asp Asp Tyr
            20                  25                  30
Gly Met Gly Trp Val Arg Gln Ala Pro Gly Gln Cys Leu Glu Trp Met
        35                  40                  45
Gly Trp Ile Ser Pro Tyr Thr Gly Arg Thr Asn Ser Ser Asp Lys Phe
    50                  55                  60
Gln Gly Arg Val Thr Met Thr Arg Asp Thr Ser Thr Ser Thr Ala Tyr
65                  70                  75                  80
Met Glu Leu Arg Ser Leu Arg Ser Glu Asp Thr Ala Val Tyr Tyr Cys
                85                  90                  95
Ala Arg Asp Gly Thr Tyr Tyr Asp Phe Trp Ser Gly Tyr Phe Asp Asn
            100                 105                 110
Asn Ala Phe Asp Ile Trp Gly Gln Gly Thr Leu Val Thr Val Ser Ser
        115                 120                 125
```

<210> SEQ ID NO 21
<211> LENGTH: 128
<212> TYPE: PRT
<213> ORGANISM: Artificial Sequence
<220> FEATURE:
<223> OTHER INFORMATION: Chemically synthesized peptide

<400> SEQUENCE: 21

```
Gln Val Gln Leu Val Gln Ser Gly Ala Gln Val Lys Met Pro Gly Glu
1               5                   10                  15
Ser Leu Lys Val Ser Cys Lys Ala Ser Gly Tyr Thr Phe Thr Asp Tyr
            20                  25                  30
Gly Met Gly Trp Val Arg Gln Ala Pro Gly Gln Gly Leu Glu Trp Met
        35                  40                  45
Gly Trp Ile Ser Pro Tyr Thr Gly Arg Thr Asn Ser Ser Asp Lys Phe
    50                  55                  60
Gln Gly Arg Val Thr Met Thr Arg Asp Thr Ser Thr Ser Thr Ala Tyr
65                  70                  75                  80
Met Glu Leu Arg Ser Leu Arg Ser Glu Asp Thr Ala Val Tyr Tyr Cys
                85                  90                  95
Ala Arg Asp Gly Thr Tyr Tyr Asp Phe Trp Ser Gly Tyr Phe Asp Asn
            100                 105                 110
Asn Ala Phe Asp Ile Trp Gly Gln Gly Thr Leu Val Thr Val Ser Ser
        115                 120                 125
```

<210> SEQ ID NO 22
<211> LENGTH: 110
<212> TYPE: PRT
<213> ORGANISM: Artificial Sequence
<220> FEATURE:
<223> OTHER INFORMATION: Chemically synthesized peptide

<400> SEQUENCE: 22

-continued

Gln Ser Val Val Thr Gln Pro Pro Ser Val Ser Gly Ala Pro Gly Gln
1               5                   10                  15

Arg Val Thr Ile Ser Cys Ser Gly Ser Thr Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Tyr Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Thr Glu Asp Glu Ala Asp Tyr Tyr Cys Gly Thr Trp Asp Ser Ser Leu
                85                  90                  95

Asn Ala Trp Val Phe Gly Gly Gly Thr Lys Leu Thr Val Leu
            100                 105                 110

<210> SEQ ID NO 23
<211> LENGTH: 110
<212> TYPE: PRT
<213> ORGANISM: Artificial Sequence
<220> FEATURE:
<223> OTHER INFORMATION: Chemically synthesized peptide

<400> SEQUENCE: 23

Gln Ser Val Val Thr Gln Pro Pro Ser Val Ser Gly Ala Pro Gly Gln
1               5                   10                  15

Arg Val Thr Ile Ser Cys Ser Gly Ser Thr Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Tyr Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gly Ser Trp Glu Ser Gly Ser
                85                  90                  95

Asn Ala Tyr Lys Phe Gly Gly Gly Thr Lys Leu Thr Val Leu
            100                 105                 110

<210> SEQ ID NO 24
<211> LENGTH: 8
<212> TYPE: PRT
<213> ORGANISM: Artificial Sequence
<220> FEATURE:
<223> OTHER INFORMATION: Chemically synthesized peptide

<400> SEQUENCE: 24

Gly Tyr Thr Phe Thr Asp Tyr Gly
1               5

<210> SEQ ID NO 25
<211> LENGTH: 8
<212> TYPE: PRT
<213> ORGANISM: Artificial Sequence
<220> FEATURE:
<223> OTHER INFORMATION: Chemically synthesized peptide

<400> SEQUENCE: 25

Ile Ser Pro Tyr Thr Gly Arg Thr
1               5

-continued

<210> SEQ ID NO 26
<211> LENGTH: 330
<212> TYPE: PRT
<213> ORGANISM: Artificial Sequence
<220> FEATURE:
<223> OTHER INFORMATION: Chemically synthesized peptide

<400> SEQUENCE: 26

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 27
<211> LENGTH: 493
<212> TYPE: PRT
<213> ORGANISM: Artificial
<220> FEATURE:
<223> OTHER INFORMATION: Chemically synthesized peptide

<400> SEQUENCE: 27

```
Gln Ser Val Val Thr Gln Pro Pro Ser Val Ser Ala Ala Pro Gly Gln
1               5                   10                  15

Lys Val Thr Ile Ser Cys Ser Gly Ser Thr Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Tyr Lys Arg Pro Ser Gly Ile Pro Asp Arg Phe Ser
    50                  55                  60

Gly Ser Lys Ser Gly Thr Ser Ala Thr Leu Gly Ile Thr Gly Leu Arg
65                  70                  75                  80

Thr Gly Asp Glu Ala Asp Tyr Phe Cys Gly Thr Trp Asp Ser Ser Leu
                85                  90                  95

Asn Ala Trp Val Phe Gly Gly Thr Lys Leu Thr Val Leu Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys Phe Ile Ile Asn Glu Glu Phe
    210                 215                 220

Lys Met Lys Tyr Leu Leu Pro Thr Ala Ala Gly Leu Leu Leu Leu
225                 230                 235                 240

Ala Ala Gln Pro Ala Met Ala Gln Val Gln Leu Val Gln Ser Gly Thr
                245                 250                 255

Gln Val Lys Met Pro Gly Ala Ser Val Lys Val Ser Cys Lys Ala Ser
            260                 265                 270

Gly Tyr Thr Phe Asp Asp Tyr Gly Ile Gly Trp Val Arg Gln Ala Pro
        275                 280                 285

Gly Gln Gly Leu Glu Trp Met Gly Trp Ile Ser Pro Tyr Thr His Arg
    290                 295                 300

Thr Asn Ser Ser Pro Lys Leu Gln Asp Arg Val Thr Met Thr Thr Asp
305                 310                 315                 320

Thr Ser Thr Ser Thr Ala Tyr Met Glu Leu Arg Ser Leu Arg Ser Asp
                325                 330                 335

Asp Thr Ala Val Tyr Tyr Cys Ala Arg Asp Gly Thr Tyr Tyr Asp Phe
            340                 345                 350

Trp Ser Gly Tyr Phe Asp Asn Gly Ala Phe Asp Ile Trp Gly Gln Gly
        355                 360                 365

Thr Leu Val Thr Val Ser Ser Ala Ser Thr Lys Gly Pro Ser Val Phe
    370                 375                 380

Pro Leu Ala Pro Ser Ser Lys Ser Thr Ser Gly Gly Thr Ala Ala Leu
385                 390                 395                 400

Gly Cys Leu Val Lys Asp Tyr Phe Pro Glu Pro Val Thr Val Ser Trp
```

```
                    405                 410                 415
Asn Ser Gly Ala Leu Thr Ser Gly Val His Thr Phe Pro Ala Val Leu
                420                 425                 430

Gln Ser Ser Gly Leu Tyr Ser Leu Ser Ser Val Val Thr Val Pro Ser
            435                 440                 445

Ser Ser Leu Gly Thr Gln Thr Tyr Ile Cys Asn Val Asn His Lys Pro
        450                 455                 460

Ser Asn Thr Lys Val Asp Lys Lys Val Glu Pro Lys Ser Cys Asp Lys
465                 470                 475                 480

Thr Ser Gly Gln Ala Gly Gln His His His His His
                    485                 490

<210> SEQ ID NO 28
<211> LENGTH: 491
<212> TYPE: PRT
<213> ORGANISM: Artificial
<220> FEATURE:
<223> OTHER INFORMATION: Chemically synthesized peptide

<400> SEQUENCE: 28

Gln Ser Val Val Thr Gln Pro Pro Ser Val Ser Ala Ala Pro Gly Gln
1               5                   10                  15

Lys Val Thr Ile Ser Cys Ser Gly Ser Thr Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Tyr Lys Arg Pro Ser Gly Ile Pro Asp Arg Phe Ser
        50                  55                  60

Gly Ser Lys Ser Gly Thr Ser Ala Thr Leu Gly Ile Thr Gly Leu Arg
65                  70                  75                  80

Thr Gly Asp Glu Ala Asp Tyr Phe Gly Thr Trp Asp Ser Ser Leu Asn
                85                  90                  95

Ala Trp Val Phe Gly Gly Gly Thr Lys Leu Thr Val Leu Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Phe Ile Ile Asn Glu Glu Phe Lys
    210                 215                 220

Met Lys Tyr Leu Leu Pro Thr Ala Ala Ala Gly Leu Leu Leu Leu Ala
225                 230                 235                 240

Ala Gln Pro Ala Met Ala Gln Val Gln Leu Val Gln Ser Gly Thr Gln
                245                 250                 255

Val Lys Met Pro Gly Ala Ser Val Lys Val Ser Cys Lys Ala Ser Gly
            260                 265                 270

Tyr Thr Phe Asp Asp Tyr Gly Ile Gly Trp Val Arg Gln Ala Pro Gly
```

```
                275                 280                 285
Gln Gly Leu Glu Trp Met Gly Trp Ile Ser Pro Tyr Thr His Arg Thr
        290                 295                 300

Asn Ser Ser Pro Lys Leu Gln Asp Arg Val Thr Met Thr Thr Asp Thr
305                 310                 315                 320

Ser Thr Ser Thr Ala Tyr Met Glu Leu Arg Ser Leu Arg Ser Asp Asp
                325                 330                 335

Thr Ala Val Tyr Tyr Ala Arg Asp Gly Thr Tyr Tyr Asp Phe Trp Ser
            340                 345                 350

Gly Tyr Phe Asp Asn Gly Ala Phe Asp Ile Trp Gly Gln Gly Thr Leu
        355                 360                 365

Val Thr Val Ser Ser Ala Ser Thr Lys Gly Pro Ser Val Phe Pro Leu
    370                 375                 380

Ala Pro Ser Ser Lys Ser Thr Ser Gly Gly Thr Ala Ala Leu Gly Cys
385                 390                 395                 400

Leu Val Lys Asp Tyr Phe Pro Glu Pro Val Thr Val Ser Trp Asn Ser
                405                 410                 415

Gly Ala Leu Thr Ser Gly Val His Thr Phe Pro Ala Val Leu Gln Ser
            420                 425                 430

Ser Gly Leu Tyr Ser Leu Ser Ser Val Val Thr Val Pro Ser Ser Ser
        435                 440                 445

Leu Gly Thr Gln Thr Tyr Ile Cys Asn Val Asn His Lys Pro Ser Asn
    450                 455                 460

Thr Lys Val Asp Lys Lys Val Glu Pro Lys Ser Cys Asp Lys Thr Ser
465                 470                 475                 480

Gly Gln Ala Gly Gln His His His His His
                485                 490

<210> SEQ ID NO 29
<211> LENGTH: 330
<212> TYPE: DNA
<213> ORGANISM: Artificial
<220> FEATURE:
<223> OTHER INFORMATION: Chemically synthesized nucleotide

<400> SEQUENCE: 29
cagtctgtcg tgacgcagcc gccctcagtg tctgcggccc caggacagaa ggtcaccatc      60
tcctgctctg gaagcaccct caacattggg aataattatg tatcctggta ccagcaactc     120
ccaggaacag ccccccaaact cctcatttat gacaattata gcgaccctc tgggattcct     180 gaccgattct ctggctccaa gtctggcacg tcagccaccc tgggcatcac cggactccgg     240
actggggacg aggccgatta tttctgcgga acatgggata gtagcctgaa tgcttgggtg     300
ttcggcgggg ggaccaagct gaccgtccta                                     330

<210> SEQ ID NO 30
<211> LENGTH: 110
<212> TYPE: PRT
<213> ORGANISM: Artificial
<220> FEATURE:
<223> OTHER INFORMATION: Chemically synthesized peptide

<400> SEQUENCE: 30

Gln Ser Val Val Thr Gln Pro Pro Ser Val Ser Ala Ala Pro Gly Gln
1               5                   10                  15

Lys Val Thr Ile Ser Cys Ser Gly Ser Thr Ser Asn Ile Gly Asn Asn
            20                  25                  30
```

Tyr Val Ser Trp Tyr Gln Gln Leu Pro Gly Thr Ala Pro Lys Leu Leu
            35                  40                  45

Ile Tyr Asp Asn Tyr Lys Arg Pro Ser Gly Ile Pro Asp Arg Phe Ser
        50                  55                  60

Gly Ser Lys Ser Gly Thr Ser Ala Thr Leu Gly Ile Thr Gly Leu Arg
65                  70                  75                  80

Thr Gly Asp Glu Ala Asp Tyr Phe Cys Gly Thr Trp Asp Ser Ser Leu
                85                  90                  95

Asn Ala Trp Val Phe Gly Gly Gly Thr Lys Leu Thr Val Leu
            100                 105                 110

<210> SEQ ID NO 31
<211> LENGTH: 381
<212> TYPE: DNA
<213> ORGANISM: Artificial
<220> FEATURE:
<223> OTHER INFORMATION: Chemically synthesized nucletoide

<400> SEQUENCE: 31
caggtccagc tggtgcagtc tggaactcag gtgaagatgc ctggggcctc agtgaaggtc     60
tcctgcaagg cttctggtta ccctttgac gactatggta tcggctgggt gcgacaggcc    120
cctggacaag gcttgaatg gatgggatgg atcagccctt acactcatag gacaaattct    180
tcaccgaagc tccaggacag agtcaccatg accacagaca catccacgag cacagcctac    240
atggagctga ggagcctgag atctgacgac acggccgtgt attactgtgc gagagatggg    300
acgtattacg attttagtgg ttatttcgac aatggtgctt ttgatatctg gggccaaggc    360
accctggtca ccgtctcctc a                                              381

<210> SEQ ID NO 32
<211> LENGTH: 128
<212> TYPE: PRT
<213> ORGANISM: Artificial
<220> FEATURE:
<223> OTHER INFORMATION: Chemically synthesized peptide

<400> SEQUENCE: 32

Gln Val Gln Leu Val Gln Ser Gly Thr Gln Val Lys Met Pro Gly Ala
1               5                   10                  15

Ser Val Lys Val Ser Cys Lys Ala Ser Gly Tyr Thr Phe Asp Asp Tyr
            20                  25                  30

Gly Ile Gly Trp Val Arg Gln Ala Pro Gly Gln Gly Leu Glu Trp Met
        35                  40                  45

Gly Trp Ile Ser Pro Tyr Thr His Arg Thr Asn Ser Ser Pro Lys Leu
    50                  55                  60

Gln Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Thr Tyr Tyr Asp Phe Trp Ser Gly Tyr Phe Asp Asn
            100                 105                 110

Gly Ala Phe Asp Ile Trp Gly Gln Gly Thr Leu Val Thr Val Ser Ser
        115                 120                 125

IFN-γ-INDUCIBLE REGULATORY T CELL CONVERTIBLE ANTI-CANCER (IRTCA) ANTIBODY AND USES THEREOF

CROSS-REFERENCE TO RELATED APPLICATIONS

This application is a continuation application claiming priority to PCT Application No. PCT/IB2018/000201, filed on Feb. 9, 2018, which claims priority to and the benefit of U.S. Patent Application No. 62/457,422, filed on Feb. 10, 2017. The entire contents of the foregoing are herein incorporated by reference.

SEQUENCE LISTING

The present specification makes reference to a Sequence Listing (submitted electronically as a .txt file named "2012994-0030_SL.txt" on Feb. 9, 2018). The .txt file was generated on Feb. 9, 2018 and is 19,405 bytes in size. The entire contents of the Sequence Listing are herein incorporated by reference.

BACKGROUND

Cancer remains one of the leading causes of death in the world. Recent statistics report that 13% of the world population dies from cancer. According to estimates from the International Agency for Research on Cancer (IARC), in 2012 there were 14.1 million new cancer cases and 8.2 million cancer deaths worldwide. By 2030, the global burden is expected to grow to 21.7 million new cancer cases and 13 million cancer deaths due to population growth and aging and exposure to risk factors such as smoking, unhealthy diet and physical inactivity. Further, pain and medical expenses for cancer treatment cause reduced quality of life for both cancer patients and their families. It is apparent that, above all, cancer is a disease for which it is necessary to urgently find improved treatment methods.

SUMMARY

The present disclosure provides, among other things, antibodies and fragments thereof that bind to a human activation-inducible TNFR family receptor (AITR) polypeptide. In some embodiments, the present invention provides IFN-γ-Inducible Regulatory T Cell Convertible Anti-Cancer (IRTCA) antibodies and/or antigen-binding fragments thereof, including: (a) a heavy chain CDR1 comprising a sequence of SEQ ID NO: 8 or 24, a heavy chain CDR2 comprising a sequence of SEQ ID NO: 9 or 25, and a heavy chain CDR3 comprising at least one sequence selected from SEQ ID NO: 10, 14, 15, 16, and 17, and (b) a light chain CDR1 comprising a sequence of SEQ ID NO: 11, a light chain CDR2 comprising a sequence of SEQ ID NO: 12, and a light chain CDR3 comprising a sequence of SEQ ID NO: 13 or 18, wherein the IRTCA antibody or antigen-binding fragment thereof does not comprise each of a heavy chain CDR1 comprising a sequence of SEQ ID NO: 8, a heavy chain CDR2 comprising a sequence of SEQ ID NO: 9, a heavy chain CDR3 comprising a sequence of SEQ ID NO: 10, a light chain CDR1 comprising a sequence of SEQ ID NO: 11, a light chain CDR2 comprising a sequence of SEQ ID NO: 12 and a light chain CDR3 comprising a sequence of SEQ ID NO: 13.

In some embodiments, the present invention further provides IRTCA antibodies or antigen-binding fragments wherein the antibody or antigen-binding fragment include any one of the following: (a) a heavy chain variable domain comprising a sequence at least 90% identical to a sequence selected from SEQ ID NOs: 3, 4, 5, 6, 20, and 21; (b) a light chain variable domain comprising a sequence at least 90% identical to a sequence selected from SEQ ID NOs: 7, 22, and 23; or (c) a heavy chain variable domain comprising a sequence at least 90% identical to a sequence selected from SEQ ID NOs: 3, 4, 5, 6, 20, and 21 and a light chain variable domain comprising a sequence at least 98% identical to a sequence selected from SEQ ID NOs: 7, 22, and 23.

In some embodiments, the present invention also provides IRTCA antibodies or antigen-binding fragments wherein the antibody or antigen-binding fragment comprises any one of the following: (a) a heavy chain variable domain comprising a sequence at least 98% identical to a sequence selected from SEQ ID NOs: 3, 4, 5, 6, 20, and 21; (b) a light chain variable domain comprising a sequence at least 98% identical to a sequence selected from SEQ ID NOs: 7, 22, and 23; or (c) a heavy chain variable domain comprising a sequence at least 98% identical to a sequence selected from SEQ ID NOs: 3, 4, 5, 6, 20, and 21 and a light chain variable domain comprising a sequence at least 98% identical to a sequence selected from SEQ ID NOs: 7, 22, and 23.

In some embodiments, a provided IRTCA antibody or antigen-binding fragment includes any one of the following: (a) a heavy chain variable domain comprising a sequence selected from SEQ ID NOs: 3, 4, 5, 6, 20, and 21; (b) a light chain variable domain comprising a sequence selected from SEQ ID NOs: 7, 22, and 23; or (c) a heavy chain variable domain comprising a sequence selected from SEQ ID NOs: 3, 4, 5, 6, 20, and 21 and a light chain variable domain comprising a sequence selected from SEQ ID NOs: 7, 22, and 23.

In some embodiments, an IRTCA antibody or antigen-binding fragment thereof does not include each of a heavy chain CDR1 comprising a sequence of SEQ ID NO: 8, a heavy chain CDR2 comprising a sequence of SEQ ID NO: 9, a heavy chain CDR3 comprising a sequence of SEQ ID NO: 10, a light chain CDR1 comprising a sequence of SEQ ID NO: 11, a light chain CDR2 comprising a sequence of SEQ ID NO: 12 and a light chain CDR3 comprising a sequence of SEQ ID NO: 13

In accordance with any of a variety of embodiments, provided IRTCA antibodies or antigen-binding fragments thereof, and/or provided compositions may exhibit a range of binding affinities. For example, in some embodiments, a provided IRTCA antibody or antigen-binding fragment has a binding affinity ($K_D$) for a human Activation-Inducible Tumor Necrosis Factor Receptor (TNFR) Family Receptor (AITR) molecule of $1 \times 10^{-7}$ to $1 \times 10^{-12}$ M. In some embodiments, a provided IRTCA antibody or antigen-binding fragment binds to an epitope within the extracellular domain of human AITR polypeptide. In some embodiments, an epitope within the extracellular domain of human AITR polypeptide comprises SEQ ID NO: 19.

In some embodiments, a provided antibody or antigen-binding fragment is or comprises a humanized antibody. In some embodiments, a provided IRTCA antibody or antigen-binding fragment thereof is or comprises a monoclonal antibody. In some embodiments, a provided IRTCA antibody or antigen-binding fragment thereof includes an immunoglobulin constant domain, wherein the constant domain is selected from an IgG1 or a variant thereof, an IgG2 or a variant thereof, an IgG4 or a variant thereof, an IgA or a variant thereof, an IgE or a variant thereof, an IgM or a variant thereof, and an IgD or a variant thereof. In some embodiments, a provided IRTCA antibody or antigen-binding fragment thereof is or comprises a human IgG1. In some embodiments, the IgG1 is or comprises a sequence that is at least 95% identical to SEQ ID NO: 26. In some embodiments, a provided IRTCA antibody or antigen-binding fragment thereof is or comprises a Fab fragment, a Fab' fragment, a F(ab')2 fragment, a Fv fragment, a disulfide-bonded Fv fragment, a scFv fragment, a single domain antibody, humabody, nanobody, or a diabody.

In accordance with various embodiments, the present invention provides a variety of molecules and compositions for, inter alia, facilitating delivery and/or expression of a provided composition that comprises an amount of a provided IRTCA antibody or antigen-binding fragment thereof. For example, in some embodiments, the present invention provides nucleic acid molecules encoding an IRTCA antibody or antigen-binding fragment thereof. In some embodiments, the present invention also provides recombinant vectors including such nucleic acid molecules. In some embodiments, the present invention also provides host cells including a provided recombinant vector and/or a provided nucleic acid molecule. In some embodiments, a host cell may be selected from a bacterial, yeast, insect or mammalian cell. In some embodiments a host cell is selected from the group consisting of E. coli, P. pastoris, Sf9, COS, HEK293, Expi293, CHO-S, CHO-DG44, CHO-K1, and a mammalian lymphocyte.

In some embodiments, the present invention provides pharmaceutical compositions including: (a) one or more provided IRTCA antibodies or antigen-binding fragments thereof, one or more provided nucleic acid molecules, one or more provided recombinant vectors, and/or one or more provided host cells, and (b) a pharmaceutically acceptable carrier. Any of a variety of pharmaceutically acceptable carriers may be used in accordance with various embodiments.

In addition to the variety of powerful new antibodies, antigen-binding fragments thereof, and compositions provided herein, the present invention also provides, in various embodiments, a variety of new therapeutic methods as well. For example, and in accordance with various embodiments, the present invention provides methods of treating a subject in need thereof, the method including the step of: administering to the subject a composition that comprises or delivers a provided IRTCA antibody or antigen-binding fragment thereof, a provided nucleic acid molecule, and/or a provided recombinant vector.

By way of additional example, the present invention also provides, in some embodiments, methods of inducing an immune response in a subject in need thereof, the method including the step of: administering to the subject a composition that comprises or delivers a provided IRTCA antibody or antigen-binding fragment thereof, a provided nucleic acid molecule, and/or a provided recombinant vector.

By way of further example, in some embodiments, the present invention also provides methods of enhancing an immune response or increasing the activity of an immune cell in a subject in need thereof, the method including the step of: administering to the subject a composition that comprises or delivers a provided IRTCA antibody or antigen-binding fragment thereof, a provided nucleic acid molecule, and/or a provided recombinant vector.

In some embodiments, the present invention also provides methods for increasing secretion of IFN-γ by a T cell in vivo or in vitro, the method comprising: contacting the cell with a composition that comprises or delivers an amount of a provided IRTCA antibody or antigen-binding fragment thereof. In some embodiments, the present invention also provides methods for decreasing secretion of TGF-β by a T cell in vivo or in vitro, the method comprising: contacting the cell with a composition that comprises or delivers an amount of a provided IRTCA antibody or antigen-binding fragment thereof. In some embodiments, the present invention also provides methods for converting a T cell into a Type 1 helper T ($T_H1$) cell, the method comprising: contacting the cell with a composition that comprises or delivers an amount of a provided IRTCA antibody or antigen-binding fragment thereof.

In some embodiments, the subject has, or is at risk for developing, cancer. In some embodiments, the cancer is selected from a bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, renal cell carcinoma, glioblastoma, and prostate cancer.

It is specifically contemplated that various embodiments are suitable for us in one or more combination therapy regimen. For example, in some embodiments, the subject has been administered or will be administered one or more additional anticancer therapies. In some embodiments, the one or more additional cancer therapies is selected from ionizing radiation, a chemotherapeutic agent, an antibody agent, and a cell-based therapy, such that the subject receives treatment with both. In some embodiments, the one or more additional anticancer therapies comprise an immune checkpoint inhibitor, IL-12, GM-CSF, an anti-CD4 agent, cisplatin, fluorouracil, doxorubicin, irinotecan, paclitaxel, indoleamine 2,3-dioxygenase-1 (IDO1) inhibitor, or cyclophosphamide.

Various embodiments of the present invention may also be useful for determining an advantageous dosing regimen for one or more provided IRTCA antibodies and/or antigen binding fragments thereof, nucleic acid molecules, recombinant vectors, and/or host cells. For example, in some embodiments, the present invention provides methods of determining a dose of an IRTCA antibody or antigen binding fragment thereof for therapeutic treatment of a subject in need thereof, the method including the steps of: (a) providing or obtaining a measurement of secreted IFN-γ in a biological sample from the subject, wherein the subject has been administered a composition that comprises or delivers an amount of a provided IRTCA antibody or antigen-binding fragment thereof, and (b) comparing the measurement of secreted IFN-γ to a reference value, wherein if the measurement of secreted IFN-γ is higher or lower than the reference value, adjusting the amount of the IRTCA antibody or antigen binding fragment thereof to be administered, thereby determining a dose for therapeutic treatment of a subject.

In some embodiments, a reference value may be a level of IFN-γ in a biological sample from the subject prior to administration of the provided IRTCA antibody or antigen-binding fragment thereof. In some embodiments, if a measured amount of secreted IFN-γ in a biological sample from the subject is higher than a reference value, then treatment is either maintained at the same level given previously, or treatment is ceased for a period of time.

By way of additional example, in some embodiments, the present invention provides methods of determining a dose of an IRTCA antibody or antigen binding fragment thereof for therapeutic treatment of a subject in need thereof, including the steps of: (a) providing or obtaining a measurement of $T_{reg}$ cell population in a biological sample from the subject, wherein the subject has been administered a composition that comprises or delivers an amount of a provided IRTCA antibody or antigen-binding fragment thereof; and (b) comparing the measurement of $T_{reg}$ cell population to a reference value, wherein if the measurement of $T_{reg}$ cell population is higher or lower than the reference value, adjusting the amount of the IRTCA antibody or antigen binding fragment thereof to be administered, thereby determining a dose for therapeutic treatment of a subject. In some embodiments, a reference value may be a level of $T_{reg}$ cell population in a biological sample from the subject prior to administration of the provided IRTCA antibody or antigen-binding fragment thereof. In some embodiments, if a measured amount of $T_{reg}$ cell population in a biological sample from the subject is lower than a reference value, then treatment is either maintained at the same level given previously, or treatment is ceased for a period of time.

By way of additional example, in some embodiments, the present invention provides methods of determining a dose of an IRTCA antibody or antigen binding fragment thereof for therapeutic treatment of a subject in need thereof, including the steps of: (a) providing or obtaining a measurement of IFN-γ-secreting T cell population in a biological sample from the subject, wherein the subject has been administered a composition that comprises or delivers an amount of a provided IRTCA antibody or antigen-binding fragment thereof; (b) providing or obtaining a measurement of $T_{reg}$ cell population in a biological sample from the subject, wherein the subject has been administered a composition that comprises or delivers an amount of a provided IRTCA antibody or antigen-binding fragment thereof; (c) calculating the ratio of the measurement of IFN-γ-secreting T cell population to the measurement of $T_{reg}$ cell population; and (d) comparing the ratio to a reference value, wherein if ratio is higher or lower than the reference value, adjusting the amount of the IRTCA antibody or antigen binding fragment thereof to be administered, thereby determining a dose for therapeutic treatment of a subject. In some embodiments, a reference value may be a ratio of a level of IFN-γ-secreting T cell population in a biological sample from a subject to a level of $T_{reg}$ cell population in the same biological sample from the subject prior to administration of the provided IRTCA antibody or antigen-binding fragment thereof. In some embodiments, if a calculated ratio in a biological sample from the subject is higher than a reference value, then treatment is either maintained at the same level given previously, or treatment is ceased for a period of time.

In some embodiments, a reference value comprises an index value which includes a value derived from one or more healthy subjects or a value derived from one or more cancer-diagnosed subjects. In some embodiments, a biological sample is a sample of whole blood, plasma, tumor tissue, or serum.

In some embodiments, the present invention also provides methods of validating affinity of an antibody or antigen-binding fragment thereof for AITR, the method including the steps of: contacting a T cell with a composition that comprises or delivers an amount of a provided IRTCA antibody or antigen-binding fragment thereof, and measuring cytokine secretion from the T cell, wherein cytokine secretion correlates with immune response enhancement, anti-cancer effects and/or anti-tumor effects of the IRTCA antibody. In some embodiments, the T cell expresses AITR protein. In some embodiments, the T cell is a regulatory T cell ($T_{reg}$ cell). In some embodiments, the T cell is an effector T cell ($T_{eff}$ cell).

As used in this application, the terms "about" and "approximately" are used as equivalents. Any citations to publications, patents, or patent applications herein are incorporated by reference in their entirety. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWING

The Drawing included herein, which is comprised of the following Figures, is for illustration purposes only and not for limitation. The foregoing and other objects, aspects, features, and advantages of the present disclosure will become more apparent and better understood by referring to the following description taken in conjunction with the accompanying figures in which:

FIG. 1 shows Fab type amino acid sequences of IRTCA-A, wherein a and b respectively represent the amino acid sequence of the IRTCA-A Fab type and the IRTCA-A amino acid sequence into which a stop codon is inserted (asterisk indicates stop codon).

FIG. 7C depicts a graph quantifying dose-dependent changes in secretion of TGF-β in $T_{reg}$ cells after treatment with several IRTCA-A mutants.

CERTAIN DEFINITIONS

Figure 2:
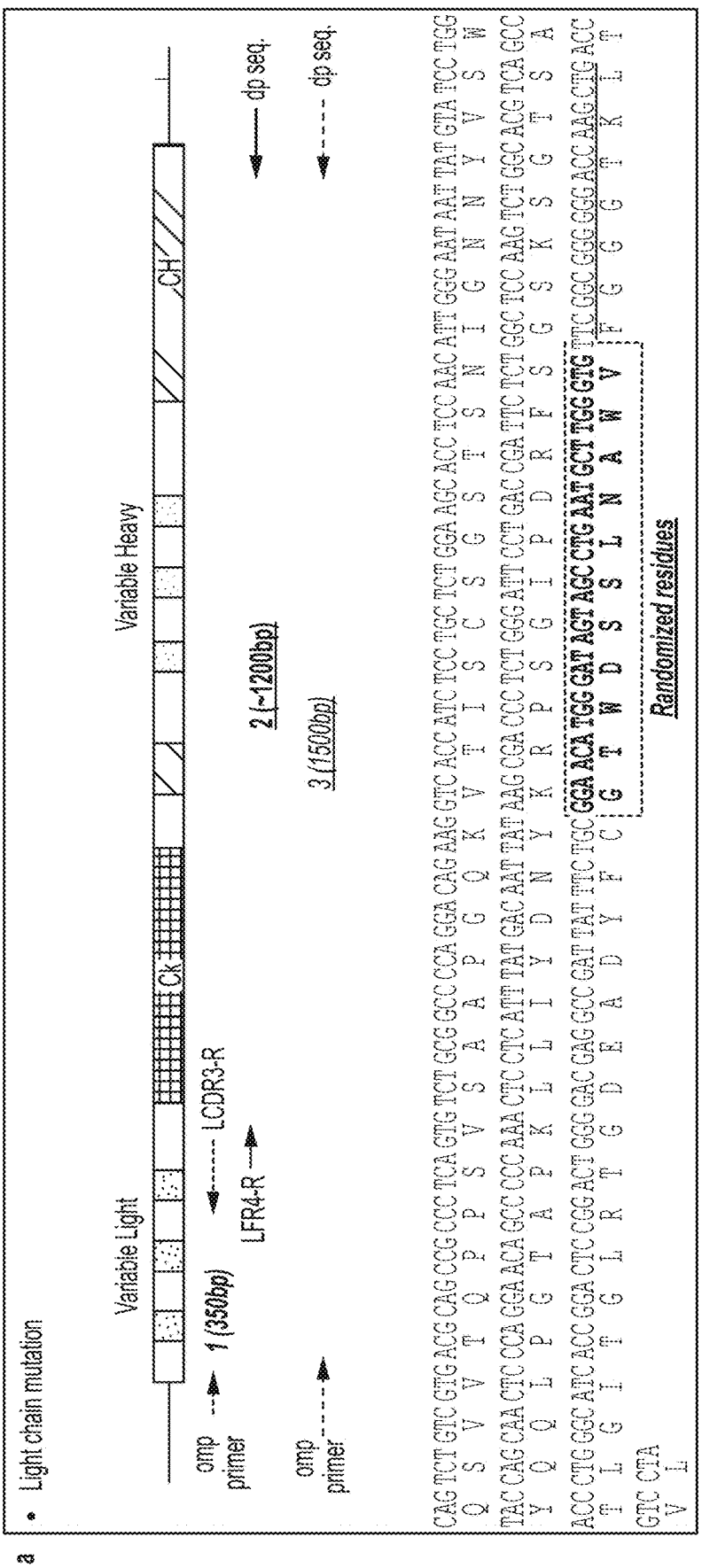
FIG. 2 shows the amino acid regions of IRTCA-A in which randomized PCR configuration and mutation were induced. Panel a shows the IRTCA-A light chain, and panel b shows the IRTCA-A heavy chain. A random primer was used so that mutation might be induced at the CDR3 region, and a phage display library where mutation was concentrated in the CDR3 area was fabricated.
Figure 2:
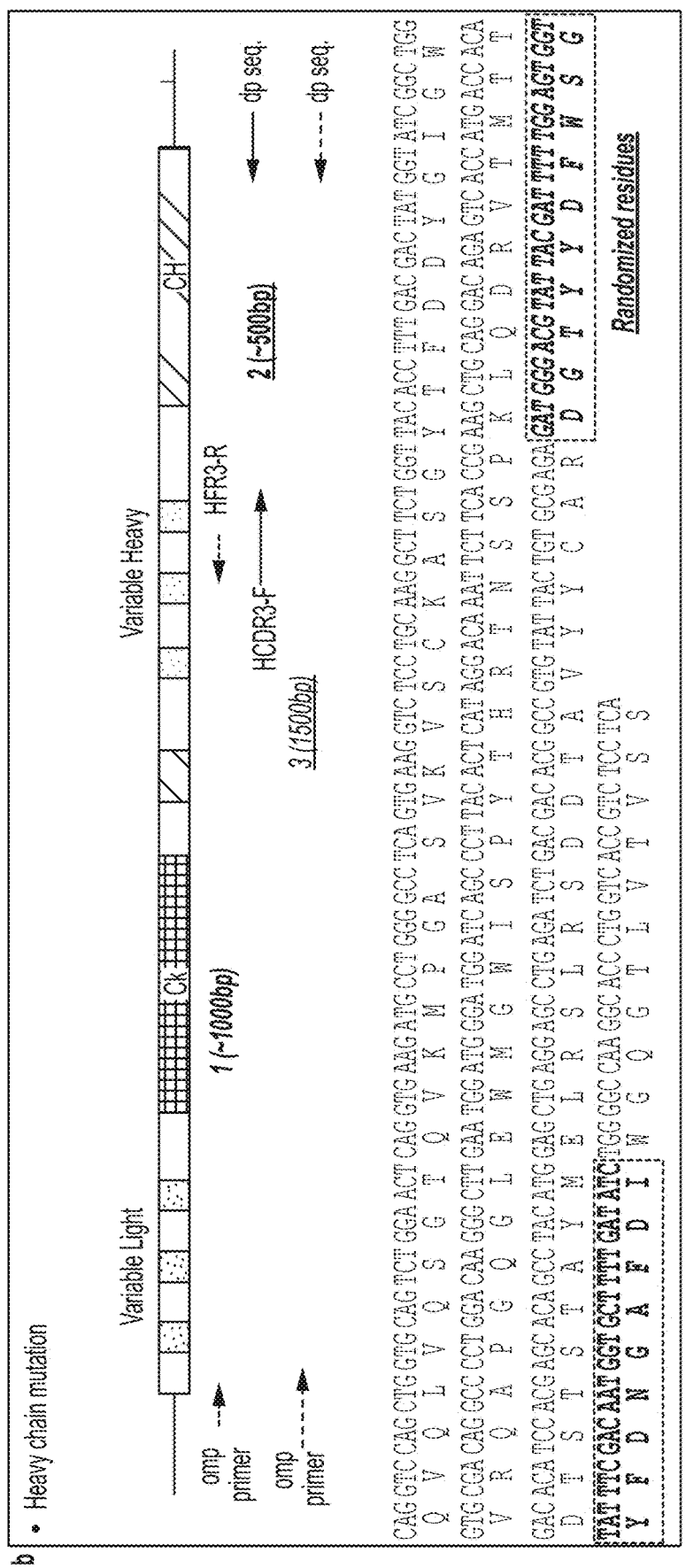
Figure 3:
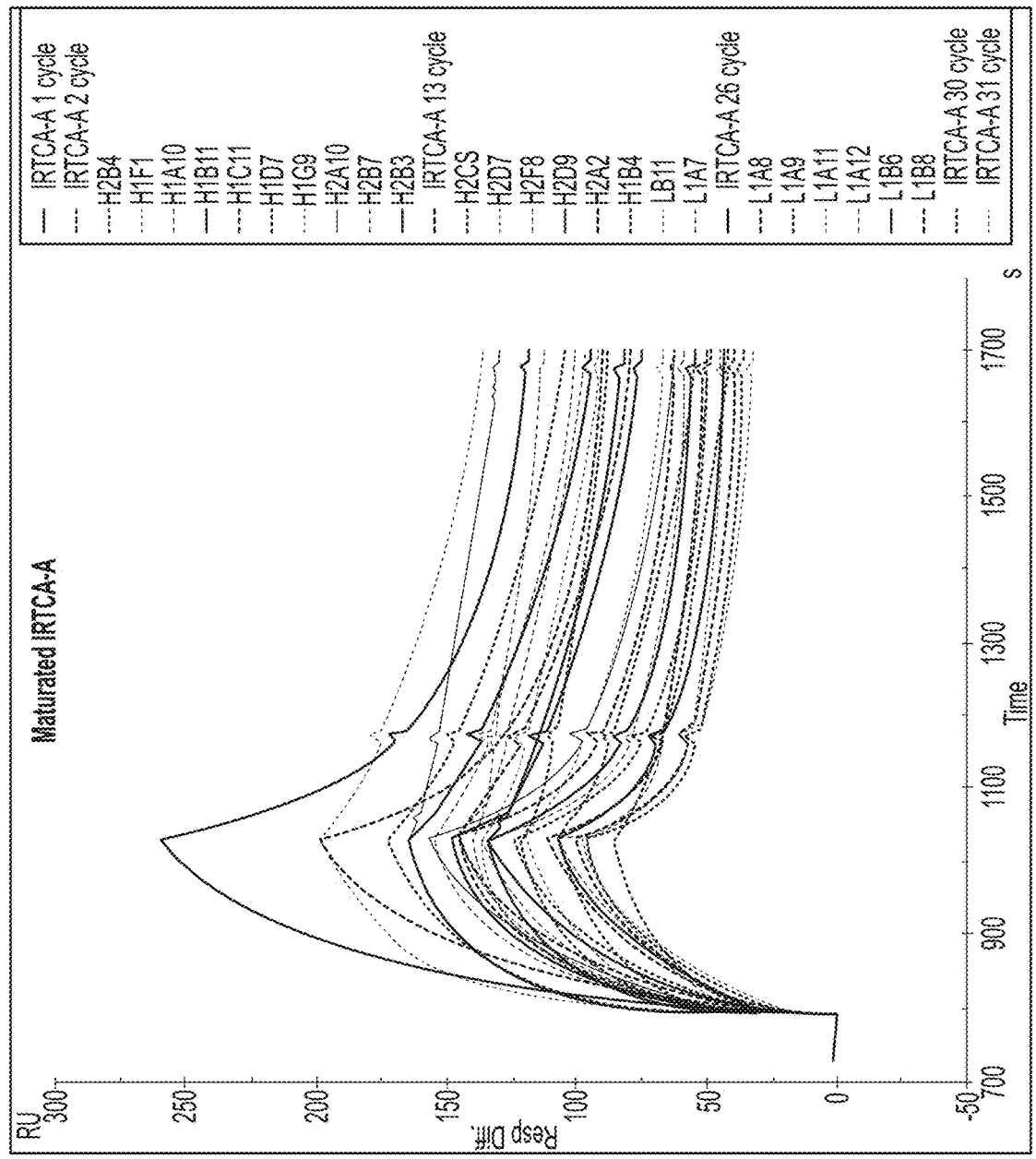
FIG. 3 shows the dissociation curve overlay plot for the AITR antigen of 16 heavy chain mutants and 9 light chain mutants in the IRTCA-A series.
Figure 4:
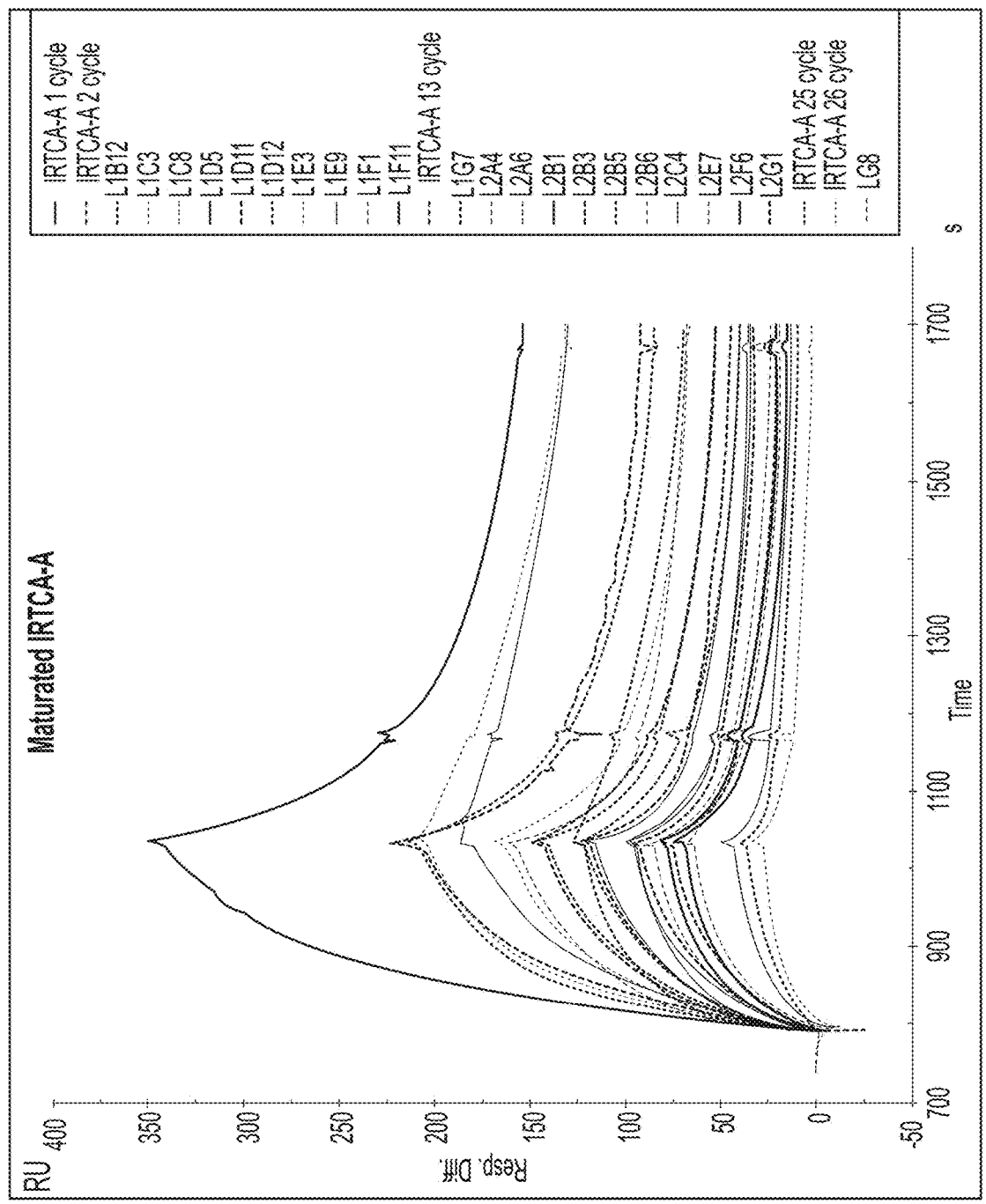
FIG. 4 shows the dissociation curve overlay plot for the AITR antigen of 22 light chain mutants in the IRTCA-A series.

In the description that follows, a number of terms used in recombinant DNA and immunology are extensively utilized. In order to provide a clearer and consistent understanding of the specification and claims, including the scope to be given such terms, the following definitions are provided.

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Administration: As used herein, the term "administration" typically refers to the administration of a composition to a subject or system to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e.g. intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Affinity: As is known in the art, "affinity" is a measure of the tightness with a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

Agonist: Those skilled in the art will appreciate that the term "agonist" may be used to refer to an agent condition, or event whose presence, level, degree, type, or form correlates with an increased level of activity of another agent (i.e., the agonized agent). In general, an agonist may be or include an agent of any chemical class including, for example, small molecules, polypeptides, nucleic acids, carbohydrates, lipids, metals, and/or any other entity that shows the relevant activating activity. In some embodiments, an agonist may be direct (in which case it exerts its influence directly upon its target); in some embodiments, an agonist may be indirect (in which case it exerts its influence by other than binding to its target; e.g., by interacting with a regulator of the target, so that level or activity of the target is altered).

Animal: as used herein refers to any member of the animal kingdom. In some embodiments, "αηimαl" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically engineered animal, and/or a clone.

Antagonist: Those skilled in the art will appreciate that the term "antagonist", as used herein, may be used to refer to an agent condition, or event whose presence, level, degree, type, or form correlates with decreased level or activity of another agent (i.e., the inhibited agent, or target). In general, an antagonist may be or include an agent of any chemical class including, for example, small molecules, polypeptides, nucleic acids, carbohydrates, lipids, metals, and/or any other entity that shows the relevant inhibitory activity. In some embodiments, an antagonist may be direct (in which case it exerts its influence directly upon its target); in some embodiments, an antagonist may be indirect (in which case it exerts its influence by other than binding to its target; e.g., by interacting with a regulator of the target, so that level or activity of the target is altered).

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc., as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgA, IgG, IgE or IgM antibodies; bi- or multi-specific antibodies (e.g., Zybodies®, etc.); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); humabodies, VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®; Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc.], or other pendant group [e.g., poly-ethylene glycol, etc.]

Antibody fragment: As used herein, an "antibody fragment" refers to a portion of an antibody or antibody agent as described herein, and typically refers to a portion that includes an antigen-binding portion or variable region thereof. An antibody fragment may be produced by any means. For example, in some embodiments, an antibody fragment may be enzymatically or chemically produced by fragmentation of an intact antibody or antibody agent. Alternatively, in some embodiments, an antibody fragment may be recombinantly produced (i.e., by expression of an engineered nucleic acid sequence. In some embodiments, an antibody fragment may be wholly or partially synthetically produced. In some embodiments, an antibody fragment (particularly an antigen-binding antibody fragment) may have a length of at least about 50, 60, 70, 80, 90, 100, 110, 120, 130, 140, 150, 160, 170, 180, 190 amino acids or more, in some embodiments at least about 200 amino acids.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

Cancer: The terms "cancer", "malignancy", "neoplasm", "tumor", and "carcinoma", are used herein to refer to cells that exhibit relatively abnormal, uncontrolled, and/or autonomous growth, so that they exhibit an aberrant growth phenotype characterized by a significant loss of control of cell proliferation. In some embodiments, a tumor may be or comprise cells that are precancerous (e.g., benign), malignant, pre-metastatic, metastatic, and/or non-metastatic. The present disclosure specifically identifies certain cancers to which its teachings may be particularly relevant. In some embodiments, a relevant cancer may be characterized by a solid tumor. In some embodiments, a relevant cancer may be characterized by a hematologic tumor. In general, examples of different types of cancers known in the art include, for example, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like.

CDR: as used herein, refers to a complementarity determining region within an antibody variable region. There are three CDRs in each of the variable regions of the heavy chain and the light chain, which are designated CDR1, CDR2 and CDR3, for each of the variable regions. A "set of CDRs" or "CDR set" refers to a group of three or six CDRs that occur in either a single variable region capable of binding the antigen or the CDRs of cognate heavy and light chain variable regions capable of binding the antigen. Certain systems have been established in the art for defining CDR boundaries (e.g., Kabat, Chothia, etc.); those skilled in the art appreciate the differences between and among these systems and are capable of understanding CDR boundaries to the extent required to understand and to practice the claimed invention.

Chemotherapeutic Agent. The term "chemotherapeutic agent", has used herein has its art-understood meaning referring to one or more pro-apoptotic, cytostatic and/or cytotoxic agents, for example specifically including agents utilized and/or recommended for use in treating one or more diseases, disorders or conditions associated with undesirable cell proliferation. In many embodiments, chemotherapeutic agents are useful in the treatment of cancer. In some embodiments, a chemotherapeutic agent may be or comprise one or more alkylating agents, one or more anthracyclines, one or more cytoskeletal disruptors (e.g. microtubule targeting agents such as taxanes, maytansine and analogs thereof, of), one or more epothilones, one or more histone deacetylase inhibitors HDACs), one or more topoisomerase inhibitors (e.g., inhibitors of topoisomerase I and/or topoisomerase II), one or more kinase inhibitors, one or more nucleotide analogs or nucleotide precursor analogs, one or more peptide antibiotics, one or more platinum-based agents, one or more retinoids, one or more *vinca* alkaloids, and/or one or more analogs of one or more of the following (i.e., that share a relevant anti-proliferative activity). In some particular embodiments, a chemotherapeutic agent may be or comprise one or more of Actinomycin, All-trans retinoic acid, an Auiristatin, Azacitidine, Azathioprine, Bleomycin, Bortezomib, Carboplatin, Capecitabine, Cisplatin, Chlorambucil, Cyclophosphamide, Curcumin, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Maytansine and/or analogs thereof (e.g. DM1) Mechlorethamine, Mercaptopurine, Methotrexate, Mitoxantrone, a Maytansinoid, Oxaliplatin, Paclitaxel, Pemetrexed, Teniposide, Tioguanine, Topotecan, Valrubicin, Vinblastine, Vincristine, Vindesine, Vinorelbine, and combinations thereof. In some embodiments, a chemotherapeutic agent may be utilized in the context of an antibody-drug conjugate. In some embodiments, a chemotherapeutic agent is one found in an antibody-drug conjugate selected from the group consisting of: hLL1-doxorubicin, hRS7-SN-38, hMN-14-SN-38, hLL2-SN-38, hA20-SN-38, hPAM4-SN-38, hLL1-SN-38, hRS7-Pro-2-P-Dox, hMN-14-Pro-2-P-Dox, hLL2-Pro-2-P-Dox, hA20-Pro-2-P-Dox, hPAM4-Pro-2-P-Dox, hLL1-Pro-2-P-Dox, P4/D10-doxorubicin, gemtuzumab ozogamicin, brentuximab vedotin, trastuzumab emtansine, inotuzumab ozogamicin, glembatumomab vedotin, SAR3419, SAR566658, BIIB015, BT062, SGN-75, SGN-CD19A, AMG-172, AMG-595, BAY-94-9343, ASG-SME, ASG-22ME, ASG-16M8F, MDX-1203, MLN-0264, anti-PSMA ADC, RG-7450, RG-7458, RG-7593, RG-7596, RG-7598, RG-7599, RG-7600, RG-7636, ABT-414, FMGN-853, FMGN-529, vorsetuzumab mafodotin, and lorvotuzumab mertansine.

Corresponding to. As used herein, the term "corresponding to" may be used to designate the position/identity of a structural element in a compound or composition through comparison with an appropriate reference compound or composition. For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at 190 in the reference polypeptide; those of ordinary skill in the art readily appreciate how to identify "corresponding" amino acids. For example, those skilled in the art will be aware of various sequence alignment strategies, including software programs such as, for example, BLAST, CS-BLAST, CUSASW++, DIAMOND, FASTA, GGSEARCH/GL SEARCH, Genoogle, HMMER, HHpred/HHsearch, IDF, Infernal, KLAST, USEARCH, parasail, PSI-BLAST, PSI-Search, ScalaBLAST, Sequilab, SAM, SSEARCH, SWAPHI, SWAPHI-LS, SWIMM, or SWIPE that can be utilized, for example, to identify "corresponding" residues in polypeptides and/or nucleic acids in accordance with the present disclosure.

Engineered: In general, the term "engineered" refers to the aspect of having been manipulated by the hand of man. For example, a polypeptide is considered to be "engineered" when the polypeptide sequence manipulated by the hand of man. For example, in some embodiments of the present invention, an engineered polypeptide comprises a sequence that includes one or more amino acid mutations, deletions and/or insertions that have been introduced by the hand of man into a reference polypeptide sequence. Comparably, a cell or organism is considered to be "engineered" if it has been manipulated so that its genetic information is altered {e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, derivatives and/or progeny of an engineered polypeptide or cell are typically still referred to as "engineered" even though the actual manipulation was performed on a prior entity.

Epitope: as used herein, includes any moiety that is specifically recognized by an immunoglobulin (e.g., antibody or receptor) binding component. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some such chemical atoms are groups are physically separated from one another when the antigen adopts an alternative conformation (e.g., is linearized).

Ex vivo: as used herein refers to biologic events that occur outside of the context of a multicellular organism. For example, in the context of cell-based systems, the term may be used to refer to events that occur among a population of cells (e.g., cell proliferation, cytokine secretion, etc.) in an artificial environment.

Framework or framework region: as used herein, refers to the sequences of a variable region minus the CDRs. Because a CDR sequence can be determined by different systems, likewise a framework sequence is subject to correspondingly different interpretations. The six CDRs divide the framework regions on the heavy and light chains into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, FR1, for example, represents the first framework region closest to the amino terminal end of the variable region and 5' with respect to CDR1, and FRs represents two or more of the sub-regions constituting a framework region.

Humanized: as is known in the art, the term "humanized" is commonly used to refer to antibodies (or antibody components) whose amino acid sequence includes $V_H$ and $V_L$ region sequences from a reference antibody raised in a non-human species (e.g., a mouse), but also includes modifications in those sequences relative to the reference antibody intended to render them more "human-like", i.e., more similar to human germline variable sequences. In some embodiments, a "humanized" antibody (or antibody component) is one that immunospecifically binds to an antigen of interest and that has a framework (FR) region having substantially the amino acid sequence as that of a human antibody, and a complementary determining region (CDR) having substantially the amino acid sequence as that of a non-human antibody. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor immunoglobulin) and all or substantially all of the framework regions are those of a human immunoglobulin consensus sequence. In some embodiments, a humanized antibody also comprises at least a portion of an immunoglobulin constant region (Fc), typically that of a human immunoglobulin constant region. In some embodiments, a humanized antibody contains both the light chain as well as at least the variable domain of a heavy chain. The antibody also may include a $C_H1$, hinge, $C_H2$, $C_H3$, and, optionally, a $C_H4$ region of a heavy chain constant region.

In vitro: The term "in vitro" as used herein refers to events that occur in an artificial environment, e.g., in a test tube or reaction vessel, in cell culture, etc., rather than within a multi-cellular organism.

In vivo: as used herein refers to events that occur within a multi-cellular organism, such as a human and a non-human animal. In the context of cell-based systems, the term may be used to refer to events that occur within a living cell (as opposed to, for example, in vitro systems).

Isolated: as used herein, refers to a substance and/or entity that has been (1) separated from at least some of the components with which it was associated when initially produced (whether in nature and/or in an experimental setting), and/or (2) designed, produced, prepared, and/or manufactured by the hand of man Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%), about 97%), about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%), about 98%, about 99%, or more than about 99% pure. As used herein, a substance is "pure" if it is substantially free of other components. In some embodiments, as will be understood by those skilled in the art, a substance may still be considered "isolated' or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated' when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated' polypeptide. Alternatively or additionally, in some embodiments, a polypeptide that has been subjected to one or more purification techniques may be considered to be an "isolated' polypeptide to the extent that it has been separated from other components a) with which it is associated in nature; and/or b) with which it was associated when initially produced.

$K_D$: as used herein, refers to the dissociation constant of a binding agent (e.g., an antibody or binding component thereof) from a complex with its partner (e.g., the epitope to which the antibody or binding component thereof binds).

Pharmaceutical composition. As used herein, the term "pharmaceutical composition" refers to a composition in which an active agent is formulated together with one or more pharmaceutically acceptable carriers. In some embodiments, the composition is suitable for administration to a human or animal subject. In some embodiments, the active agent is present in unit dose amount appropriate for administration in a therapeutic regimen that shows a statistically significant probability of achieving a predetermined therapeutic effect when administered to a relevant population.

Polypeptide. The term "polypeptide", as used herein, generally has its art-recognized meaning of a polymer of at least three amino acids. Those of ordinary skill in the art will appreciate that the term "polypeptide" is intended to be sufficiently general as to encompass not only polypeptides having a complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Prevent or prevention: as used herein when used in connection with the occurrence of a disease, disorder, and/or condition, refers to reducing the risk of developing the disease, disorder and/or condition and/or to delaying onset and/or severity of one or more characteristics or symptoms of the disease, disorder or condition. In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition.

Recombinant: as used herein, is intended to refer to polypeptides that are designed, engineered, prepared, expressed, created, manufactured, and/or or isolated by recombinant means, such as polypeptides expressed using a recombinant expression vector transfected into a host cell; polypeptides isolated from a recombinant, combinatorial human polypeptide library; polypeptides isolated from an animal (e.g., a mouse, rabbit, sheep, fish, etc.) that is transgenic for or otherwise has been manipulated to express a gene or genes, or gene components that encode and/or direct expression of the polypeptide or one or more component(s), portion(s), element(s), or domain(s) thereof; and/or polypeptides prepared, expressed, created or isolated by any other means that involves splicing or ligating selected nucleic acid sequence elements to one another, chemically synthesizing selected sequence elements, and/or otherwise generating a nucleic acid that encodes and/or directs expression of the polypeptide or one or more component(s), portion(s), element(s), or domain(s) thereof. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source such as, for example, in the germline of a source organism of interest (e.g., of a human, a mouse, etc.).

Specific binding: As used herein, the term "specific binding" refers to an ability to discriminate between possible binding partners in the environment in which binding is to occur. A binding agent that interacts with one particular target when other potential targets are present is said to "bind specifically" to the target with which it interacts. In some embodiments, specific binding is assessed by detecting or determining degree of association between the binding agent and its partner; in some embodiments, specific binding is assessed by detecting or determining degree of dissociation of a binding agent-partner complex; in some embodiments, specific binding is assessed by detecting or determining ability of the binding agent to compete an alternative interaction between its partner and another entity. In some embodiments, specific binding is assessed by performing such detections or determinations across a range of concentrations.

Subject: As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Therapeutically Effective Amount: As used herein, the term "therapeutically effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, stabilizes one or more characteristics of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. For example, in some embodiments, term "therapeutically effective amount", refers to an amount which, when administered to an individual in need thereof in the context of inventive therapy, will block, stabilize, attenuate, or reverse a cancer-supportive process occurring in said individual, or will enhance or increase a cancer-suppressive process in said individual. In the context of cancer treatment, a "therapeutically effective amount" is an amount which, when administered to an individual diagnosed with a cancer, will prevent, stabilize, inhibit, or reduce the further development of cancer in the individual. A particularly preferred "therapeutically effective amount" of a composition described herein reverses (in a therapeutic treatment) the development of a malignancy such as a pancreatic carcinoma or helps achieve or prolong remission of a malignancy. A therapeutically effective amount administered to an individual to treat a cancer in that individual may be the same or different from a therapeutically effective amount administered to promote remission or inhibit metastasis. As with most cancer therapies, the therapeutic methods described herein are not to be interpreted as, restricted to, or otherwise limited to a "cure" for cancer; rather the methods of treatment are directed to the use of the described compositions to "treat" a cancer, i.e., to effect a desirable or beneficial change in the health of an individual who has cancer. Such benefits are recognized by skilled healthcare providers in the field of oncology and include, but are not limited to, a stabilization of patient condition, a decrease in tumor size (tumor regression), an improvement in vital functions (e.g., improved function of cancerous tissues or organs), a decrease or inhibition of further metastasis, a decrease in opportunistic infections, an increased survivability, a decrease in pain, improved motor function, improved cognitive function, improved feeling of energy (vitality, decreased malaise), improved feeling of well-being, restoration of normal appetite, restoration of healthy weight gain, and combinations thereof. In addition, regression of a particular tumor in an individual (e.g., as the result of treatments described herein) may also be assessed by taking samples of cancer cells from the site of a tumor (e.g., over the course of treatment) and testing the cancer cells for the level of metabolic and signaling markers to monitor the status of the cancer cells to verify at the molecular level the regression of the cancer cells to a less malignant phenotype. For example, tumor regression induced by employing the methods of this invention would be indicated by finding a decrease in any of the pro-angiogenic markers discussed above, an increase in anti-angiogenic markers described herein, the normalization (i.e., alteration toward a state found in normal individuals not suffering from cancer) of metabolic pathways, intercellular signaling pathways, or intracellular signaling pathways that exhibit abnormal activity in individuals diagnosed with cancer. Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

Variant: As used herein in the context of molecules, e.g., nucleic acids, proteins, or small molecules, the term "variant" refers to a molecule that shows significant structural identity with a reference molecule but differs structurally from the reference molecule, e.g., in the presence or absence or in the level of one or more chemical moieties as compared to the reference entity. In some embodiments, a variant also differs functionally from its reference molecule. In general, whether a particular molecule is properly considered to be a "variant" of a reference molecule is based on its degree of structural identity with the reference molecule. As will be appreciated by those skilled in the art, any biological or chemical reference molecule has certain characteristic structural elements. A variant, by definition, is a distinct molecule that shares one or more such characteristic structural elements but differs in at least one aspect from the reference molecule. To give but a few examples, a polypeptide may have a characteristic sequence element comprised of a plurality of amino acids having designated positions relative to one another in linear or three-dimensional space and/or contributing to a particular structural motif and/or biological function; a nucleic acid may have a characteristic sequence element comprised of a plurality of nucleotide residues having designated positions relative to on another in linear or three-dimensional space. In some embodiments, a variant polypeptide or nucleic acid may differ from a reference polypeptide or nucleic acid as a result of one or more differences in amino acid or nucleotide sequence. In some embodiments, a variant polypeptide or nucleic acid shows an overall sequence identity with a reference polypeptide or nucleic acid that is at least 85%, 86%, 87%, 88%, 89%, 90%, 91%, 92%, 93%, 94%, 95%, 96%, 97%, or 99%. In some embodiments, a variant polypeptide or nucleic acid does not share at least one characteristic sequence element with a reference polypeptide or nucleic acid. In some embodiments, a reference polypeptide or nucleic acid has one or more biological activities. In some embodiments, a variant polypeptide or nucleic acid shares one or more of the biological activities of the reference polypeptide or nucleic acid.

Vector: as used herein, refers to a nucleic acid molecule capable of transporting another nucleic acid to which it has been linked. One type of vector is a "plasmic?", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., *Molecular Cloning: A Laboratory Manual* ($2^{nd}$ ed., Cold Spring Harbor Laboratory Press, Cold Spring Harbor, N.Y. (1989)), which is incorporated herein by reference for any purpose.

DETAILED DESCRIPTION OF EXEMPLARY EMBODIMENTS

The present invention relates to anti-AITR antibodies for conversion of a regulatory T cell into a $T_H1$-like cell. For example, engineered antibodies provided herein have been modified to enhance antigen affinity relative to parental antibodies that specifically recognize an epitope within the extracellular domain of human AITR. Specifically, as described herein, the inventors created several exemplary with improved affinity for human AITR. Notably, the exemplary anti-AITR antibodies are cable of converting regulatory T cells ($T_{reg}$ cells) into $T_H1$ cells and regulating the quantity of certain T cell cytokine secretions. Thus the present disclosure provides engineered anti-AITR antibodies with improved properties over reference antibodies, and moreover demonstrates that these antibodies have surprisingly beneficial activity in vitro and in vivo.

AITR

The human activation-inducible tumor necrosis factor receptor (AITR) is a member of the TNFR superfamily, and is also known as GITR (glucocorticoid-induced TNFR-related protein), TNFRSF 18 (TNF receptor superfamily member 18) or CD357 (Kwon et al., *J Biol Chem*, 274: 6056-6061, 1999). AITR is expressed at particularly high levels in $T_{reg}$ cells (regulatory T cells) and activated T cells. AITR refers to any variant, isoform and homolog which is naturally expressed by a cell and may specifically mean, but is not limited to, human AITR. Information on AITR is available from a known database such as NCBI GenBank, and an example thereof may include, but is not limited to, NP_004186. Stimulation of AITR generates a unique intracellular signal which decreases immunosuppressive function of regulatory T cell and promotes $T_{eff}$ cell (effector T cell) activity (Shimizu et al, *Nat Immunol.*, 3:135-142, 2002). Therefore, in view of immuno-oncology, AITR signal increases human immunity against tumors and induces cancer cell death (Sakaguchi, *Cell,* 101:455-458, 2000).

AITR acts as a trimer rather than a single molecule under physiological conditions, and the functional unit of its ligand is a trimer. According to the structural studies on TNFR SF (TNF receptor superfamily) and TNF, three receptor molecules and a TNF trimer—are symmetrically bound and each receptor fragment is bound to grooves of two adjacent TNF. Thus, the contact interface between TNF and TNFR plays a pivotal role in the TNFR-TNF interaction and structure. This functional significance could explain why the amino acid sequence of the contact surface is highly conserved among species, as well as in the TNFR superfamily (Chan et al, *Immunity,* 13:419-422, 2000).

In addition, a cell exposed to a specific condition can progress from a receptor trimer to achieve a tetramer of trimers and then generate a progressive super-signal internally. For this reason, an AITR signal is not a simple transmission of a single on-off signal, but rather a finely-tuned regulation of signal transduction and it becomes an important factor in controlling the anti-cancer capacity of $T_r$ cells (Zhou et al., *PNAS.*, 105:5465-5470, 2008). The complexity and diversity of interactions between TNFR and its ligand, and the numerous available epitopes, enables very precise signal regulation. Therefore, a monoclonal antibody (mAb) that can recognize a particular structural epitope is an optimal candidate for developing a therapeutic agent related to AITR. That is, depending upon where the epitope is on the AITR molecule that is recognized by a particular provided anti-AITR antibody, a particular anti-AITR antibody may mimic a natural ligand of the AITR to varying degrees, for example, activity may be selectively modulated and/or receptor oligomerization may also the adjusted, such that the response through the AITR may be modulated in various ways.

Anti-AITR Antibodies and Fragments Thereof

The present disclosure provides, at least in part, engineered anti-AITR antibodies (also described herein as IFN-γ-inducible Regulatory T cell Convertible anti-cancer mAb (IRTCA) and fragments thereof that exhibit markedly, and unexpectedly, superior characteristics in vitro and/or in vivo. For example, certain provided antibodies have increased affinity relative to reference anti-AITR antibodies.

In some embodiments, an IRTCA antibody or antigen-binding antibody fragment includes 1, 2, or 3 heavy chain CDR sequences that are or include a sequence of selected from SEQ ID NO: 8, 9, 10, 14, 15, 16, 17, 24, and 25. In some embodiments, an IRTCA antibody or antigen-binding antibody fragment includes one or more of: a heavy chain CDR1 that is or includes a sequence selected from SEQ ID NO: 8 and 24, a heavy chain CDR2 that is or includes a sequence selected from SEQ ID NO: 9 and 25 and a heavy chain CDR3 that is or includes a sequence selected from SEQ ID NO: 10, 14, 15, 16, and 17. In some embodiments, an IRTCA antibody or antigen-binding antibody fragment includes each of: a heavy chain CDR1 that is or includes a sequence selected from SEQ ID NO: 8 and 24, a heavy chain CDR2 that is or includes a sequence selected from SEQ ID NO: 9 and 25 and a heavy chain CDR3 that is or includes a sequence selected from SEQ ID NO: 10, 14, 15, 16, and 17.

In some embodiments, an IRTCA antibody or antigen-binding antibody fragment includes 1, 2, or 3 light chain CDR sequences that are or include a sequence selected from SEQ ID NO: 11, 12, 13, and 18. In some embodiments, an IRTCA antibody or antigen-binding antibody fragment includes one or more of: a light chain CDR1 that is or includes a sequence of SEQ ID NO: 11, a light chain CDR2 that is or includes a sequence of SEQ ID NO: 12, and a light chain CDR3 that is or includes a sequence selected from SEQ ID NO: 13 and 18. In some embodiments, an IRTCA antibody or antigen-binding antibody fragment includes each of: a light chain CDR1 that is or includes a sequence of SEQ ID NO: 11, a light chain CDR2 that is or includes a sequence of SEQ ID NO: 12, and a light chain CDR3 that is or includes a sequence selected from SEQ ID NO: 13 and 18.

In some embodiments, an IRTCA antibody or antigen-binding fragment thereof, comprises (a) a heavy chain CDR1 comprising a sequence of SEQ ID NO: 8 or 24, a heavy chain CDR2 comprising a sequence of SEQ ID NO: 9 or 25, and a heavy chain CDR3 comprising at least one sequence selected from SEQ ID NO: 14, 15, 16, and 17; and (b) a light chain CDR1 comprising a sequence of SEQ ID NO: 11, a light chain CDR2 comprising a sequence of SEQ ID NO: 12 and a light chain CDR3 comprising a sequence of SEQ ID NO: 13 or 18, wherein the IRTCA antibody or antigen-binding fragment thereof does not comprise each of a heavy chain CDR1 comprising a sequence of SEQ ID NO: 8, a heavy chain CDR2 comprising a sequence of SEQ ID NO: 9, a heavy chain CDR3 comprising a sequence of SEQ ID NO: 10, a light chain CDR1 comprising a sequence of SEQ ID NO: 11, a light chain CDR2 comprising a sequence of SEQ ID NO: 12 and a light chain CDR3 comprising a sequence of SEQ ID NO: 13.

In some embodiments, an IRTCA antibody or antigen-binding antibody fragment includes substantial homology to an antibody or antibody fragment that includes a heavy chain variable domain that is or includes a sequence selected from SEQ ID NOs: 1, 3, 4, 5, 6, 20, and 21. In some embodiments, an IRTCA antibody or antigen-binding antibody fragment includes a heavy chain variable domain that is or includes a sequence at least 90%, 91%, 92%, 93%, 94%, 95%, 96%, 97%, 98%, 99%, 99.1%, 99.2%, 99.3%, 99.4% or 99.5% identical to a sequence selected from SEQ ID NOs: 1, 3, 4, 5, 6, 20, and 21. In some embodiments, an IRTCA antibody or antigen-binding antibody fragment includes a heavy chain variable domain that is or includes a sequence selected from SEQ ID NOs: 1, 3, 4, 5, 6, 20, and 21.

In some embodiments, an IRTCA antibody or antigen-binding antibody fragment includes substantial homology to an antibody or antibody fragment that includes a light chain variable domain that has or includes a sequence selected from SEQ ID NOs: 2, 7, 22, and 23. In some embodiments, an IRTCA antibody or antigen-binding antibody fragment includes a light chain variable domain that is or includes a sequence at least 90%, 91%, 92%, 93%, 94%, 95%, 96%, 97%, 98%, 99%, 99.1%, 99.2%, 99.3%, 99.4% or 99.5% identical to a sequence selected from SEQ ID NOs: 2, 7, 22, and 23. In some embodiments, an IRTCA antibody or antigen-binding antibody fragment includes a light chain variable domain that is or includes a sequence selected from SEQ ID NOs: 2, 7, 22, and 23.

In some embodiments, an IRTCA antibody or antigen-binding antibody fragment includes substantial homology to an antibody or antibody fragment that includes a heavy chain variable domain that is or includes a sequence selected from SEQ ID NOs: 1, 3, 4, 5, 6, 20, and 21 and a light chain variable domain that is or includes a sequence selected from SEQ ID NOs: 2, 7, 22, and 23. In some embodiments, an IRTCA antibody or antigen-binding antibody fragment includes a heavy chain variable domain that is or includes a sequence at least 90%, 91%, 92%, 93%, 94%, 95%, 96%, 97%, 98%, 99%, 99.1%, 99.2%, 99.3%, 99.4% or 99.5% identical to a sequence selected from SEQ ID NOs: 1, 3, 4, 5, 6, 20, and 21 and a light chain variable domain that is or includes a sequence at least 90%, 91%, 92%, 93%, 94%, 95%, 96%, 97%, 98%, 99%, 99.1%, 99.2%, 99.3%, 99.4% or 99.5% identical to a sequence selected from SEQ ID NOs: 2, 7, 22, and 23. In some embodiments, an IRTCA antibody or antigen-binding antibody fragment includes a heavy chain variable domain that is or includes a sequence selected from SEQ ID NOs: 1, 3, 4, 5, 6, 20, and 21 and a light chain variable domain that is or includes a sequence selected from SEQ ID NOs: 2, 7, 22, and 23.

Amino acid sequences of an IRTCA antibody or antigen-binding fragment binds of the present disclosure may be substituted through conservative substitution. The term "conservative substitution" used herein refers to modification of a polypeptide in which one or more amino acids are substituted with an amino acid having a similar biochemical property so as not to cause the loss of a biological or biochemical function of the corresponding polypeptide. The term "conservative sequence variant" or "conservative amino acid substitution" used herein is the substitution of an amino acid residue with an amino acid residue having a similar side chain. Amino acid residues having a similar side chain are defined in the art. Those residues encompass amino acids with a basic side chain (e.g., lysine, arginine, and histidine), amino acids with an acidic side chain (e.g., aspartic acid and glutamate), amino acids with a non-charged polar side chain (e.g., glycine, asparagine, glutamine, serine, threonine, tyrosine, and cysteine), amino acids with a non-polar side chain (e.g., alanine, valine, leucine, isoleucine, proline, phenylalanine, methionine, and tryptophan), amino acids with a beta-branched side chain (e.g., threonine, valine, and isoleucine) and amino acids with an aromatic side chain (e.g., tyrosine, phenylalanine, tryptophan, and histidine). Therefore, it is expected that the antibody of the present invention can have conservative amino acid substitution, and still ensure an activity.

In some embodiments, an IRTCA antibody or antigen-binding fragment of the present disclosure may include a constant region selected from an IgG1 constant domain, an IgG2 constant domain, an IgG1/IgG2 hybrid constant domain, a human IgG4 constant domain, an IgA constant domain, an IgE constant domain, an IgM constant domain, and an IgD constant domain.

In some embodiments, an IRTCA antibody or antigen-binding fragment of the present disclosure is or includes an IgA, IgD, IgE, IgM, IgG, or variants thereof.

In some embodiments, an IRTCA antibody or antigen-binding fragment includes a light chain constant region. In some embodiments, an IRTCA antibody or antigen-binding fragment includes a kappa (κ) and/or lambda (λ) light chain and/or a variant thereof.

In some embodiments, an IRTCA antibody or antigen-binding fragment is a monoclonal antibody. In some embodiments, an IRTCA antibody or antigen-binding fragment is a Fab fragment, a Fab' fragment, a F(ab')2 fragment, a Fv fragment, a disulfide-bonded Fv fragment, a scFv fragment, a single domain antibody, humabody, nanobody, and/or a diabody. In some embodiments, an IRTCA antibody or antigen-binding fragment is a monovalent antibody. In some embodiments, an IRTCA antibody or antigen-binding fragment is a multivalent antibody. In some embodiments, an IRTCA antibody or antigen-binding fragment is a multi-specific antibody (e.g., a bispecific antibody).

In some embodiments, the present disclosure encompasses methods of modifying the carbohydrate content of an antibody of the disclosure by adding or deleting a glycosylation site. Methods for modifying the carbohydrate content of antibodies are well known in the art and encompassed within the disclosure, see, e.g., U.S. Pat. No. 6,218,149; EP 0 359 096 B1; U.S. Publication No. US 2002/0028486; WO 03/035835; U.S. Publication No. 2003/01 15614; U.S. Pat. Nos. 6,218,149; 6,472,511; all of which are incorporated herein by reference in their entirety. In other embodiments, the present disclosure encompasses methods of modifying the carbohydrate content of an antibody of the present disclosure by deleting one or more endogenous carbohydrate moieties of the antibody.

Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTIl 1), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al, 1999, *Nat. Biotechnol* 17:176-180; Davies et al., 20017 *Biotechnol Bioeng* 74:288-294; Shields et al, 2002, *J Biol Chem* 277:26733-26740; Shinkawa et al, 2003, *J Biol Chem* 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/31 1140A1; PCT WO 02/30954A1; POTIL-LEGENT™ technology (Biowa, Inc. Princeton, N.J.); GLY-COMAB™ glycosylation engineering technology (GLY-CART biotechnology AG, Zurich, Switzerland); each of which is incorporated herein by reference in its entirety. See, e.g., WO 00061739; EA01229125; U S 200301 15614; Okazaki et al, 2004, *JMB*, 336: 1239-49 each of which is incorporated herein by reference in its entirety.

In some embodiments, an IRTCA antibody or antigen-binding fragment of the present disclosure is as an antagonist of human AITR.

In some embodiments, an IRTCA antibody or antigen-binding fragment of the present disclosure binds to a human AITR molecule. In some embodiments, an IRTCA antibody or antigen-binding fragment of the present disclosure specifically binds to a human AITR molecule.

In some embodiments, an IRTCA antibody or antigen-binding fragment binds to a sequence that is or includes that of SEQ ID NO: 19. In some embodiments, an IRTCA antibody or antigen-binding fragment binds to an epitope of IRTCA extracellular domain that is or includes a sequence of SEQ ID NO: 19.

In some embodiments, an IRTCA antibody or antigen-binding fragment of the present disclosure binds to an AITR molecule with a binding affinity ($K_D$) of $1\times10^{-7}$ to $1\times10^{-12}$ M. In some embodiments, an IRTCA antibody or antigen-binding fragment of the present disclosure binds to a human AITR molecule with a binding affinity ($K_D$) of $1\times10^{-8}$ to $1\times10^{-12}$ M. Binding affinity ($K_D$) may be measured, for example, by surface plasmon resonance, for example, using a BIACORE system.

In some embodiments, an IRTCA antibody or antigen-binding fragment of the present disclosure binds to a human AITR molecule or a fragment thereof at a binding affinity ($K_D$) of less than $1.0\times10^{-8}$ M. In some embodiments, an IRTCA antibody or antigen-binding fragment of the present disclosure binds to a human AITR molecule or a fragment thereof at a binding affinity ($K_D$) of less than $1.0\times10^{-9}$ M. In some embodiments, an IRTCA antibody or antigen-binding fragment of the present disclosure binds to a human AITR molecule or a fragment thereof at a binding affinity ($K_D$) of less than $1.0\times10^{-10}$ M.

In some embodiments, an IRTCA antibody or antigen-binding fragment of the present disclosure fails to bind or weakly binds a non-primate AITR polypeptide (e.g., a canine, mouse and rat AITR polypeptide). In some embodiments, an IRTCA antibody or antigen-binding fragment of the present disclosure binds efficiently to human or monkey AITR. This binding affinity suggests that the structure and/or sequence of epitope for a primate AITR antibody may be quite different from canine, mouse and rat.

In some embodiments, an IRTCA antibody or antigen-binding fragment of the present disclosure binds CD4$^+$ T cells expressing human AITR. In some embodiments, an IRTCA antibody or antigen-binding fragment of the present disclosure affects T cell populations. In some embodiments, an IRTCA antibody or antigen-binding fragment of the present disclosure converts regulatory T cells (nT$_{reg}$ cells) to T$_H$1-like (IFN-γ-positive) cells. In some embodiments, an IRTCA antibody or antigen-binding fragment of the present disclosure converts inducible regulatory T cells (iT$_{reg}$ cells) to T$_H$1-like (IFN-γ-positive) cells. In some embodiments, an IRTCA antibody or antigen-binding fragment of the present disclosure converts effector T cells (T$_{eff}$ cells) to T$_H$1 (IFN-γ-positive) cells. In some embodiments, an IRTCA antibody or antigen-binding fragment of the present disclosure decreases a population of regulatory T cells (T$_{reg}$ cells). In some embodiments, an IRTCA antibody or antigen-binding fragment of the present disclosure causes a population of cells to decrease in secretion of a T$_{reg}$ cytokine (e.g., TGF-β).

In some embodiments, an IRTCA antibody or antigen-binding fragment of the present disclosure is characterized by low toxicity (e.g., a low degree of post administration cell death). In some embodiments, an IRTCA antibody or antigen-binding fragment of the present disclosure is characterized by low hepatoxicity. In some embodiments, a subject that has been administered an IRTCA antibody or antigen-binding fragment of the present disclosure at a therapeutic dose has levels of one or more of ALT, AST and total bilirubin in a normal range. In some embodiments, an IRTCA antibody or antigen-binding fragment of the present disclosure is characterized by an ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titers in the patient treated (Elliott et al., *Lancet* 344: 1125-1 127 (1994), entirely incorporated herein by reference).

Nucleic Acids

The disclosure provides polynucleotides comprising a nucleotide sequence encoding IRTCA antibodies of the present disclosure and fragments thereof. IRTCA antibodies and fragments thereof as described herein may be produced from nucleic acid molecules using molecular biological methods known to the art. Nucleic acids of the present disclosure include, for example, DNA and/or RNA.

In some embodiments, nucleic acid constructs include regions that encode an IRTCA antibody or fragment thereof (e.g., H1F1, H1F1M69, H1F1M74). In some embodiments, such antibodies or fragments thereof will include $V_H$ and/or $V_L$ regions. An IRTCA antibody or fragment thereof may be identified and/or selected for a desired binding and/or functional properties, and variable regions of said antibody isolated, amplified, cloned and/or sequenced. Modifications may be made to the $V_H$ and $V_L$ nucleotide sequences, including additions of nucleotide sequences encoding amino acids and/or carrying restriction sites, and/or substitutions of nucleotide sequences encoding amino acids. In some embodiments, a nucleic acid sequence may or may not include an intron sequence.

Where appropriate, nucleic acid sequences that encode IRTCA antibodies and fragments thereof (e.g., H1F1, H1F1M69, H1F1M74) may be modified to include codons that are optimized for expression in a particular cell type or organism (e.g., see U.S. Pat. Nos. 5,670,356 and 5,874,304). Codon optimized sequences are synthetic sequences, and preferably encode the identical polypeptide (or a biologically active fragment of a full length polypeptide which has substantially the same activity as the full length polypeptide) encoded by the non-codon optimized parent polynucleotide. In some embodiments, the coding region of the genetic material encoding antibody components, in whole or in part, may include an altered sequence to optimize codon usage for a particular cell type (e.g., a eukaryotic or prokaryotic cell). For example, a coding sequence for a humanized heavy (or light) chain variable region as described herein may be optimized for expression in a bacterial cells. Alternatively, the coding sequence may be optimized for expression in a mammalian cell (e.g., a CHO cell). Such a sequence may be described as a codon-optimized sequence.

Nucleic acid constructs of the present disclosure may be inserted into an expression vector or viral vector by methods known to the art, and nucleic acid molecules may be operably linked to an expression control sequence. A vector comprising any of the above-described nucleic acid molecules, or fragments thereof, is further provided by the present disclosure. Any of the above nucleic acid molecules, or fragments thereof, can be cloned into any suitable vector and can be used to transform or transfect any suitable host. The selection of vectors and methods to construct them are commonly known to persons of ordinary skill in the art and are described in general technical references (see, in general, "Recombinant DNA Part D," *Methods in Enzymology*, Vol. 153, Wu and Grossman, eds., Academic Press (1987)).

In some embodiments, conventionally used techniques, such as, for example, electrophoresis, calcium phosphate precipitation, DEAE-dextran transfection, lipofection, etc. may be used to introduce a foreign nucleic acid (DNA or RNA) into a prokaryotic or eukaryotic host cell. Desirably, a vector may include regulatory sequences, such as transcription and translation initiation and termination codons, which are specific to the type of host (e.g., bacterium, fungus, plant or animal) into which the vector is to be introduced, as appropriate and taking into consideration whether the vector is DNA or RNA. In some embodiments, a vector comprises regulatory sequences that are specific to the genus of the host. Preferably, a vector comprises regulatory sequences that are specific to the species of the host.

In addition to the replication system and the inserted nucleic acid, a nucleic acid construct can include one or more marker genes, which allow for selection of transformed or transfected hosts. Marker genes include biocide resistance, e.g., resistance to antibiotics, heavy metals, etc., complementation in an auxotrophic host to provide protrophy, and the like.

Suitable vectors include those designed for propagation and expansion or for expression or both. For example, a cloning vector is selected from the group consisting of the pUC series, the pBluescript series (Stratagene, La Jolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), XEMBL4, and λNMI149, also can be used. Examples of plant expression vectors include pBI110, pBI101.2, pBI101.3, pBI121 and pBIN19 (Clontech). Examples of animal expression vectors include pEUK-Cl, pMAM and pMAMneo (Clontech). The TOPO cloning system (Invitrogen, Carlsbad, Calif.) also can be used in accordance with the manufacturer's recommendations.

An expression vector can comprise a native or nonnative promoter operably linked to an isolated or purified nucleic acid molecule as described above. Selection of promoters, e.g., strong, weak, inducible, tissue-specific and developmental-specific, is within the skill in the art. Similarly, combining of a nucleic acid molecule, or fragment thereof, as described above with a promoter is also within the skill in the art.

Suitable viral vectors include, for example, retroviral vectors, parvovirus-based vectors, e.g., adeno-associated virus (AAV)-based vectors, AAV-adenoviral chimeric vectors, and adenovirus-based vectors, and lentiviral vectors, such as Herpes simplex (HSV)-based vectors. These viral vectors can be prepared using standard recombinant DNA techniques described in, for example, Sambrook et al., *Molecular Cloning, a Laboratory Manual, 2d edition*, Cold Spring Harbor Press, Cold Spring Harbor, N.Y. (1989); and Ausubel et al., *Current Protocols in Molecular Biology*, Greene Publishing Associates and John Wiley & Sons, New York, N.Y. (1994).

A retroviral vector is derived from a retrovirus. Retrovirus is an RNA virus capable of infecting a wide variety of host cells. Upon infection, the retroviral genome integrates into the genome of its host cell and is replicated along with host cell DNA, thereby constantly producing viral RNA and any nucleic acid sequence incorporated into the retroviral genome. As such, long-term expression of a therapeutic factor(s) is achievable when using retrovirus. Retroviruses contemplated for use in gene therapy are relatively nonpathogenic, although pathogenic retroviruses exist. When employing pathogenic retroviruses, e.g., human immunodeficiency virus (HIV) or human T-cell lymphotrophic viruses (HTLV), care must be taken in altering the viral genome to eliminate toxicity to the host. A retroviral vector additionally can be manipulated to render the virus replication-deficient. As such, retroviral vectors are considered particularly useful for stable gene transfer in vivo. Lentiviral vectors, such as HIV-based vectors, are exemplary of retroviral vectors used for gene delivery. Unlike other retroviruses, HIV-based vectors are known to incorporate their passenger genes into non-dividing cells and, therefore, can be of use in treating persistent forms of disease.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

In some embodiments, nucleic acids and vectors of the present disclosure may be isolated and/or purified. The present disclosure also provides a composition comprising an above-described isolated or purified nucleic acid molecule, optionally in the form of a vector. Isolated nucleic acids and vectors may be prepared using standard techniques known in the art including, for example, alkali/SDS treatment, CsCl binding, column chromatography, agarose gel electrophoresis and other techniques well known in the art. The composition can comprise other components as described further herein.

In some embodiments, nucleic acid molecules are inserted into a vector that is able to express an IRTCA antibody or fragment thereof when introduced into an appropriate host cell. Appropriate host cells include, but are not limited to, bacterial, yeast, insect, and mammalian cells. Exemplary host cells include prokaryotes (e.g., E. coli) and eukaryotes (e.g., a COS or a CHO cell). Mammalian host cells that could be used include human HeLa, HEK293, H9 and Jurkat cells, mouse NIH3T3 and C127 cells, Cos 1, Cos 7 and CV 1, quail QC1-3 cells, mouse L cells and Chinese hamster ovary (CHO) cells (e.g., DG44 cells). In some embodiments, a mammalian host cell suitable for the expression of the antibody may be a Chinese Hamster Ovary (CHO) cell (for example, including DHFR-CHO cells used along with a DHFR-selectable marker), an NSO myeloma cell, a COS cell or an SP2 cell. In some embodiments the host cell is selected from the group consisting of E. coli, P. pastoris, Sf9, COS, HEK293, Expi293, CHO-S, CHO-DG44, CHO-K1 and a mammalian lymphocyte.

Any method(s) known to one skilled in the art for the insertion of DNA fragments into a vector may be used to construct expression vectors encoding an IRTCA antibody or fragment thereof of the present disclosure under control of transcriptional/translational control signals. These methods may include in vitro recombinant DNA and synthetic techniques and in vivo recombination (See, e.g., Ausubel, supra; or Sambrook, supra).

Production of Antibodies

Antibodies and antigen-binding fragments of the present invention may be prepared and/or purified by any technique known in the art, which allows for the subsequent formation of a stable antibody or antibody fragment.

A nucleic acid encoding IRTCA antibody and/or antigen-binding fragment of the present disclosure may be easily isolated and sequenced by conventional procedures. For example, an oligonucleotide primer designed to specifically amplify corresponding heavy chain and light chain-coding regions from a hybridoma or phage template DNA may be used. Isolated nucleic acids may be inserted into an expression vector, and then desired monoclonal antibodies may be produced from a suitable host cell (that is, transformant) transformed by introducing the expression vector to the host cell. In some embodiments, a method for preparing an IRTCA antibody and/or antigen-binding fragment of the present disclosure may include amplifying an expression vector including a nucleic acid encoding the antibody, but is not limited thereto.

In some embodiments, a host cell is eukaryotic host cell, including, for example, yeast, higher plant, insect and mammalian cells. Depending upon the host employed in a recombinant production procedure, antibodies and antibody fragments of the present disclosure can be glycosylated or can be non-glycosylated. In some embodiments, a recombinant expression vector encoding an IRTCA antibody and/or antigen-binding fragment of the present disclosure is introduced into a mammalian host cell and an antibody may be prepared by culturing the host cell for a sufficient time to express the antibody. In some embodiments, a mammalian host cell is cultured for a sufficient time to secrete an antibody or antibody fragment of the present disclosure in a culture medium.

In some embodiments, an expressed antibody of the present disclosure may be uniformly purified after being isolated from the host cell. Isolation and/or purification of an antibody of the present disclosure may be performed by a conventional method for isolating and purifying a protein. For example, not wishing to be bound by theory, an IRTCA antibody and/or antigen-binding fragment of the present disclosure can be recovered and purified from recombinant cell cultures by well-known methods including, but not limited to, protein A purification, protein G purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., chapters 1, 4, 6, 8, 9, and 10, each entirely incorporated herein by reference. In some embodiments, an antibody of the present disclosure may be isolated and/or purified by additionally combining filtration, superfiltration, salting out, dialysis, etc.

Purified IRTCA antibodies and/or antigen-binding fragments of the present disclosure can be characterized by, for example, ELISA, ELISPOT, flow cytometry, immunocytology, BIACORE™ analysis, SAPIDYNE KINEXA™ kinetic exclusion assay, SDS-PAGE and Western blot, or by HPLC analysis as well as by a number of other functional assays disclosed herein.

Therapeutic Applications

The present disclosure encompasses a recognition that engineered antibodies and antigen-binding fragments may be useful for diagnosis, prevention, and/or treatment of certain diseases such as, for example, cancer. Any of the IRTCA antibodies or antigen-binding fragments provided herein may be used in therapeutic methods. For example, an IRTCA antibody or antigen-binding fragment of the present disclosure can be used as immunotherapeutic agents, for example in the treatment of a malignant disease (e.g., cancer).

The present disclosure provides methods for treating and/or preventing a malignant disease, said methods including administering an IRTCA antibody or antigen-binding fragment of the present disclosure to a subject. Methods for modulating or treating at least one malignant disease in a cell, tissue, organ, animal or patient, include, but are not limited to, cancer.

Cancer treatments in the context of the present disclosure may be mediated through increasing $T_H1$-like cells and associated cytokines (e.g., IFN-γ). $T_H1$ cells that secrete IFN-γ are known to mediate immune responses to intracellular pathogens and to prevent tumor-related cancers Inflammation caused by $T_H1$ cells in tumors is known to not stimulate, but rather to prevent cancers (Haabeth O A et al, *Nat Commun*, 2:240, 2011). In tumors, $T_{reg}$ cells promotes local tumor growth. Therefore, it is considered to be an important part for cancer treatment to down-regulate regulatory T cells in a tumor (Liu Z et al, *J Immunol*, 182(10): 6160-7, 2009). Therefore, conversion of $T_{reg}$ cells into $T_H1$ cells can be very useful prevention or treatment of cancers.

The conversion of $T_{reg}$ cells into $T_H1$ cells is related to the signaling pathway and transcription factors related to $T_H1$ differentiation. In particular, the Foxp3 transcription factor is a specific intracellular marker of $T_{reg}$ cells, and if $T_{reg}$ cells are differentiated to $T_H1$ cells, the intracellular level of Foxp3 is downregulated.

Specifically, it has been demonstrated that binding of an IRTCA antibody or antigen-binding fragment of the present disclosure to human AITR increases conversion of regulatory T cells ($nT_{reg}$ cells), inducible regulatory T cells ($iT_{reg}$ cells), or effector T cells ($T_{eff}$ cells) to $T_H1$-like (IFN-γ-positive) cells. In some embodiments, therapeutic treatment with an IRTCA antibody or antigen-binding fragment of the present disclosure can reduce and/or inhibit growth of cancer cells.

In some embodiments, the present disclosure provides a method for delaying or inhibiting tumor growth, comprising regulation of cytokine secretion in vivo or in vitro by administering an IRTCA antibody or antigen-binding fragment of the present disclosure. In some embodiments, the present disclosure provides a method for reducing tumor burden, comprising regulation of cytokine secretion in vivo or in vitro by administering an IRTCA antibody or antigen-binding fragment of the present disclosure.

In some embodiments, the present disclosure provides a method for treating cancer or tumor by monitoring to a biological subject of cancer or tumor to be treated, comprising: (i) administrating an IRTCA antibody or antigen-binding fragment of the present disclosure to a subject, (ii) separating then isolating a biological sample from the subject, (iii) measuring a secretion amount of INF-γ or TGF-β from the sample and estimating a proportion ratio and (iv) determining a therapeutically effective amount of the antibody or antigen-binding fragment thereof by comparing the control samples which are administrated or not administrated with the IRTCA antibody or antigen-binding fragment thereof.

In some embodiments, the present disclosure provides a method of treating a subject in need thereof, the method comprising a step of administering to the subject a composition that comprises or delivers an IRTCA antibody or antigen-binding fragment of the present disclosure and/or a nucleic acid the same. In some embodiments, a subject has or is at risk for developing cancer. In some embodiments, the present disclosure provides a method for preventing or treating cancer or tumor of a patient, which includes administering a therapeutically effective amount of the IRTCA antibody or the antigen-binding fragment thereof to a patient with cancer or tumor.

In some embodiments, the present disclosure provides a method of inducing an immune response in a subject in need thereof, the method comprising a step of administering to the subject a composition that comprises or delivers an IRTCA antibody or antigen-binding fragment of the present disclosure and/or a nucleic acid the same. In some embodiments, a subject has or is at risk for developing cancer.

In some embodiments, the present disclosure provides a method of enhancing an immune response or increasing the activity of an immune cell in a subject in need thereof, the method comprising a step of administering to the subject a composition that comprises or delivers an IRTCA antibody or antigen-binding fragment of the present disclosure and/or a nucleic acid the same. In some embodiments, a subject has or is at risk for developing cancer.

Cancers suitable for treatment with method of the present disclosure can include, but are not limited to, bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, renal cell carcinoma, glioblastoma, and prostate cancer. In some embodiments, a cancer for treatment with an IRTCA antibody or antigen-binding fragment of the present disclosure may include, but is not limited to, carcinoma, lymphoma (e.g., Hodgkin's and non-Hodgkin's lymphomas), blastoma, sarcoma and leukemia. In some embodiments, cancer may include squamous cell carcinoma, small cell lung cancer, non-small cell lung cancer, lung adenocarcinoma, squamous cell carcinoma of the lung, peritoneal cancer, hepatocellular carcinoma, gastric cancer, pancreatic cancer, glioma, cervical cancer, ovarian cancer, liver cancer, bladder cancer, hepatocellular carcinoma, breast cancer, colon cancer, colorectal cancer, endometrial or uterine carcinoma, salivary carcinoma, kidney cancer, prostate cancer, vulvar cancer, thyroid cancer, liver carcinoma, leukemia and other lymphoproliferative disorders, and various types of head and neck cancer.

A composition including an IRTCA antibody or antigen-binding fragment of the present disclosure may be administered at a pharmaceutically effective amount to treat cancer cells or metastasis thereof, or inhibit the growth of cancer. For use in therapeutic methods, an IRTCA antibody or antigen-binding fragment of the present disclosure would be formulated, dosed, and administered in a fashion consistent with good medical practice. Factors for consideration in this context include the particular disorder being treated, the particular mammal being treated, the clinical condition of the individual patient, the age of the patient, the weight of the patient, the cause of the disorder, the site of delivery of the agent, the method of administration, the scheduling of administration, and other factors known to medical practitioners.

The present disclosure provides high affinity IRTCA antibodies that may have superior properties relative to a reference antibody. The present disclosure encompasses a recognition that these antibodies may have improved ability to induce T cell conversion and/or secretion of cytokines such as IFN-γ. Accordingly, the present disclosure encompasses a recognition that an IRTCA antibody or antigen binding fragment of the present disclosure may be administered a dose lower than reference antibody.

In some embodiments composition that includes an IRTCA antibody or antigen-binding fragment of the present disclosure may be administered to a patient as a bolus or by continuous injection when needed. In some embodiments, bolus administration is of an IRTCA Fab of the present disclosure and may be administered at a dose of 0.0025 to 100 mg/kg, 0.025 to 0.25 mg/kg, 0.010 to 0.10 mg/kg, or 0.10 to 0.50 mg/kg. In the case of the continuous injection, the antibody of the present invention presented as a Fab fragment may be administered at a dose of 0.001 to 100 mg/kg/min, 0.0125 to 1.25 mg/kg/min, 0.010 to 0.75 mg/kg/min, 0.010 to 1.0 mg/kg/min or 0.10 to 0.50 mg/kg/min for 1 to 24 hours, 1 to 12 hours, 2 to 12 hours, 6 to 12 hours, 2 to 8 hours, or 1 to 2 hours. In some embodiment, an antibody of the present disclosure is or comprises a full-length antibody (having a complete constant domain). In some embodiments, a full-length antibody is administered at a dose of approximately 0.01 to 10 mg/kg, 1 to 8 mg/kg, or 2 to 6 mg/kg. In some embodiments, a full-length antibody is administered by injection for 30 to 35 minutes. Administration frequency may vary depending on the severity of a condition. For example, the frequency may be once every 2 to 7 days, once a week, or once every 1, 2, 3 or 4 weeks.

In some embodiments, a composition may be administered to a patient by subcutaneous injection. Specifically, the antibody may be administered to a patient at a dose of 0.1 to 100 mg by subcutaneous injection once every 2 to 7 days, every week, once every two weeks, or every month.

A composition including an IRTCA antibody or antigen-binding fragment of the present disclosure may be administered to a subject who has been administered or will be administered one or more additional anticancer therapies selected from ionizing radiation, a chemotherapeutic agent, an antibody agent, and a cell-based therapy, such that the subject receives treatment with both. In some embodiments, the one or more additional anticancer therapies comprise an immune checkpoint inhibitor, IL-12, GM-CSF, an anti-CD4 agent, cisplatin, fluorouracil, doxorubicin, irinotecan, paclitaxel, indoleamine 2,3-dioxygenase-1 (IDO1) inhibitor or cyclophosphamide.

Various embodiments of the present invention may also be useful for determining an advantageous dosing regimen for one or more provided IRTCA antibodies and/or antigen binding fragments thereof, nucleic acid molecules, recombinant vectors, and/or host cells. For example, in some embodiments, the present invention provides methods of determining a dose of an IRTCA antibody or antigen binding fragment thereof for therapeutic treatment of a subject in need thereof, the method including the steps of: (a) providing or obtaining a measurement of secreted IFN-γ in a biological sample from the subject, wherein the subject has been administered a composition that comprises or delivers an amount of a provided IRTCA antibody or antigen-binding fragment thereof, and (b) comparing the measurement of secreted IFN-γ to a reference value, wherein if the measurement of secreted IFN-γ is higher or lower than the reference value, adjusting the amount of the IRTCA antibody or antigen binding fragment thereof to be administered, thereby determining a dose for therapeutic treatment of a subject.

In some embodiments, a reference value may be a level of IFN-γ in a biological sample from the subject prior to administration of the provided IRTCA antibody or antigen-binding fragment thereof. In some embodiments, if a measured amount of secreted IFN-γ in a biological sample from the subject is higher than a reference value, then treatment is maintained at substantially the same level given previously. In some embodiments, if a measured amount of secreted IFN-γ in a biological sample from the subject is higher than a reference value, then the next treatment is given at a lower dose than the previous treatment. In some embodiments, if a measured amount of secreted IFN-γ in a biological sample from the subject is higher than a reference value, then treatment is ceased for a period of time. In some embodiments, if a measured amount of secreted IFN-γ in a biological sample from the subject is substantially the same as or lower than a reference value, then the next treatment is given at a higher dose than the previous treatment.

By way of additional example, in some embodiments, the present invention provides methods of determining a dose of an IRTCA antibody or antigen binding fragment thereof for therapeutic treatment of a subject in need thereof, including the steps of: (a) providing or obtaining a measurement of $T_{reg}$ cell population in a biological sample from the subject, wherein the subject has been administered a composition that comprises or delivers an amount of a provided IRTCA antibody or antigen-binding fragment thereof; and (b) comparing the measurement of $T_{reg}$ cell population to a reference value, wherein if the measurement of $T_{reg}$ cell population is higher or lower than the reference value, adjusting the amount of the IRTCA antibody or antigen binding fragment thereof to be administered, thereby determining a dose for therapeutic treatment of a subject.

In some embodiments, a reference value may be a level of $T_{reg}$ cell population in a biological sample from the subject prior to administration of the provided IRTCA antibody or antigen-binding fragment thereof. In some embodiments, if a measured amount of $T_{reg}$ cell population in a biological sample from the subject is lower than a reference value, then treatment is maintained at substantially the same level given previously. In some embodiments, if a measured amount of $T_{reg}$ cell population in a biological sample from the subject is lower than a reference value, then the next treatment is given at a lower dose than the previous treatment. In some embodiments, if a measured amount of $T_{reg}$ cell population in a biological sample from the subject is lower than a reference value, then treatment is ceased for a period of time. In some embodiments, if a measured amount of $T_{reg}$ cell population in a biological sample from the subject is substantially the same as or higher than a reference value, then the next treatment is given at a higher dose than the previous treatment.

By way of additional example, in some embodiments, the present invention provides methods of determining a dose of an IRTCA antibody or antigen binding fragment thereof for therapeutic treatment of a subject in need thereof, including the steps of: (a) providing or obtaining a measurement of IFN-γ-secreting T cell population in a biological sample from the subject, wherein the subject has been administered a composition that comprises or delivers an amount of a provided IRTCA antibody or antigen-binding fragment thereof; (b) providing or obtaining a measurement of $T_{reg}$ cell population in a biological sample from the subject, wherein the subject has been administered a composition that comprises or delivers an amount of a provided IRTCA antibody or antigen-binding fragment thereof; (c) calculating the ratio of the measurement of IFN-γ-secreting T cell population to the measurement of $T_{reg}$ cell population; and (d) comparing the ratio to a reference value, wherein if ratio is higher or lower than the reference value, adjusting the amount of the IRTCA antibody or antigen binding fragment thereof to be administered, thereby determining a dose for therapeutic treatment of a subject.

In some embodiments, a reference value may be a ratio of a level of IFN-γ-secreting T cell population in a biological sample form a subject to a level of $T_{reg}$ cell population in the same biological sample from the subject prior to administration of the provided IRTCA antibody or antigen-binding fragment thereof. In some embodiments, if a calculated ratio in a biological sample from the subject is higher than a reference value, then treatment is maintained at the same level given previously. In some embodiments, if a calculated ratio in a biological sample from the subject is higher than a reference value, then the next treatment is given at a lower dose than the previous treatment. In some embodiments, if a calculated ratio in a biological sample from the subject is higher than a reference value, then treatment is ceased for a period of time. In some embodiments, if a calculated ratio in a biological sample from the subject is substantially the same as or lower than a reference value, then the next treatment is given at a higher dose than the previous treatment.

Compositions

Provided herein, in some embodiments, are compositions comprising antibodies and antigen binding fragments that specifically bind to an epitope of an AITR polypeptide. Compositions of the present disclosure (e.g., compositions that deliver an IRTCA antibody or antibody fragment) may include any suitable and effective amount of a composition for use in delivering a provided IRTCA antibody or antibody fragment to a cell, tissue, organ, animal or patient in need of such modulation, treatment or therapy. Also provided herein are compositions that include converted cell populations (e.g., to $T_H1$-like cells) that have been generated via a method of the present disclosure (e.g., a method that includes a step contacting a cell with an IRTCA antibody or antibody fragment).

Compositions of the present disclosure include pharmaceutical compositions that include an IRTCA antibody or antigen-binding fragment disclosed herein and/or a cell population obtained by a method disclosed herein. In some embodiments, a pharmaceutical composition can include a buffer, a diluent, an excipient, or any combination thereof. In some embodiments, a composition, if desired, can also contain one or more additional therapeutically active substances.

In some embodiments, an IRTCA antibody, antigen-binding fragment and/or cell population of the present disclosure are suitable for administration to a mammal (e.g., a human) Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

In some embodiments, provided compositions may be formulated for parenteral administration. For example, a pharmaceutical composition provided herein may be provided in a sterile injectable form (e.g., a form that is suitable for subcutaneous injection or intravenous infusion). For example, in some embodiments, a pharmaceutical compositions is provided in a liquid dosage form that is suitable for injection. In some embodiments, a pharmaceutical composition is provided as powders (e.g., lyophilized and/or sterilized), optionally under vacuum, which can be reconstituted with an aqueous diluent (e.g., water, buffer, salt solution, etc.) prior to injection. In some embodiments, a pharmaceutical composition is diluted and/or reconstituted in water, sodium chloride solution, sodium acetate solution, benzyl alcohol solution, phosphate buffered saline, etc. In some embodiments, a powder should be mixed gently with the aqueous diluent (e.g., not shaken).

In some embodiments, an IRTCA antibody, antigen-binding fragment, and/or cell population of the present disclosure is formulated with a pharmaceutically acceptable parenteral vehicle. Examples of such vehicles are water, saline, Ringer's solution, dextrose solution, and 1-10% human serum albumin. Liposomes and non-aqueous vehicles such as fixed oils can also be used. A vehicle or lyophilized powder can contain additives that maintain isotonicity (e.g., sodium chloride, mannitol) and chemical stability (e.g., buffers and preservatives). In some embodiments, a formulation is sterilized by known or suitable techniques.

Formulations of the pharmaceutical compositions described herein may be prepared by any method known or hereafter developed in the art of pharmacology. In general, such preparatory methods include the step of bringing the active ingredient into association with a diluent or another excipient and/or one or more other accessory ingredients, and then, if necessary and/or desirable, shaping and/or packaging the product into a desired single- or multi-dose unit.

In some embodiments, a pharmaceutical composition including an IRTCA antibody, antigen-binding fragment, and/or cell population of the present disclosure can be included in a container for storage or administration, for example, an vial, a syringe (e.g., an IV syringe), or a bag (e.g., an IV bag). A pharmaceutical composition in accordance with the present disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. The examples below describe, in part, dosing of exemplary IRTCA antibodies to rodents and monkeys. Standard methods are known in the art of how to scale dosing in animal systems. See, for example, *J Basic Clin Pharm.* March 2016-May 2016; 7(2): 27-31, which is incorporated herein by reference in its entirety. By way of example, the composition may comprise between 0.1% and 100% (w/w) active ingredient.

In some embodiments, a composition comprises or delivers an IRTCA antibody or antigen-binding fragment of the present disclosure at a dose of 0.01 mg/kg to 100 mg/kg. In some embodiments, a composition comprises or delivers an IRTCA antibody or antigen-binding fragment at a dose in an amount within a range bounded by a lower limit and an upper limit, the upper limit being larger than the lower limit. In some embodiments, the lower limit may be about 0.01 mg/kg, 0.025 mg/kg, 0.05 mg/kg, 0.075 mg/kg, 0.1 mg/kg, 0.25 mg/kg, 0.5 mg/kg, 0.75 mg/kg, 1 mg/kg, 2 mg/kg, 3 mg/kg, 4 mg/kg, 5 mg/kg, 8 mg/kg, 10 mg/kg, 20 mg/kg, 25 mg/kg, 30 mg/kg, 40 mg/kg, 50 mg/kg, 50 mg/kg, 70 mg/kg, 80 mg/kg, or 90 mg/kg. In some embodiments, the upper limit may be about 0.025 mg/kg, 0.05 mg/kg, 0.075 mg/kg, 0.1 mg/kg, 0.25 mg/kg, 0.5 mg/kg, 0.75 mg/kg, 1 mg/kg, 2 mg/kg, 3 mg/kg, 4 mg/kg, 5 mg/kg, 8 mg/kg, 10 mg/kg, 20 mg/kg, 25 mg/kg, 30 mg/kg, 40 mg/kg, 50 mg/kg, 50 mg/kg, 70 mg/kg, 80 mg/kg, 90 mg/kg, or 100 mg/kg.

A pharmaceutical composition may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this disclosure.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by the United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. Excipients such as cocoa butter and suppository waxes, coloring agents, coating agents, sweetening, flavoring, and/or perfuming agents can be present in the composition, according to the judgment of the formulator.

In some embodiments, a provided pharmaceutical composition comprises one or more pharmaceutically acceptable excipients (e.g., preservative, inert diluent, dispersing agent, surface active agent and/or emulsifier, buffering agent, etc.). In some embodiments, a pharmaceutical composition comprises one or more preservatives. In some embodiments, pharmaceutical compositions comprise no preservative.

In some embodiments, a composition including an IRTCA antibody or antigen-binding fragment of the present disclosure is stably formulated. In some embodiments, a stable formulation of an IRTCA antibody or antigen-binding fragment of the present disclosure may comprise a phosphate buffer with saline or a chosen salt, as well as preserved solutions and formulations containing a preservative as well as multi-use preserved formulations suitable for pharmaceutical or veterinary use. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3, 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

In some embodiments, a pharmaceutical composition is provided in a form that can be refrigerated and/or frozen. In some embodiments, a pharmaceutical composition is provided in a form that cannot be refrigerated and/or frozen. In some embodiments, reconstituted solutions and/or liquid dosage forms may be stored for a certain period of time after reconstitution (e.g., 2 hours, 12 hours, 24 hours, 2 days, 5 days, 7 days, 10 days, 2 weeks, a month, two months, or longer). In some embodiments, storage of antibody compositions for longer than the specified time results in antibody degradation.

Liquid dosage forms and/or reconstituted solutions may comprise particulate matter and/or discoloration prior to administration. In some embodiments, a solution should not be used if discolored or cloudy and/or if particulate matter remains after filtration.

General considerations in the formulation and/or manufacture of pharmaceutical agents may be found, for example, in Remington: The Science and Practice of Pharmacy 21st ed., Lippincott Williams & Wilkins, 2005.

Kits

The present disclosure further provides pharmaceutical packs and/or kits comprising one or more containers filled with at least one IRTCA antibody or antibody fragment as described herein. Kits may be used in any applicable method, including, for example, therapeutic methods, diagnostic methods, cell proliferation and/or isolation methods, etc. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

In some embodiments, a kit may include one or more reagents for detection (e.g., detection of an IRTCA antibody or antibody fragment). In some embodiments, a kit may include an IRTCA antibody or antibody fragment in a detectable form (e.g., covalently associated with detectable moiety or entity).

In some embodiments, an IRTCA antibody or antibody fragment as provided herein may be included in a kit used for treatment of subjects. In some embodiments, an IRTCA antibody or antibody fragment as provided herein may be included in a kit used for conversion of T cells (e.g., regulatory T cells converted to $T_H1$-like (IFN-γ-positive) cells).

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments. However, the following examples are merely provided to illustrate the present invention, but the scope of the present invention is not limited to the following examples.

EXAMPLES

The present disclosure provides, at least in part, novel IRTCA antibodies and fragments thereof with high affinity toward hAITR, wherein binding of an exemplary IRTCA antibody to a T cell expressing hAITR on a T cell, can lead to immunity enhancement and/or anti-cancer activity. Generation and characterization of novel IRTCA antibodies and fragments thereof is described in further detail in the following examples.

Example 1: Cloning of Anti-AITR Antibodies, Including IRTCA-A

This example describes the production of exemplary IRTCA antibodies. A monoclonal antibody (mAb), IRTCA-A, was used as a template, and each heavy chain and light chain variable region gene and the human constant region gene were amplified using polymerase chain reaction (PCR) before treatment with the Sfi-1 restriction enzyme, ligation, insertion into an expression vector. The pelB leader sequence that mediates transfer to a bacterial periplasmic region was inserted upstream of a heavy chain gene and a signal peptide that induces secretion was inserted upstream of a light chain gene for modification so that expression in E. coli might result in localization to the periplasmic region. The specific sequence of the IRTCA variable region was connected to a human kappa chain for the light chain and connected with a human constant region for the heavy chain to carry out cloning so that structural identity with natural Fab might be maintained (see, FIG. 1, panel a). The amino acid sequence of the AITR (hGITR) derived epitope used in the present invention is 'HCGDPCCTTC (SEQ ID NO: 19). This corresponds to the $55^{th}$-$64^{th}$ amino acids of the extracellular domain in AITR (hGITR).

Insertion of Amber Stop Codon in the Variable Regions of Parental IRTCA-A

The technique of site-directed mutagenesis on one nucleotide was used to generate amber stop codons in the immediately upstream of the CDR3 region of the parental IRTCA-A variable region (that is, IRTCA-A: TGC->TGA). In IRTCA-A, the cysteine at position 89 in the parental form of the light chain and the cysteine at position 96 in the parental form of the heavy chain were mutated to a stop codon to build a CDR3 randomized library. Selection of a parental sequence was prevented to lower the frequency of gene expression and to prevent contamination so that screening might be efficiently achieved for designing (see, FIG. 1, panel b).

Example 2: Building of Anti-AITR Antibody Library and Fabrication of Anti-AITR Antibody Fabs comprising the parental base sequence of IRTCA-A, in which a stop codon was inserted, were used as templates and randomized PCR was performed to afford random mutation in the CDR3 region (FIG. 2).

While sequence changes in CDR3 do not result in significant changes in the antigenic determinant of an antibody but increase variation, the possibility of changing the epitope of the antibody to be selected also increases in proportion with the number of amino acids with induced mutation. Therefore, mutation rates of LCDR3-R and HCDR3-F primer primers were modulated during the design of randomized PCR so that original epitopes recognized by IRTCA-A might not be modified and that the mutation rate of each amino acid sequence might be 70% or less. For the light chain, the splicing PCR technique was used to fix the heavy chain sequence and fragment 1 (350 bp) amplified with omp primer and LCDR3-R and fragment 2 (−1200 bp) amplified with LFR4-R and dp seq. were used as templates to obtain fragment 3 of approximately 1500 bp which had random mutation in the light chain CDR3 region amplified with omp primer and dp seq. (see, FIG. 2, panel a). For the heavy chain, following the amplification conducted by the same mode (see, FIG. 2, panel b) the resulting base sequence was verified and then cloned into an expression vector to achieve expression on phage surface. That is, in order to minimize influence on the antibody structure, under the condition that the length of the CDR3 (CDR-L3) region in a light variable chain and the length of the CDR3 (CDR-H3) region in a heavy chain were maintained. The frequency of the clone which incurred mutation was measured and found to be as high as approximately 86%. In conclusion, a phage display library was built wherein diversity of light chain and heavy chain arrived $1\times10^8$ or higher (see, Table 1).

Table 1 shows variation of the phage library which expresses Fab of IRTCA-A. That is, "Library diversity=transformant number×normal Fab cloning rate" may be used to calculate diversity.

TABLE 1

| | Transformant number | Intended Fab cloning % rate | Diversity |
|---|---|---|---|
| IRTCA-A Light Chain | $5.0 \times 10^8$ | 77.5 | $3.8 \times 10^8$ |
| IRTCA-A Heavy Chain | $5.0 \times 10^8$ | 86.3 | $4.8 \times 10^8$ |

On the other hand, in order to generate the anti-AITR antibody in a bivalent form, Fab (VH (heavy chain variable region) and VL (light chain variable region)) obtained from the phage display library was connected with the CH (heavy chain variable region) and CL (light chain variable region) genes and then inserted in the protein expression vector for animal cells. The vector into which the anti-AITR antibody gene was inserted was transfected into animal cell strains including HEK293 and/or CHO cells, and a protein A or protein G column was used to carry out purification from culture supernatant solution, which resulted in preparation of the anti-human AITR monoclonal antibody in the bivalent form (data not shown).

Example 3: Selection of the Anti-AITR Antibody with Improved Affinity

The fabricated Fab (fragment antigen-binding) library was subject to a selection process with the fixed GST-AITR antigen and repeated four times. For IRTCA-A, after repetitive panning was performed, 17 heavy chain clones and 33 light chain clones with strong positive signals were acquired. Since increase in affinity reduces $K_{off}$ values, 47 Fabs were selected from a total of 50 clones and purified to measure $K_{off}$ based on SPR (surface plasmon resonance) (see, FIG. 3 and FIG. 4). For the 5 (4 heavy chains, 1 light chain) Fabs with the decreased values, their $K_D$ values were measured with SPR (surface plasmon resonance) (see, Table 2).

As indicated in Table 3, it was subsequently found that all of the final IRTCA-A Fabs selected had increased affinity and that the rate of increase varied by 8-44 fold.

Table 2 lists $K_{off}$ and $K_D$ measurement values for five selected species of IRTCA-A Fab against the AITR antigen.

TABLE 2

| Clone | $K_{off}$ | $K_D$ |
|---|---|---|
| Parental IRTCA-A | $1.34 \times 10^{-3}$-$1.99 \times 10^{-3}$ | $1.14 \times 10^{-7}$ |
| IRTCA-A1 (Clone L1E9) | $7.21 \times 10^{-4}$ | $1.39 \times 10^{-8}$ |
| IRTCA-A10 (Clone H1A10) | $5.64 \times 10^{-4}$ | $1.36 \times 10^{-8}$ |
| IRTCA-A12 (Clone H2A10) | $3.91 \times 10^{-4}$ | $4.13 \times 10^{-9}$ |
| IRTCA-A14 (Clone H2F8) | $3.45 \times 10^{-4}$ | $3.79 \times 10^{-9}$ |
| IRTCA-A15 (Clone H1F1) | $6.55 \times 10^{-4}$ | $2.57 \times 10^{-9}$ |

Table 3 lists binding affinity measurements and fold ratio of 5 species of IRTCA-A Fab against the AITR antigen ($K_D$=$K_0$ff/$_{Ko}$n, $K_D$ ratio=mutant $K_D$/IRTCA-A $K_D$).

TABLE 3

| Clone | $K_{on}$ (M$^{-1}$s$^{-1}$) | $K_{off}$ (s$^{-1}$) | $K_A$ (M$^{-1}$) | $K_D$ (M) | Chi$^2$ | $K_D$ Ratio |
|---|---|---|---|---|---|---|
| parental IRTCA-A | $1.17 \times 10^4$ | $1.34 \times 10^{-3}$ | $8.74 \times 10^6$ | $1.14 \times 10^{-7}$ | 0.635 | 1.0 |
| H1A10 | $4.15 \times 10^4$ | $5.65 \times 10^{-4}$ | $7.34 \times 10^7$ | $1.36 \times 10^{-8}$ | 0.399 | 8.38 |
| H2A10 | $6.97 \times 10^4$ | $2.88 \times 10^{-4}$ | $2.42 \times 10^8$ | $4.13 \times 10^{-9}$ | 0.419 | 27.6 |
| H1F1 | $1.30 \times 10^5$ | $3.34 \times 10^{-4}$ | $3.90 \times 10^8$ | $2.57 \times 10^{-9}$ | 0.934 | 44.4 |
| H2F8 | $7.11 \times 10^4$ | $2.70 \times 10^{-4}$ | $2.64 \times 10^8$ | $3.79 \times 10^{-9}$ | 1.23 | 30.1 |
| L1E9 | $2.96 \times 10^4$ | $4.12 \times 10^{-4}$ | $7.18 \times 10^7$ | $1.39 \times 10^{-8}$ | 0.641 | 8.2 |

Table 4 lists the SEQ ID NOs associated with the amino acid sequences of the heavy chain variable regions, light chain variable regions, heavy chain CDRs and light chain CDRs for the clone antibodies in Table 2 to Table 3.

Table 5 lists the amino acid sequences of the heavy chain variable regions, light chain variable regions, heavy chain CDRs and light chain CDRs for the clone antibodies in Table 2 to Table 3.

TABLE 4

| Clone | IRTCA designation | Heavy Chain Variable Region SEQ ID NO: | Light Chain Variable Region SEQ ID NO: | HCDR1 SEQ ID NO: | HCDR2 SEQ ID NO: | HCDR3 SEQ ID NO: | LCDR1 SEQ ID NO: | LCDR2 SEQ ID NO: | LCDR3 SEQ ID NO: |
|---|---|---|---|---|---|---|---|---|---|
|  | Parental IRTCA-A | 1 | 2 | 8 | 9 | 10 | 11 | 12 | 13 |
| L1E9 | IRTCA-A1 | 1 | 7 | 8 | 9 | 10 | 11 | 12 | 18 |
| H1A10 | IRTCA-A10 | 3 | 2 | 8 | 9 | 14 | 11 | 12 | 13 |
| H2A10 | IRTCA-A12 | 4 | 2 | 8 | 9 | 15 | 11 | 12 | 13 |
| H2F8 | IRTCA-A14 | 6 | 2 | 8 | 9 | 17 | 11 | 12 | 13 |
| H1F1 | IRTCA-A15 | 5 | 2 | 8 | 9 | 16 | 11 | 12 | 13 |

TABLE 5

| Clone Region | Variable | Amino Acid Sequence | SEQ. ID. |
|---|---|---|---|
| Parental IRTCA-A | Heavy Chain | QVQLVQSGTQVKMPGASVKVSCKASGYTFDDYGIGWVRQAPGQGLE WMGWISPYTHRTNSSPKLQDRVTMTTDTSTSTAYMELRSLRSDDTAVY YCARDGTYYDFWSGYFDNGAFDIWGQGTLVTVSS | 1 |
|  | Light Chain | QSVVTQPPSVSAAPGQKVTISCSGSTSNIGNNYVSWYQQLPGTAPKLLIY DNYKRPSGIPDRFSGSKSGTSATLGITGLRTGDEADYFCGTWDSSLNAW VFGGGTKLTVL | 2 |
| IRTCA-A1 (L1E9) | Heavy Chain | QVQLVQSGTQVKMPGASVKVSCKASGYTFDDYGIGWVRQAPGQGLE WMGWISPYTHRTNSSPKLQDRVTMTTDTSTSTAYMELRSLRSDDTAVY YCARDGTYYDFWSGYFDNGAFDIWGQGTLVTVSS | 1 |
|  | Light Chain | QSVVTQPPSVSAAPGQKVTISCSGSTSNIGNNYVSWYQQLPGTAPKLLIY DNYKRPSGIPDRFSGSKSGTSATLGITGLRTGDEADYFCGSWESGSNAY KFGGGTKLTVL | 7 |
| IRTCA-A10 (H1A10) | Heavy Chain | QVQLVQSGTQVKMPGASVKVSCKASGYTFDDYGIGWVRQAPGQGLE WMGWISPYTHRTNSSPKLQDRVTMTTDTSTSTAYMELRSLRSDDTAVY YCARDGTYYDFWSGYFDNAAFDSWGQGTLVTVS | 3 |
|  | Light Chain | QSVVTQPPSVSAAPGQKVTISCSGSTSNIGNNYVSWYQQLPGTAPKLLIY DNYKRPSGIPDRFSGSKSGTSATLGITGLRTGDEADYFCGTWDSSLNAW VFGGGTKLTVL | 2 |
| IRTCA-A12 (H2A10) | Heavy Chain | QVQLVQSGTQVKMPGASVKVSCKASGYTFDDYGIGWVRQAPGQGLE WMGWISPYTHRTNSSPKLQDRVTMTTDTSTSTAYMELRSLRSDDTAVY YCARDGTYYDFWSGYFDNATFDFWGQGTLVTVSS | 4 |
|  | Light Chain | QSVVTQPPSVSAAPGQKVTISCSGSTSNIGNNYVSWYQQLPGTAPKLLIY DNYKRPSGIPDRFSGSKSGTSATLGITGLRTGDEADYFCGTWDSSLNAW VFGGGTKLTVL | 2 |

TABLE 5-continued

| Clone Region | Variable | Amino Acid Sequence | SEQ. ID. |
|---|---|---|---|
| IRTCA-A14 (H2F8) | Heavy Chain | QVQLVQSGTQVKMPGASVKVSCKASGYTFDDYGIGWVRQAPGQGLE WMGWISPYTHRTNSSPKLQDRVTMTTDTSTSTAYMELRSLRSDDTAVY YCARDGTYYDFWSGYFDTAAFDIWGQGTLVTVSS | 6 |
| | Light Chain | QSVVTQPPSVSAAPGQKVTISCSGSTSNIGNNYVSWYQQLPGTAPKLLIY DNYKRPSGIPDRFSGSKSGTSATLGITGLRTGDEADYFCGTWDSSLNAW VFGGGTKLTVL | 2 |
| IRTCA-A15 (H1F1) | Heavy Chain | QVQLVQSGTQVKMPGASVKVSCKASGYTFDDYGIGWVRQAPGQGLE WMGWISPYTHRTNSSPKLQDRVTMTTDTSTSTAYMELRSLRSDDTAVY YCARDGTYYDFWSGYFDNNAFDIWGQGTLVTVSS | 5 |
| | Light Chain | QSVVTQPPSVSAAPGQKVTISCSGSTSNIGNNYVSWYQQLPGTAPKLLIY DNYKRPSGIPDRFSGSKSGTSATLGITGLRTGDEADYFCGTWDSSLNAW VFGGGTKLTVL | 2 |

TABLE 6

| Clone | Variable Region | CDR1 Amino Acid Sequence | SEQ ID NO: | CDR2 Amino Acid Sequence | SEQ ID NO: | CDR3 Amino Acid Sequence | SEQ ID NO: |
|---|---|---|---|---|---|---|---|
| Parental IRTCA-A | Heavy Chain | GYTFDDYG | 8 | ISPYTHRT | 9 | ARDGTYYDFWSGYFDNGAFDI | 10 |
| | Light Chain | TSNIGNNY | 11 | DNY | 12 | GTWDSSLNAWV | 13 |
| IRTCA-A1 (L1E9) | Heavy Chain | GYTFDDYG | 8 | ISPYTHRT | 9 | ARDGTYYDFWSGYFDNGAFDI | 10 |
| | Light Chain | TSNIGNNY | 11 | DNY | 12 | GSWESGSNAYK | 18 |
| IRTCA-A10 (H1A10) | Heavy Chain | GYTFDDYG | 8 | ISPYTHRT | 9 | ARDGTYYDFWSGYFDNAAFDS | 14 |
| | Light Chain | TSNIGNNY | 11 | DNY | 12 | GTWDSSLNAWV | 13 |
| IRTCA-A11 (H2A10) | Heavy Chain | GYTFDDYG | 8 | ISPYTHRT | 9 | ARDGTYYDFWSGYFDNATFDF | 15 |
| | Light Chain | TSNIGNNY | 11 | DNY | 12 | GTWDSSLNAWV | 13 |
| IRTCA-A14 (H2F8) | Heavy Chain | GYTFDDYG | 8 | ISPYTHRT | 9 | ARDGTYYDFWSGYFDTAAFDI | 17 |
| | Light Chain | TSNIGNNY | 11 | DNY | 12 | GTWDSSLNAWV | 13 |
| IRTCA-A15 (H1F1) | Heavy Chain | GYTFDDYG | 8 | ISPYTHRT | 9 | ARDGTYYDFWSGYFDNNAFDI | 16 |
| | Light Chain | TSNIGNNY | 11 | DNY | 12 | GTWDSSLNAWV | 13 |

Example 4: Use of IFN-γ and TGF-β as Biomarkers

The $T_H1$ cell is evaluated to have the most efficient anti-cancer capacity among various $T_H$ (helper T) cell types, and $T_{reg}$ cell and $T_H2$ cell are known to promote tumor formation by creating immunosuppressive environment around tumor. The $T_{reg}$ cell is known to be the suppressor T cell as well and responsible for resistance to auto antigen to suppress autoimmune diseases and excessive immune responses (Sakaguchi et al, *Cell*, 133:775-787, 2008). Accordingly, $T_{reg}$ cells can be useful in treating autoimmune diseases for this reason. On the contrary, it weakens activity of the immune system against tumors cells so that it decreases the anti-cancer capacity of a patient. Nevertheless, some subgroups in the $T_{reg}$ cells whose expression of FoxP3 is unstable may be converted into effector-memory phenotypes (Zhou et al, *Nature immunology*, 10:1000-1007, 2009). In addition, properties of the $T_{reg}$ cell lacking VHL (Von Hippel-Lindau) are not fixed but may undergo changes in a certain immune environment, for example, it can be converted into the $T_{eff}$ cell (effector T cell) which produces IFN-γ (Lee et al., *Immunity*, 42:1062-1074, 2015). Therefore, immunoregulation based on the $T_{reg}$ cell represents the means of effective tumor suppression, and the technology of removing the $T_{reg}$ cell or converting into the $T_{eff}$ cell is the ultimate goal of anti-cancer treatment with immune cell.

IFN-γ is the representative cytokine secreted from T-lymphocyte and natural killer cell (NK cell) and exhibits proliferation and anti-viral activity. It is also an important activator of macrophage and particularly key cytokine which differentiates the $T_H1$ cell from other cell types. Such $T_H1$ cell secretes IFN-γ to stimulate division by itself and has the capacity to differentiate the undifferentiated CD4$^+$ cell ($T_H0$) into the $T_H1$ cell. The differentiated $T_H1$ cell plays the key role in activating cytotoxic T cells, phagocytes and B cells. On the other hand, TGF-β is known to be a very important factor for immunoregulation of the Foxp3$^+$ $T_{reg}$ cell (Maria et al, *Immunity*, 30:626-635, 2009), and in particular, promotes differentiation of the CD4$^+$ T cell into the $T_{reg}$ cell and $T_H17$ cell having immunosuppression capacities (Basso et al, *Cell Res.*, 4:399-41 1, 2009). In the end, the efficiency of an anti-cancer drug can be determined after decrease in the $T_{reg}$ cell secreting TGF-β and increase in $T_H1$ inducing IFN-γ must be relatively evaluated. For this reason measurement of secretion of IFN-γ and TGF-β against certain stimulation may be the optimal standard which can be utilized as the quantitative scale of change in the T cell function.

Thus in order to verify the potential of IFN-γ (interferon gamma) and/or TGF-β (transforming growth factor-beta) to serve as biomarkers and determine the activity of IRTCA-A against the $T_{reg}$ cell, representative $T_{reg}$ cell markers including CD4 and CD25 were used to isolate the CD4$^+$ CD25$^{high}$FOXP3$^+$ $T_{reg}$ cell from peripheral blood mononuclear cells (PBMCs) and then to measure cytokine secretion by the monoclonal antibody (mAb).

Figure 5:
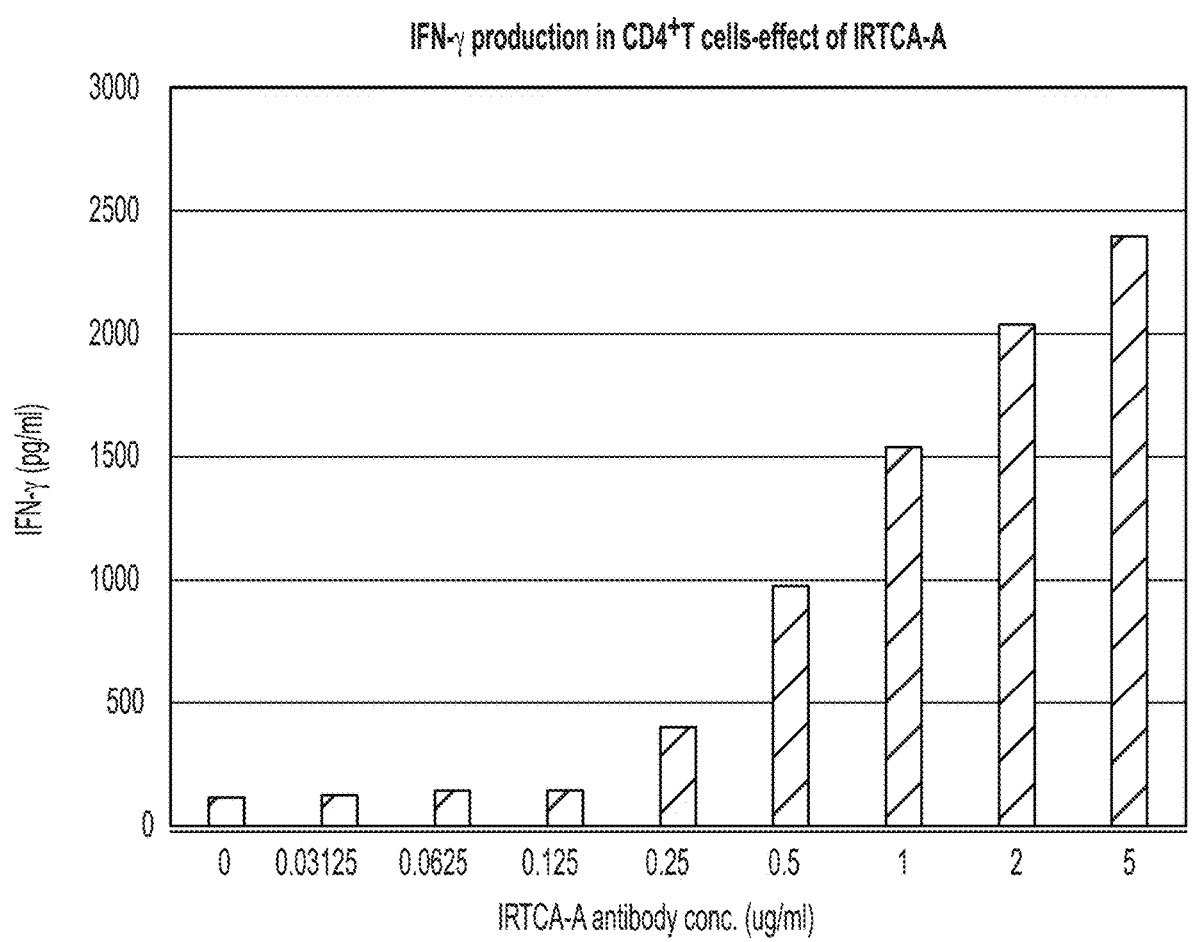
FIG. 5 shows a graph of secretion of cytokine IFN-γ by IRTCA-A in CD4$^+$ T cells. IRTCA-A induces IFN-γ secretion in a dose dependent manner.
Figure 6A:
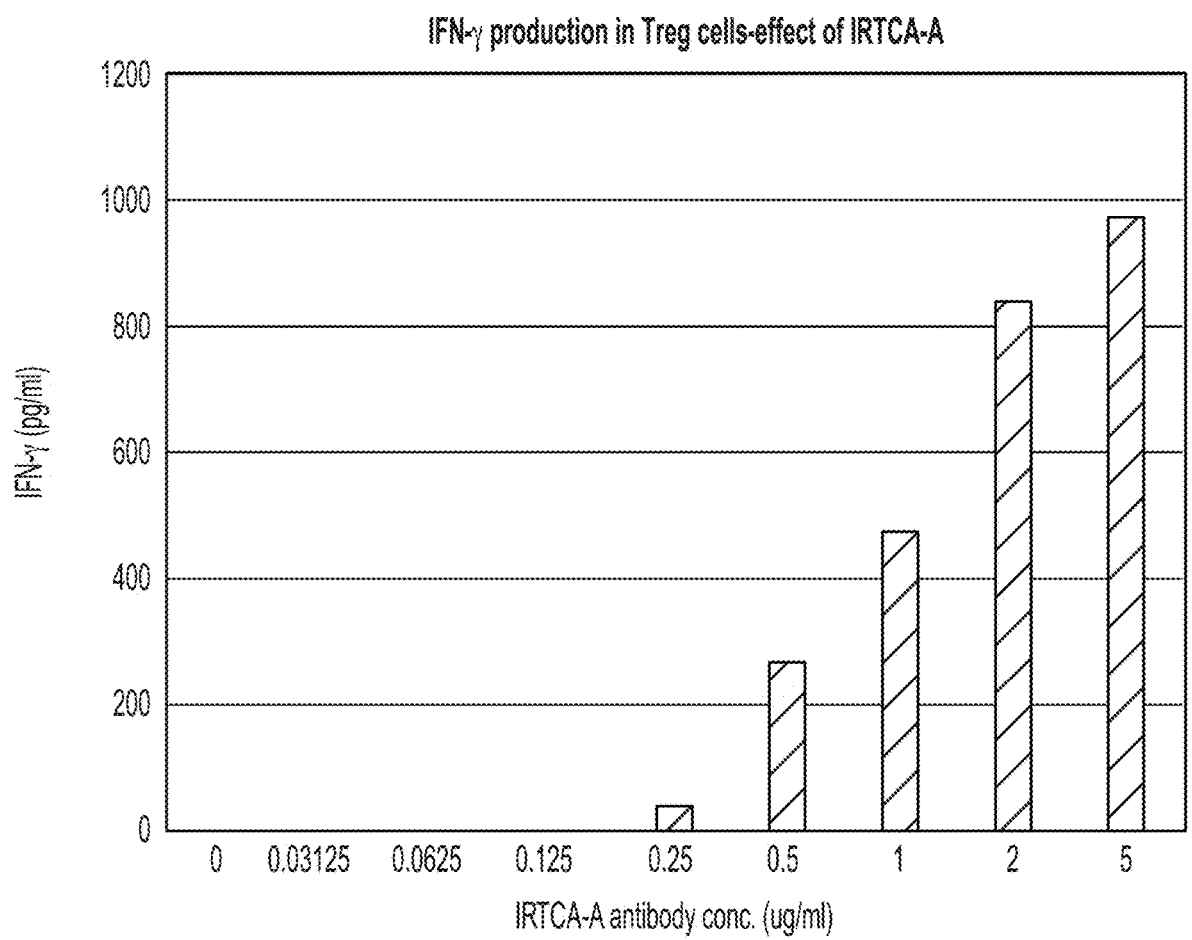
FIG. 6A depicts a graph quantifying dose-dependent changes in secretion of IFN-γ from $T_{reg}$ cells after treatment with IRTCA-A.
Figure 6B:
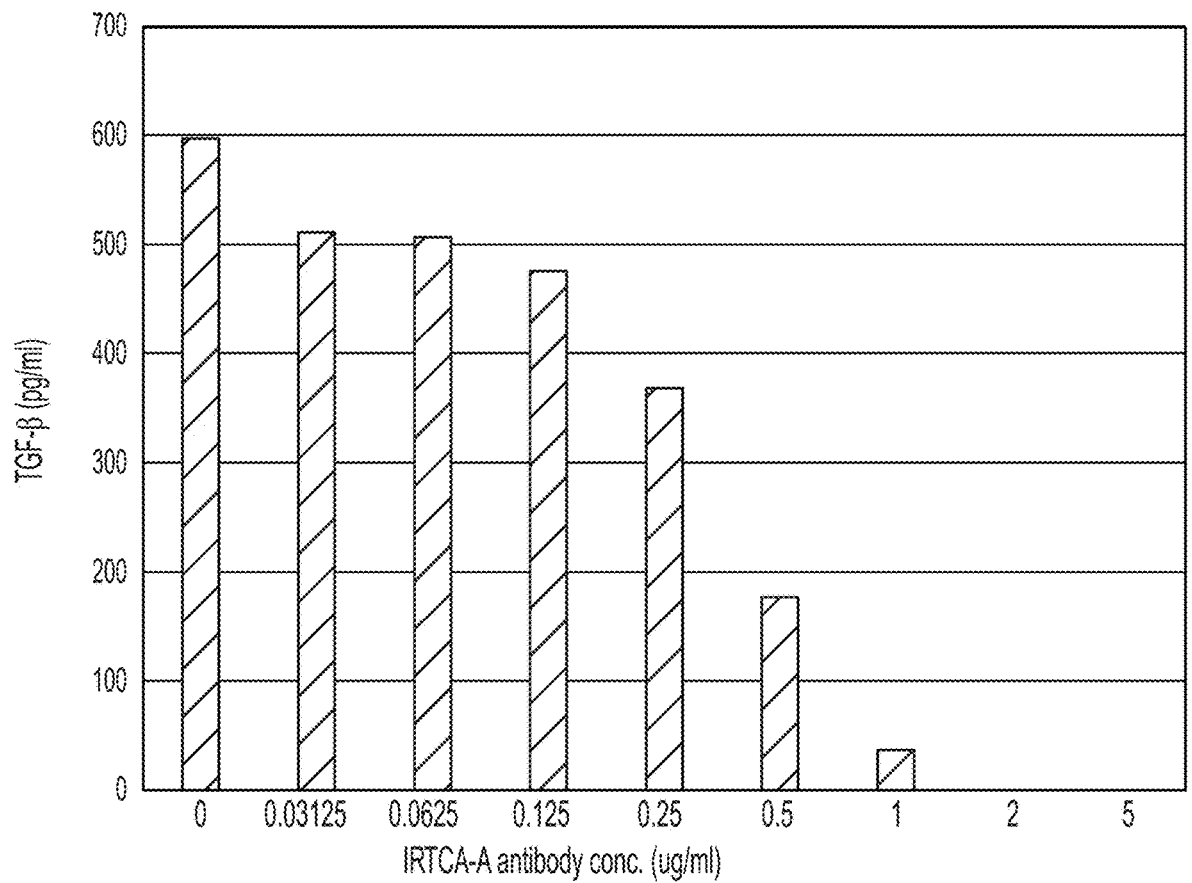
FIG. 6B depicts a graph quantifying dose-dependent changes in secretion of TGF-β from $T_{reg}$ cells after treatment with IRTCA-A.

Subsequently, as shown in FIG. 6A and FIG. 6B, IRTCA-A acted on AITR of the $T_{reg}$ cell to increase secretion of IFN-γ and at the same time decrease secretion of TGF-β. Additionally, IRTCA-A treatment induced IFN-γ secretion in CD4$^+$ T cell and polarized to $T_H1$ cells (FIG. 5). That is, IRTCA-A effectively stimulated AITR of the T cell in a dose-dependent manner and promote conversion of $T_{reg}$ into $T_H1$-like cells. This indicated that IFN-γ and TGF-β might be used as functional tools with which to measure the effect of stimulating the AITR signaling system.

Example 5: Activation and Polarization of CD4$^+$ T Cell Based on Affinity-Maturated IRTCA-A This example describes the effects of affinity-matured IRTCA-A series antibodies on CD4$^+$ T cells, including cytokine secretion.

First, in order to verify whether the mutation of Fabs changed the epitopes to which they could bind, a deletion mutant of AITR was fabricated, and comparison with the parental form indicated that, as anticipated, the IRTCA-A series Fabs maintained their ability to bind the AITR epitope (Table 7). In order to evaluate the functionality of the 5 species of affinity-maturated IRTCA-A Fab (IRTCA-A1, 10, 12, 14, 15, of Table 7), which have high binding affinity with AITR compared to IRTCA-A, the polarization efficiency of the antibodies to change CD4$^+$ T cells into $T_H1$-type cells was measured.

Table 7 lists names of the Fab forms which were isolated from the Fab clones in the IRTCA-A series and then purified (*: Fab whose epitope-binding ability was verified).

TABLE 7

| Clone Name | mAb Name |
|---|---|
| IRTCA-A | IRTCA-A |
| L1E9 | IRTCA-A1* |
| H1A10 | IRTCA-A10* |
| H2A10 | IRTCA-A12* |
| H2F8 | IRTCA-A14* |
| H1F1 | IRTCA-A15* |

Figure 7A:
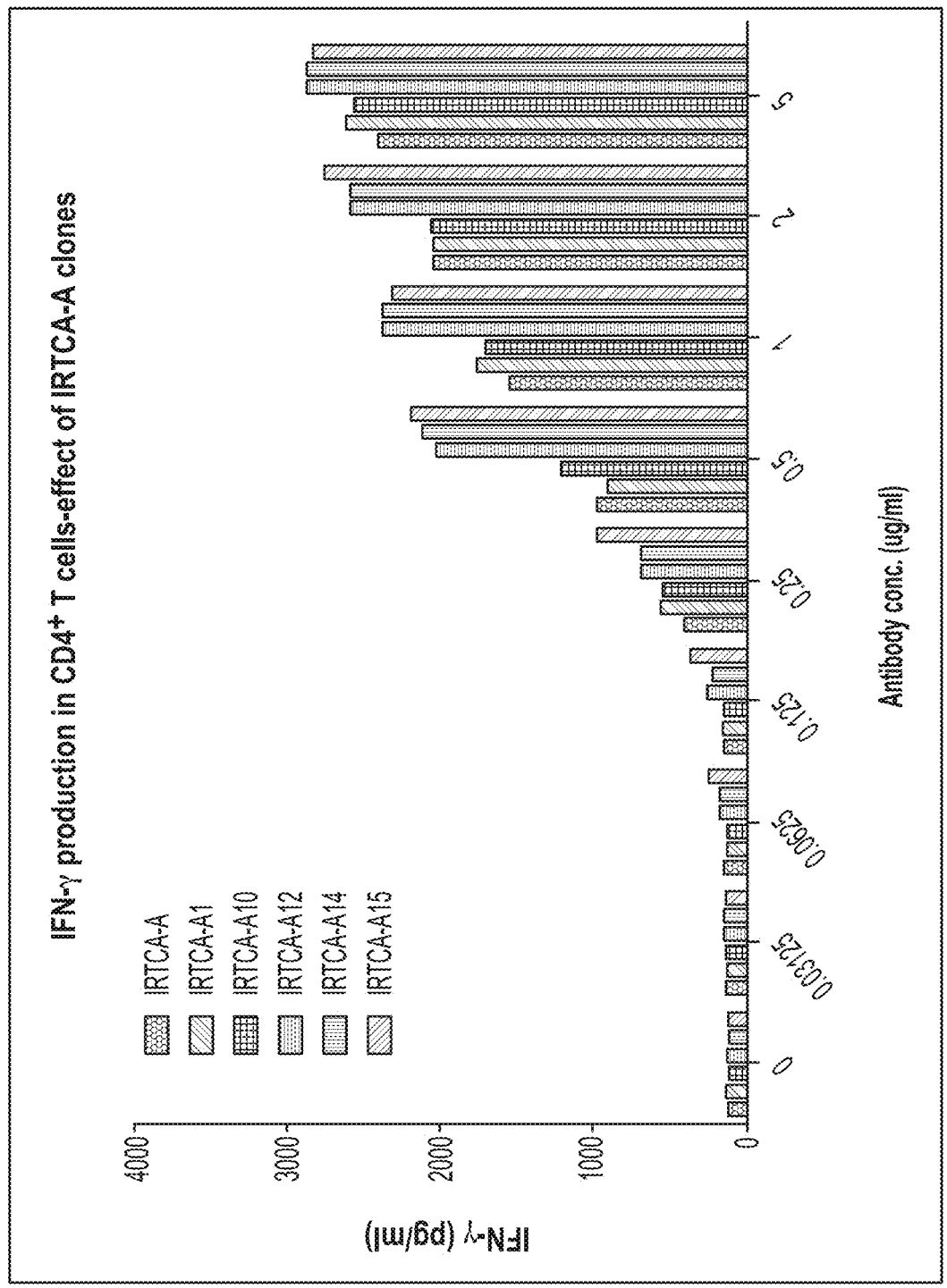
FIG. 7A depicts a graph quantifying dose-dependent changes in secretion of IFN-γ in CD4 T cells after treatment with several IRTCA-A mutants.

As shown in Table 8 and FIG. 7A, when purified CD4$^+$ T cells were treated with affinity-maturated mAb of IRTCA-A and the quantity of cytokine secretion from culture supernatant was measured, affinity-maturated mAbs promote secretion of IFN-γ and also induce secretion of IFN-γ. These data indicate that IRTCA has the function accelerating polarization of CD4$^+$ T cells into $T_H1$ cells secreting IFN-γ and that Fabs of the same series also interact with AITR on the surface of CD4$^+$ T cells. In particular, administration of 0.5 μg IRTCA-A12, IRTCA-A14 and IRTCA-A15 led cells to exhibit secretion of IFN-γ greater than the levels of IFN-γ secretion caused by IRTCA-A by approximately 200% or more (see, FIG. 7A and Table 8).

Table 8 shows the results of measuring IFN-γ secretion in CD4$^+$ T cells after administration of IRTCA-A series mAbs ($K_D$ ratio=mutant $K_D$/IRTCA-A $K_D$).

TABLE 8

| Clone | $K_D$ Ratio | IFN-γ Secretion |
|---|---|---|
| IRTCA-A | 1.0 | + |
| IRTCA-A1 | 8.2 | + |
| IRTCA-A10 | 8.4 | ++ |
| IRTCA-A12 | 27.6 | +++++ |
| IRTCA-A14 | 30.1 | +++++ |
| IRTCA-A15 | 44.4 | +++++ |

Example 6: Effect of Anti-AITR Antibody on $T_{reg}$ Cells (Regulatory T Cells)

In order to determine influence of the mAbs which increased binding affinity in IRTCA-A on $T_{reg}$ cells, CD4$^+$ CD25$^{high}$FOXP3$^+$ $T_{reg}$ cells were isolated and treated with IRTCA-A1, A10, A12, A14, and A15.

Figure 7B:
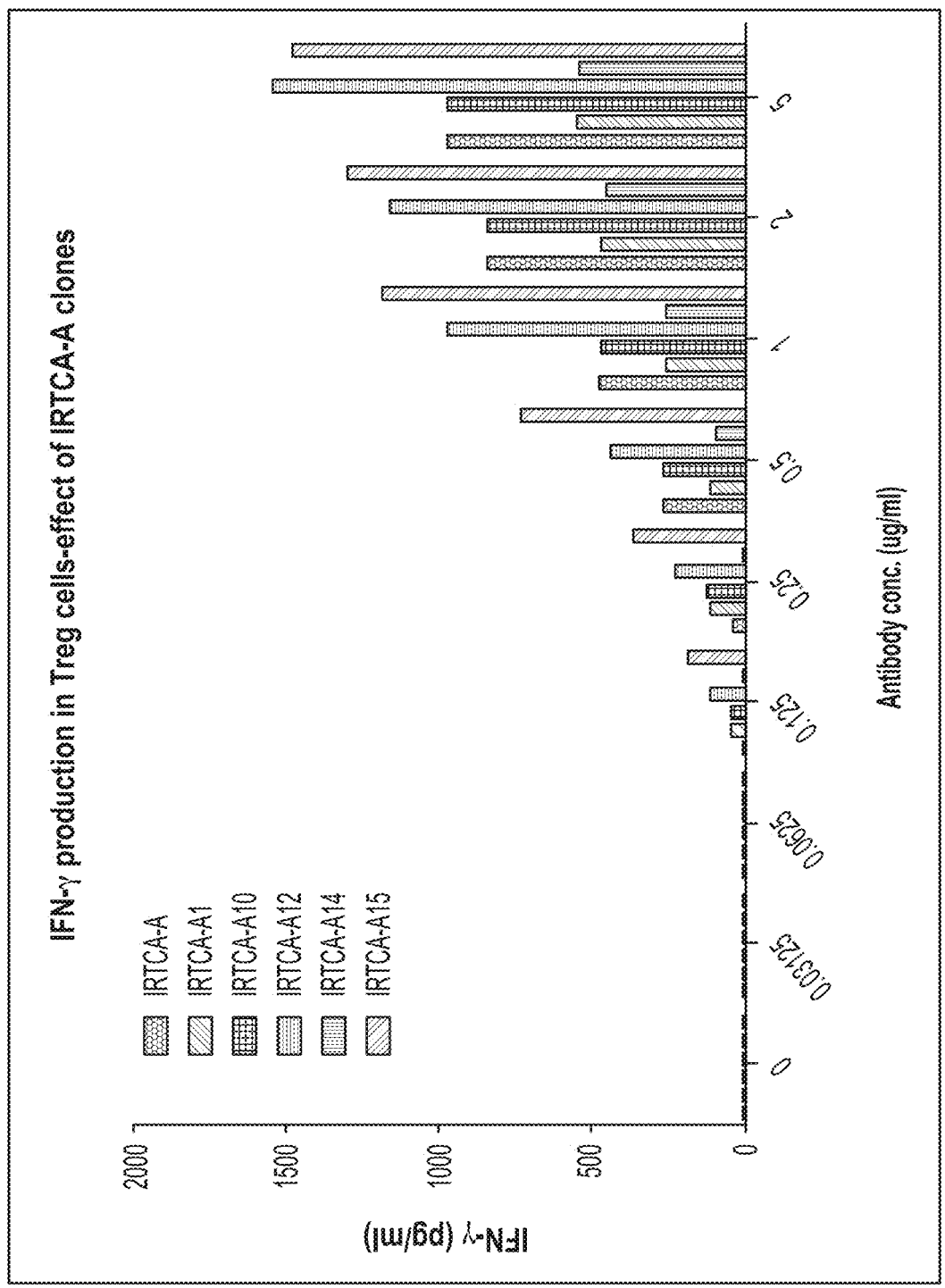
FIG. 7B depicts a graph quantifying dose-dependent changes in secretion of IFN-γ in $T_{reg}$ cells after treatment with several IRTCA-A mutants.

As shown in Table 9 and Table 10, after treatment with the IRTCA-A antibodies, secretion of IFN-γ (a marker of $T_H1$ polarization) increased (FIG. 7B) whereas secretion of TGF-β (a representative suppression cytokine of $T_{reg}$ cells) decreased (FIG. 7C).

According to the above results, the mAbs of the IRTCA-A series are expected to decrease the suppressive capacity of $T_{reg}$ cells and to increase activation of $T_{eff}$ cells so that a micro-environment comprising anti-cancer effects is created. Additionally, as shown in Table 3, Table 9 and Table 10, increased affinity for AITR had a substantial correlation with cytokine secretion, which contributes to the anti-cancer role of the IRTCA-A antibodies. IRTCA-A12 and IRTCA-A15, which had smaller $K_D$ values (see Table 3), that is, improved binding affinity with AITR compared with IRTCA-A, resulted in increased secretion of IFN-γ as well.

Furthermore, while the IRTCA-A series antibodies, which have different CDR sequences are still similar to each other, bind to a common epitope of the AITR antigen, it is also noteworthy that they exhibit effects of different tendency. In other words, it was anticipated that depending upon binding affinity, IRTCA-A15 could achieve the same anti-cancer effect in the CD4$^+$CD25$^{high}$ T$_{reg}$ cell at approximately 25% of the dose of IRTCA-A. This means not only that the dose of AITR mAb can be regulated to control the function of the T$_{reg}$ cell, but also that a different mAb species that recognize the same epitope and but have enhanced binding affinity can be used to control therapeutic effects by sending signals of different intensity.

Table 9 shows changes in secretion of IFN-γ from T$_{reg}$ cells after administration of IRTCA-A series mAb.

TABLE 9

| Clone | K$_D$ Ratio | IFN-γ Secretion |
|---|---|---|
| IRTCA-A | 1.0 | ++ |
| IRTCA-A1 | 8.2 | + |
| IRTCA-A10 | 8.4 | ++ |
| IRTCA-A12 | 27.6 | ++++ |
| IRTCA-A14 | 30.1 | + |
| IRTCA-A15 | 44.4 | +++++ |

Table 10 shows changes in secretion of TGF-β from T$_{reg}$ cells after administration of IRTCA-A series mAb.

TABLE 10

| Clone | K$_D$ Ratio | TGF-β Secretion |
|---|---|---|
| IRTCA-A | 1.0 | +++++ |
| IRTCA-A1 | 8.2 | +++ |
| IRTCA-A10 | 8.4 | +++ |
| IRTCA-A12 | 27.6 | + |
| IRTCA-A14 | 30.1 | + |
| IRTCA-A15 | 44.4 | + |

Example 7: Engraftment of Human Peripheral Blood Mononuclear Cells in NOD-SCID Mouse and Anti-Tumor Activity of Anti-AITR Antibody This example describes the anti-tumor effects of anti-AITR antibodies on NOD-SCID mice after administration of human peripheral blood mononuclear cells (PBMCs) and human colorectal cancer cells.

First, after peripheral venous blood collected from healthy donors with the HLA-A24 type was treated with heparin, Ficoll-paque (GE Healthcare, Piscataway, N.J.) density gradient centrifugal separation was conducted to obtain peripheral blood mononuclear cells (PBMCs). Next, within 3 hours used for recovery, 1×10$^7$ human PBMCs included in RPMI was injected into each NOD-SCID mouse peritoneally. The 21 grafted mice above were analyzed in 5 weeks following injection of human PBMCs (HLA-A24 type).

The 7-week-old NOD-SCID mice (Jackson Laboratory, Barharbor, Me.) were bred in an animal room that was a SPF (specific pathogen free) environment. All animal experiments were performed according to the Experimental Animal Ethics Guidelines.

In order to evaluate the anti-cancer effects of the anti-AITR monoclonal antibodies (IRTCA), human colorectal cancer cells of HT29 (HLA-A24 type, 1×10$^7$ cells/mouse) were subcutaneously injected on the dorsal side of the Hu-PBL-SCID mouse, and when the tumor size reached the diameter of ~2 cm, the anti-AITR monoclonal antibody (IRTCA) was administered intraperitoneally at doses of 0.3 mg, 0.6 mg, 1.0 mg, 3.0 mg, 5.0 mg and 10.0 mg per 1 kg body weight every 5 days, for a total of 3 administrations. Human IgG was used as the control group. The mouse tumor volume (in mm$^3$) was measured according to the group and date.

Figure 8:
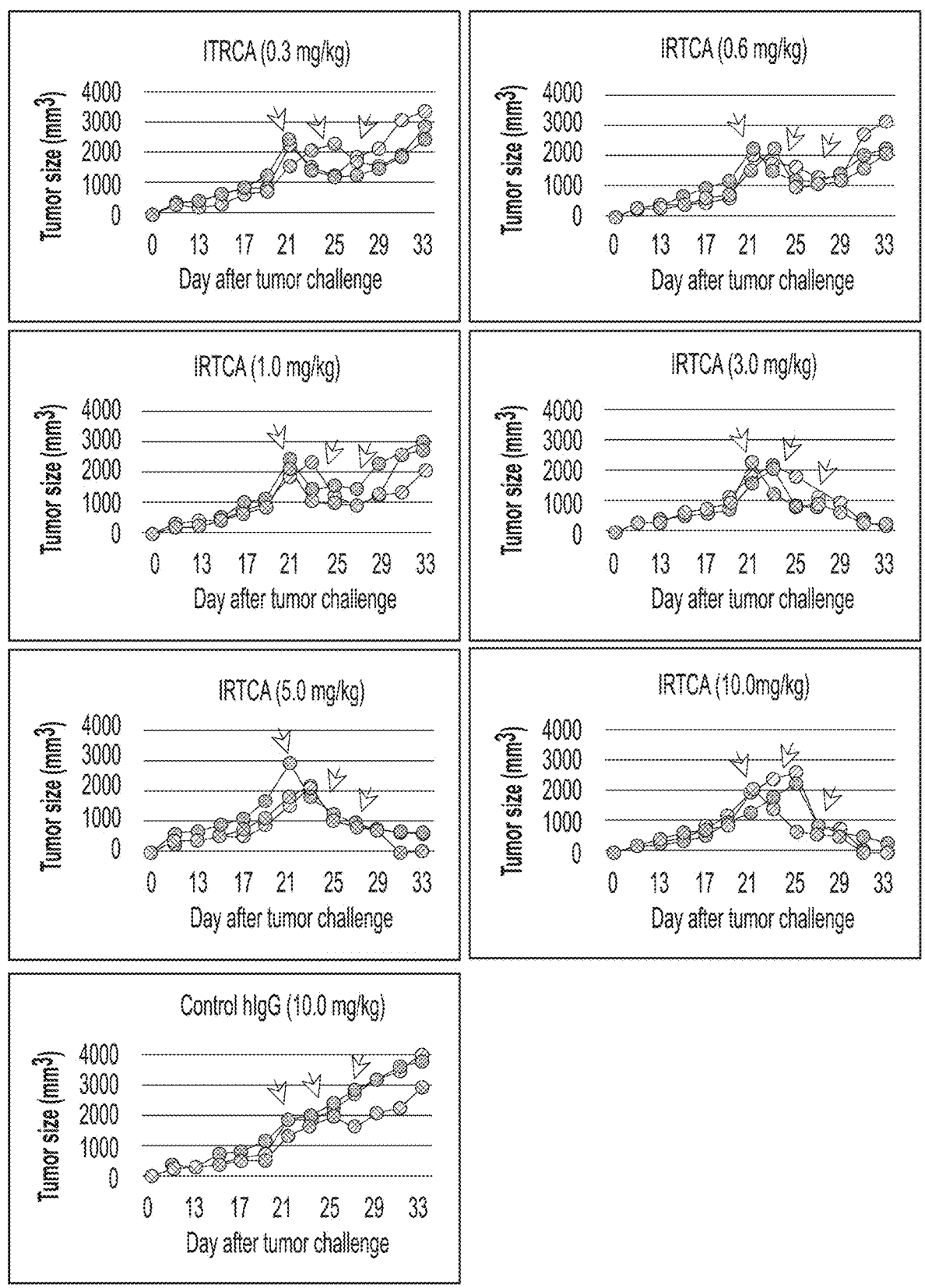
FIG. 8 depicts graphs showing dose-dependent reductions in tumor volume (from injection with colorectal cancer cells) following treatment of Hu-PBL-SCID mice with IRTCA antibody.

As shown in FIG. 8, the tumor size in mice treated with the anti-AITR monoclonal antibodies (IRTCA) decreased in a manner that correlated with antibody concentration. In particular, the IRTCA concentration of 3.0 mg/kg revealed such effect that the tumors were completely eradiated by Day 33.

Figure 9:
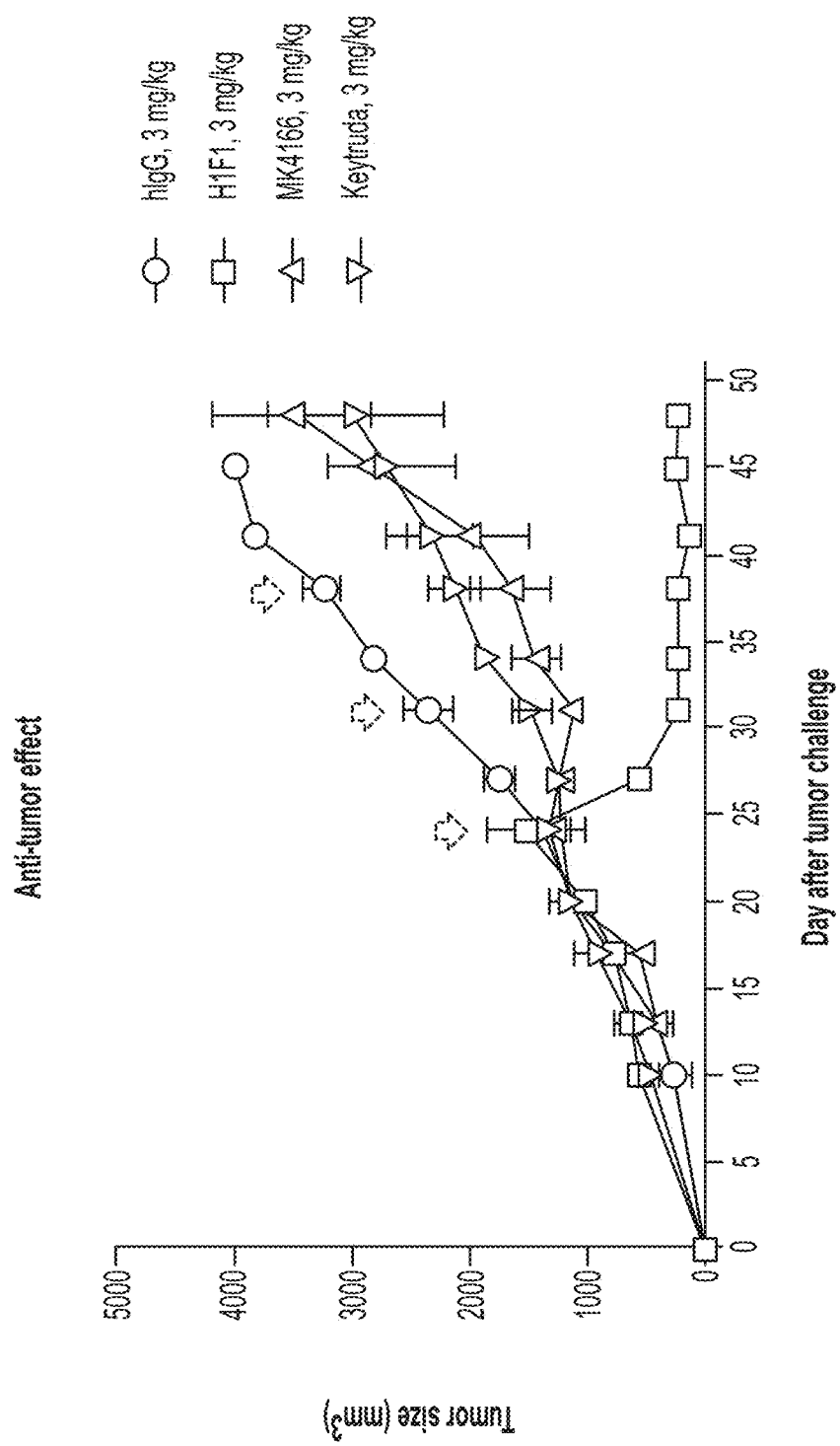
FIG. 9 depicts a graph quantifying the effect of control hIgG, H1F1 antibody, MK4166 and Keytruda on tumor size. Arrows indicate days of injection with treatment or control antibody.
Figure 10A:
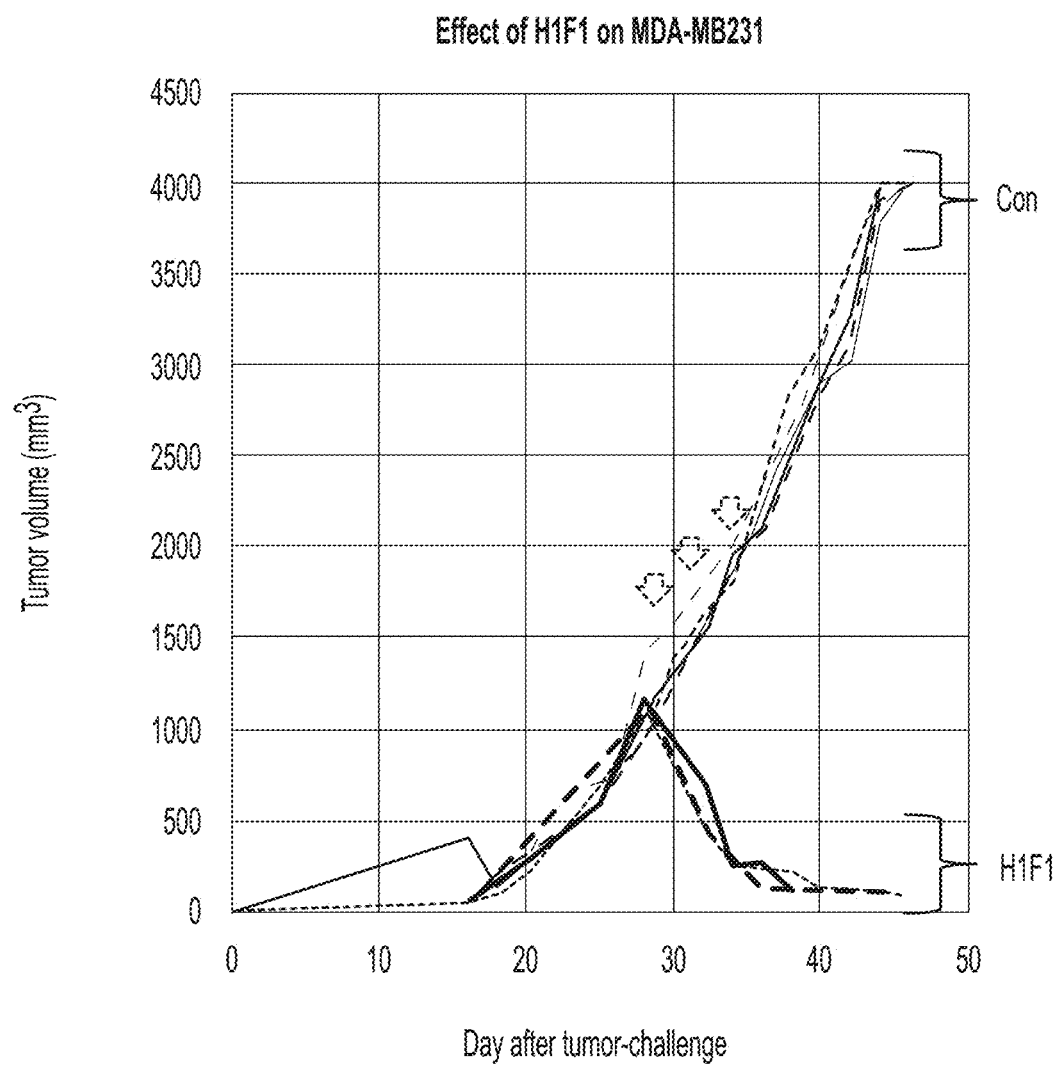
FIG. 10A depicts a graph quantifying the effect of H1F1 or control antibody on tumor size (triple negative breast cancer) after 3 doses (arrows) of antibody treatment.
Figure 10B:
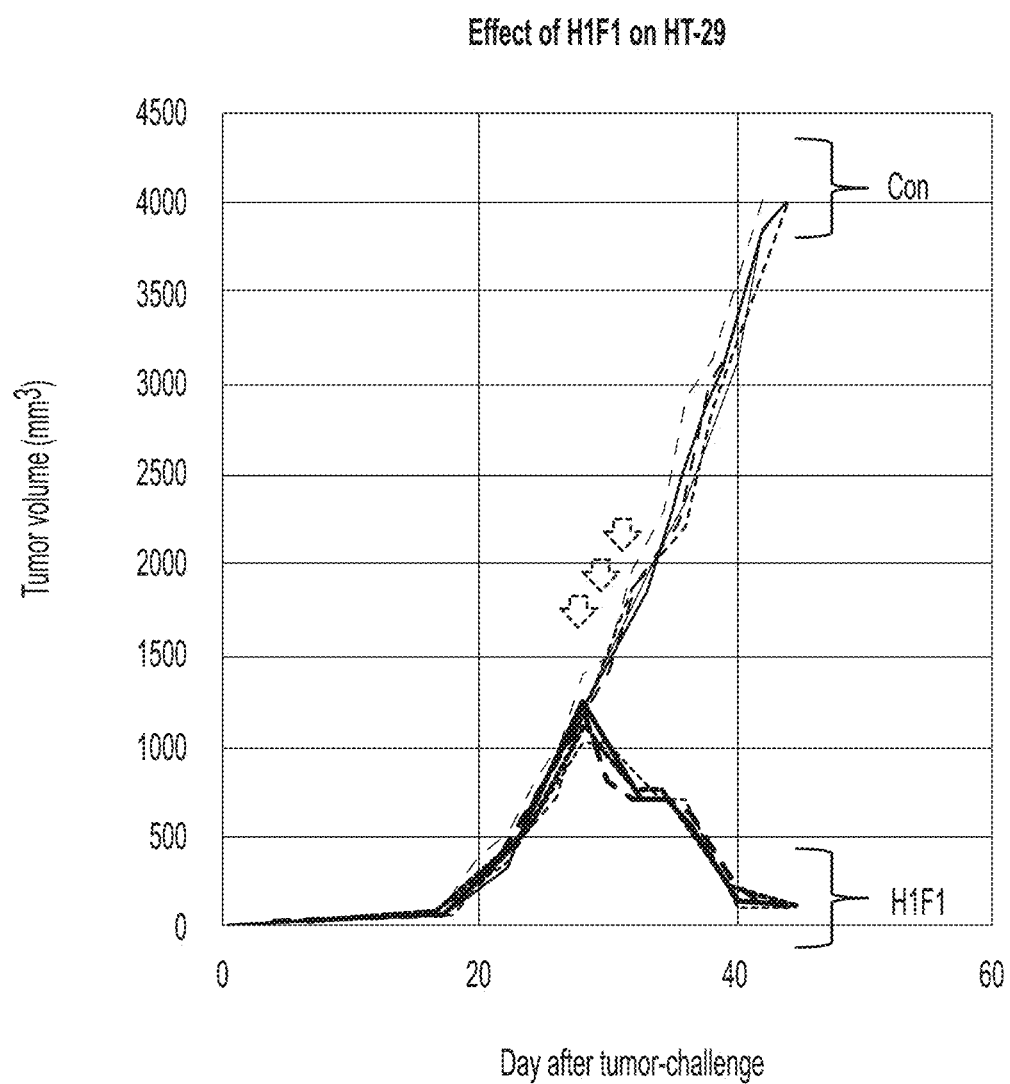
FIG. 10B depicts a graph quantifying the effect of H1F1 or control antibody on tumor size (colon cancer) after 3 doses (arrows) of antibody treatment.
Figure 10C:
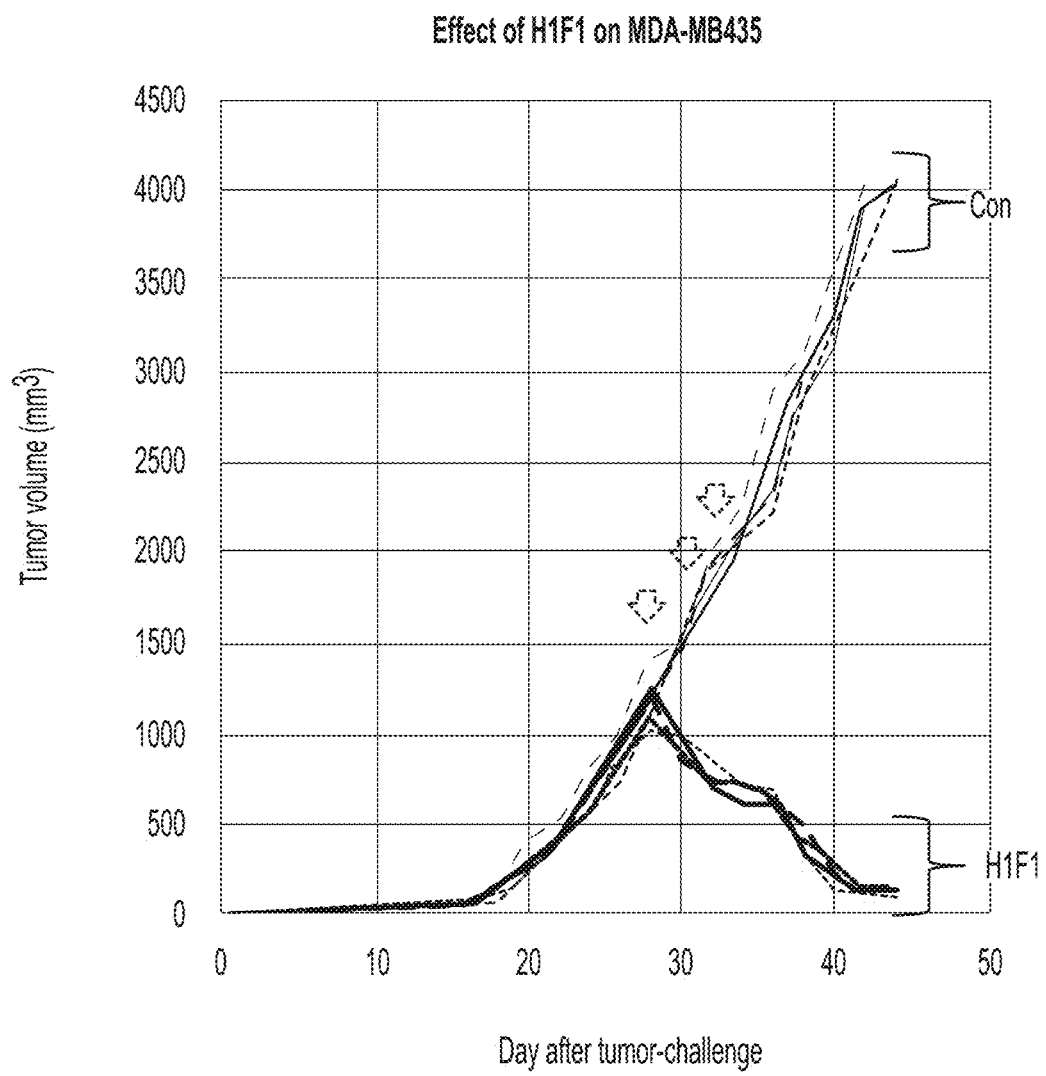
FIG. 10C depicts a graph quantifying the effect of H1F1 or control antibody on tumor size melanoma) after 3 doses (arrows) of antibody treatment.
Figure 10D:
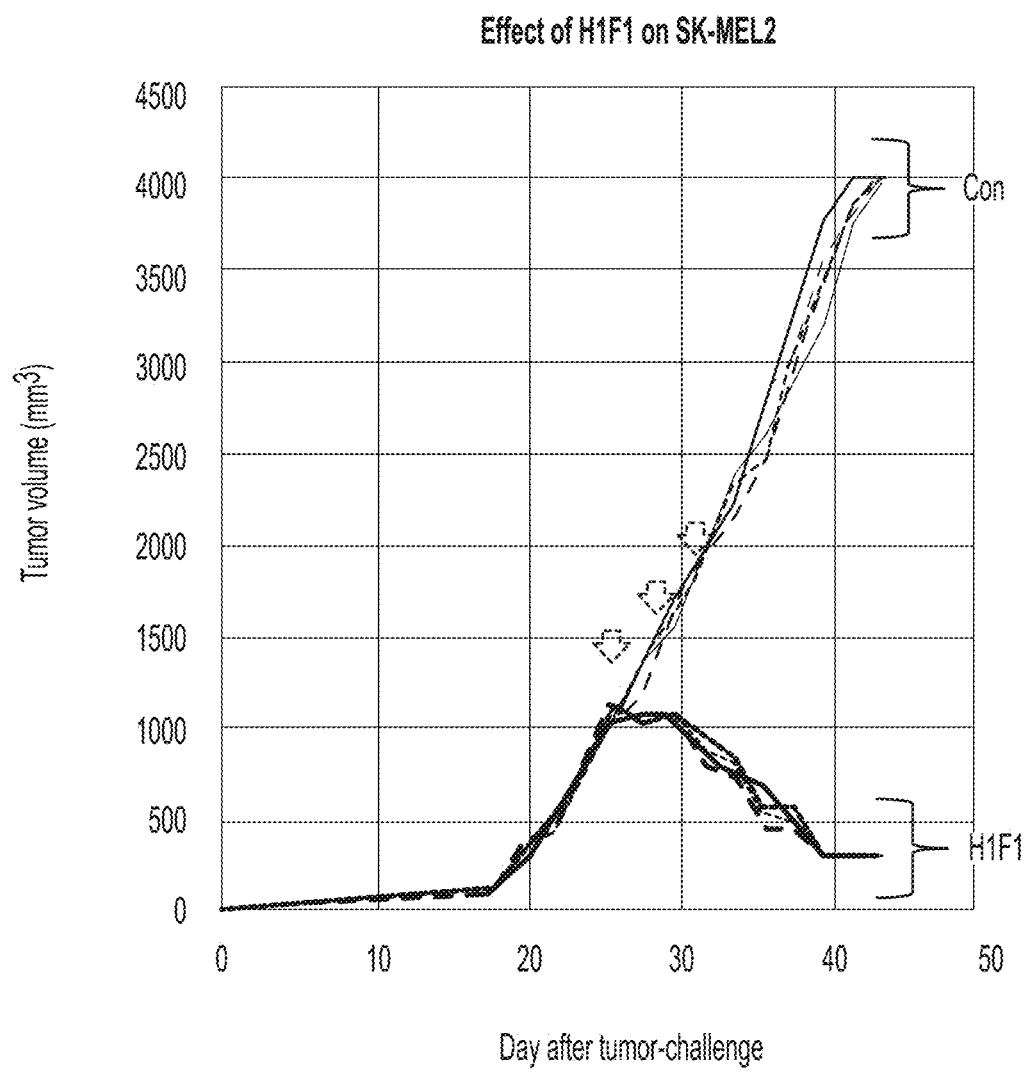
FIG. 10D depicts a graph quantifying the effect of H1F1 or control antibody on tumor size (melanoma) after 3 doses (arrows) of antibody treatment.

Additionally, shown in FIG. 9, when tumor-challenged mice injected with HT29 cells were treated with control hIgG, H1F1, MK4166 (Merck's anti-GITR antibody) or Pambrolizumab (Keytruda) via i.v. injection at one week intervals at a dosage of 3.0 mg/kg, only H1F1 resulted in a decrease in tumor size over several weeks.

The exemplary anti-AITR monoclonal antibody H1F1 was also administered to 7-weeks-old, female, NOD-SCID mice humanized with human PBMCs (as described above), in order to test its anti-tumor effect against four cancers: triple negative breast cancer (MDA-MB231), colon cancer (HT-29) and melanoma (MDA-MB435, SK-MEL2). Mice were injected with 1×10$^7$ tumor cells per mouse and once the size of the tumors reached 1000-1500 mm$^3$ in volume, the tumor-challenged mice were injected intraperitoneally (i.p.) with H1F1 or hIgG once every three days for three times. The width, length, and height of the tumors were measured with calipers at the time points indicated in FIG. 10A-D. The arrows indicate the time points when H1F1 or control were injected.

Example 8: Analysis of Tissue Cross Reactivity, Toxicology & Mechanism of Action of Anti-AITR Antibody in Cynomolgus Monkey This example describes the effects of treatment with an exemplary anti-AITR antibody on cynomolgus monkeys. Seven Cynomolgus monkeys (*Macacafascicularis*) approximately 25-35 years of age and approximately 2-3 kg in weight were used for this study. The control group contained 1 female monkey who received a dose volume of 39 mL/kg. The low dose group contained 1 male monkey and 1 female monkey who each received an H1F1 dosage of 22.5 mg/kg at a concentration of 2.3 mg/kg and a dose volume of 9.75 mL/kg. The middle dose group contained 1 male monkey and 1 female monkey who each received an H1F1 dosage of 45 mg/kg at a concentration of 2.3 mg/kg and a dose volume of 19.5 mL/kg. The high dose group contained 1 male monkey and 1 female monkey who each received an H1F1 dosage of 90 mg/kg at a concentration of 2.3 mg/kg and a dose volume of 39 mL/kg.

When toxicology tests were run on the monkeys, no abnormalities were observed in clinical symptoms, body/organ weight, blood tests, urine tests, histopathological examination or electrocadiography. The no-observed-adverse-effect-level (NOAEL) for H1F1 was found to be over 90 mg/kg in macaques.

Figure 11:
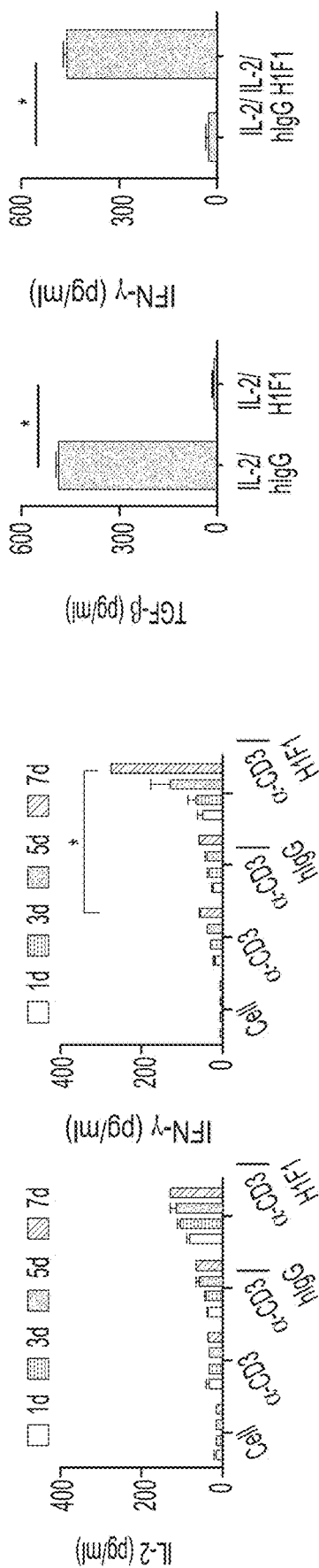
FIG. 11 depicts graphs quantifying the effect of H1F1 on cytokine secretion in $CD4^+CD25^{high}Foxp3^+$ T cells oiMacaca fascicularis.

In vitro, the effect of H1F1 on cytokine secretion was tested on CD4$^+$CD25$^{high}$Foxp3$^+$ T cells. As shown in FIG. 11, treatment with H1F1 lead to polarization of CD4$^+$CD25$^{high}$Foxp3$^+$ T cells to T$_H$1 cells, evidenced by an increase in the secretion of IFN-γ and a decrease in the TGF-β after treatment with H1F1.

Figure 12:
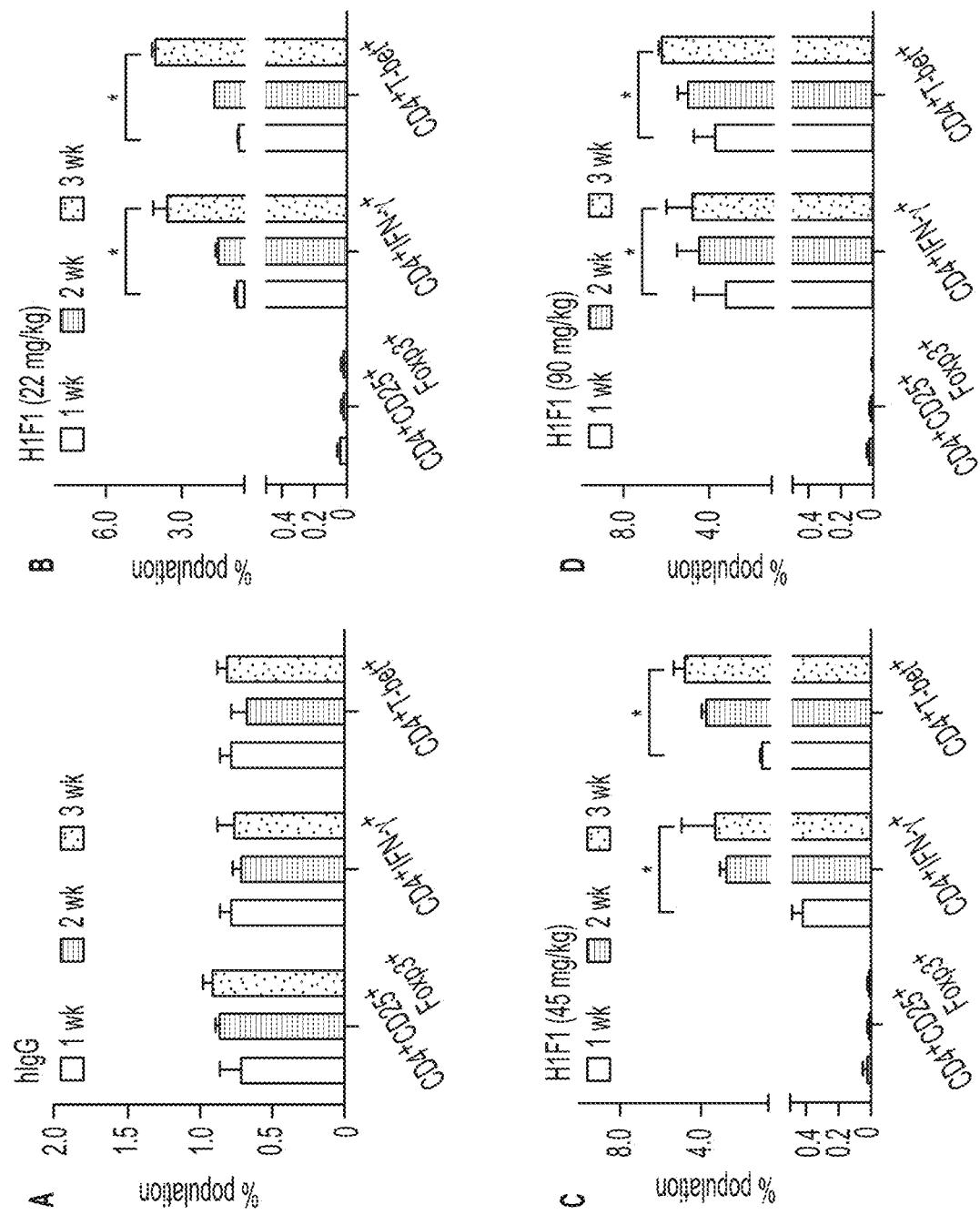
FIG. 12 depicts graphs quantifying H1F1-mediated conversion of regulatory T cells to $T_H1$ cells in macaques in vivo. Unlike the hIgG-treated control group (A), the cells treated with 22 mg/kg H1F1 (B), 45 mg/kg H1F1 (C) and 90 mg/kg H1F1 (D) showed an increase in IFN-γ positive $CD4^+$ T cells over the course of 3 weeks.
Figure 13:
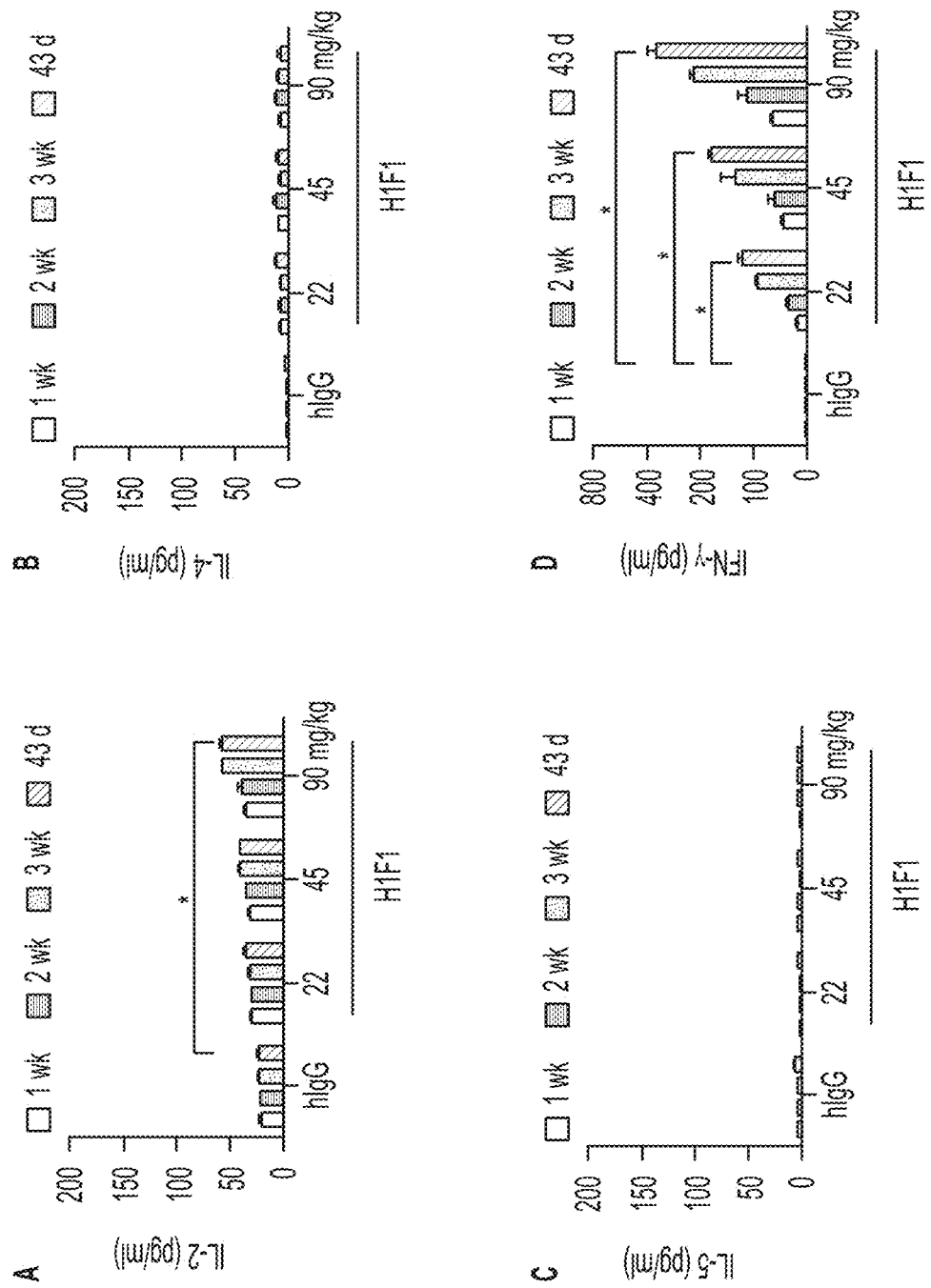
FIG. 13 depicts graphs showing that cytokine induction by H1F1 was differential. Secretion of the cytokines IL-4 (B), and IL-5 (C) was not effected in cells treated with H1F1, whereas IL-2 (A) and IFN-γ secretion (D) increased after treatment with H1F1.

An H1F1-mediated conversion of regulatory T cells to T$_H$1 cells was also observed in macaques in vivo. As shown in FIG. 12, all three doses of H1F1 lead to an increase in IFN-γ positive CD4$^+$ T cells over the course of 3 weeks. Additionally, H1F1 cytokine induction was differential, as shown in FIG. 13, T$_H$1-type of cytokines (IL-2 and IFN-γ) were increased after treatment with H1F1, whereas the level of T$_H$2-type cytokines (IL-4 and IL-5) were not altered.

Figure 14:
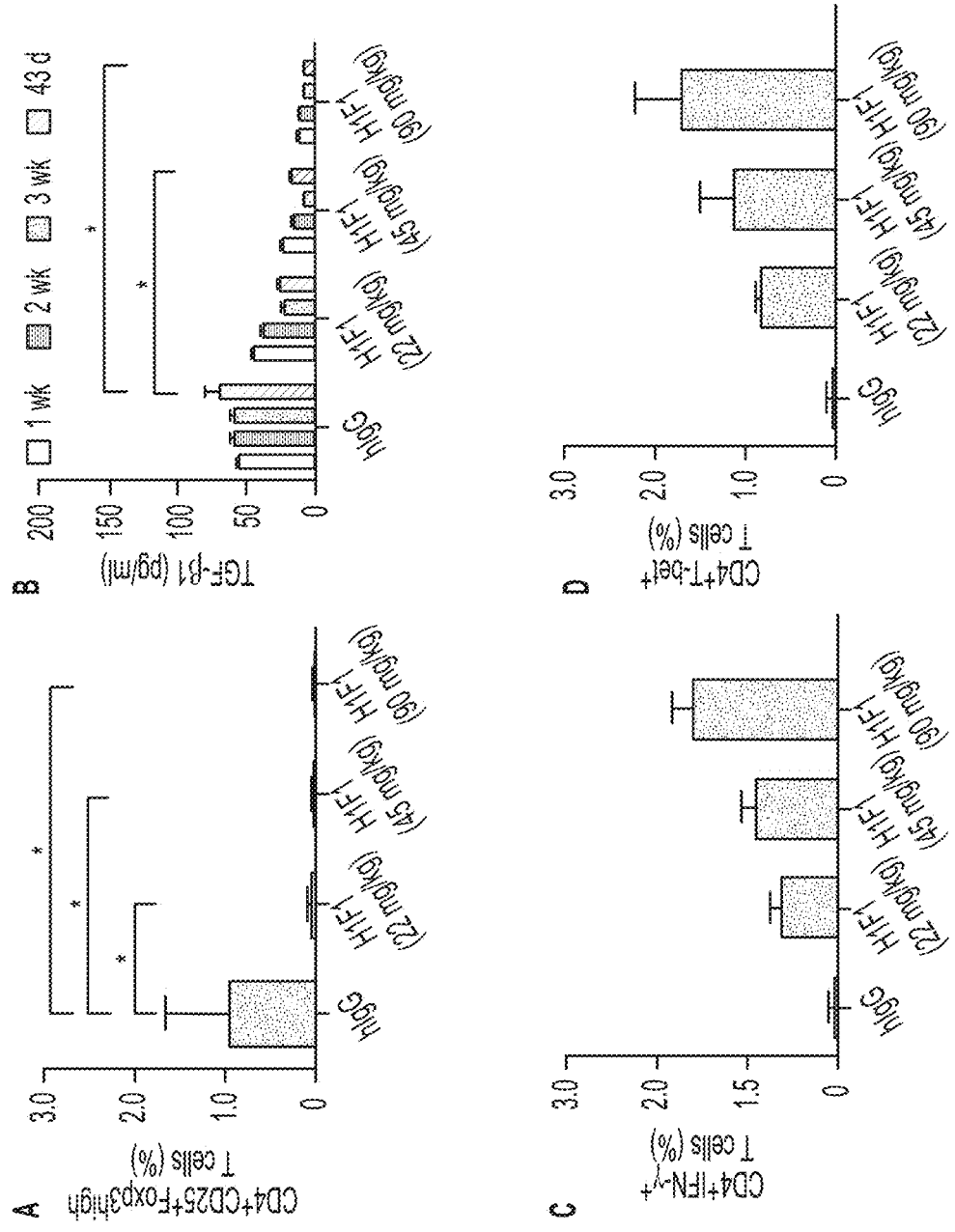
FIG. 14 depicts graphs quantifying the dose-dependent effect of H1F1 on populations of cells expressing $CD4^+CD25^+Foxp3^{high}$ (A), TGF-β (B), $CD4^+IFN-Y$ (C) and $CD4^+$ $T-bet^+$ (D).

Treatment with H1F1 also affected the balance between $T_{reg}$ and $T_H1$ cells in macaques in vivo. As shown in FIG. 14, in splenocytes of H1F1-administered macaques, the population of regulatory T cells and the associated cytokine TGF-β were decreased, while the population of $T_H$1-type cells increased.

Figure 15:
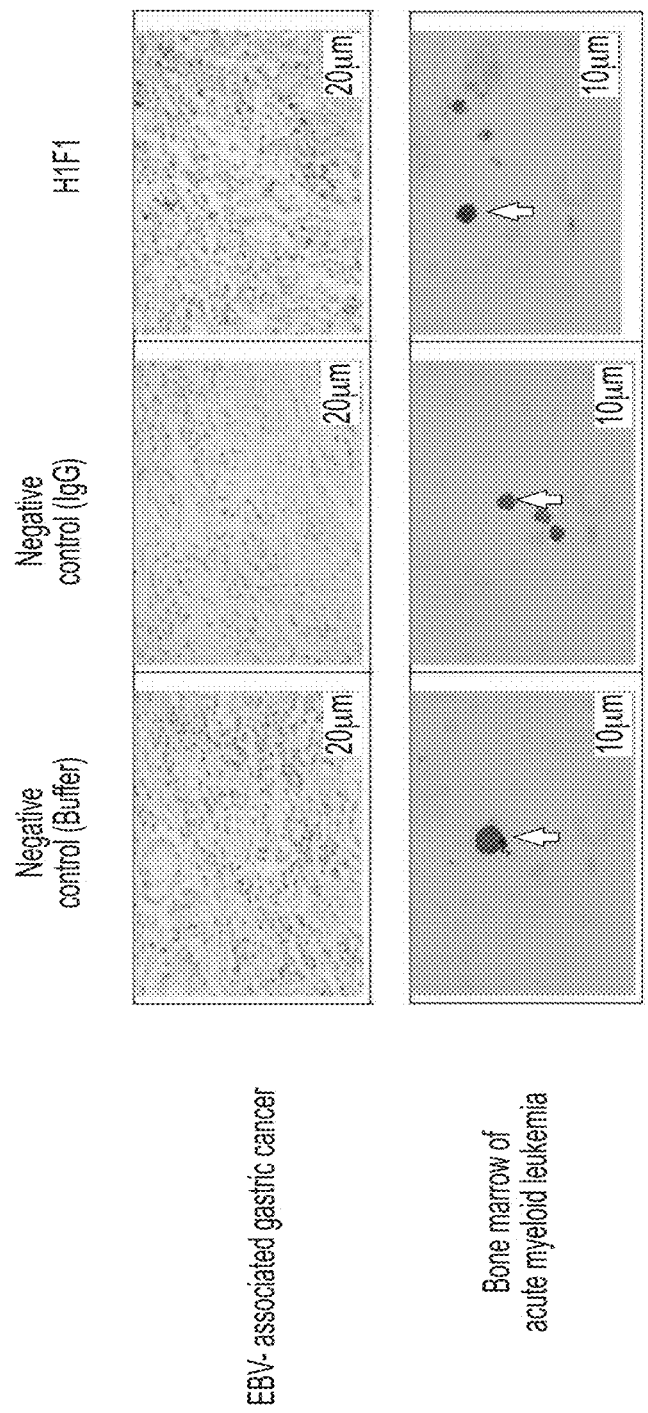
FIG. 15 depicts H1F1-specific staining in EBV-positive gastric cancer cells and bone marrow from an AML patient.

Additionally, tissue cross-reactivity studies were performed on tissues from 15 different rat organs, 16 different dog organs, 16 different monkey organs, 13 different human organs (138 different tissues) and tissues from cancer patients with EBV-associated gastric cancer and bone marrow from acute myeloid leukemia. H1F1-specific staining was detected in the immune system but not in other normal human tissues. FIG. 15 shows that H1F1-specific staining was observed in EBV-positive gastric cancer and bone marrow from an AML patient. Cross-reactivity was detected in macaque and dog lymphocytes, but no cross-reactivity was observed in rat tissues.

Example 9: Creation of Improved Anti-AITR Antibodies

This example describes the production of optimized anti-AITR antibodies.

Anti-AITR Antibody Production

Expi293 cells were put in a 125 mL Erlenmeyer flask and cultured in Expi293 expression medium in an 8% $CO_2$ incubator under spin (125 rpm) at 37° C. Cells were cultured at 2-2.5×10⁶ cell/ml in flask. On day −1, cells (2×10⁶ cell/ml per flask) were prepared in 30 ml of Expi293 expression medium in a 125 mL Erlenmeyer flask. On day 0, Opti-MEM medium was pre-warmed in a 37° C. incubator for about 30 minutes. Tubes 1 and 2 were prepared, and 1.5 mL of pre-warmed Opti-MEM medium was added to each tube. 30 μg of DNA (HC: 15 μg, LC: 15 μg) were added to Tube 1 and mixed well. 80 μL of Expifectamine 293 reagent was added to Tube 2 and mixed well. After reaction for 5 minutes at room temperature, the contents of Tube 2 were added to Tube 1 and mixed well. The mixture was allowed to react for 20 minutes at room temperature. Once the mixture in the tube was confirmed to have turned cloudy, 3 mL of the DNA-Complex was taken from the flask and added dropwise. After adding, it was cultured in an incubator for 18-20 minutes while being spun, and enhancer 1 and enhancer 2 provided in the Expifectamine 293 Transfection kit were added. It was cultured while being spun for about 7 days. Table 11 below summarizes the heavy (HC) variable domains and light chain (LC) variable domains used to create the mutant anti-AITR antibodies. Table 12 below includes the heavy chain and light chain variable domain and CDR SEQ ID NOs corresponding to the mutant anti-AITR antibodies.

TABLE 11

H1F1 Mutant antibody Expi293 cell transfection table

| Ab | HC | LC |
|---|---|---|
| H1F1.M1 | H1F1 WT | H1F1.L1 |
| H1F1.M2 | H1F1 WT | H1F1.L2 |
| H1F1.M3 | H1F1 WT | H1F1.L3 |
| H1F1.M4 | H1F1.H1 | H1F1.WT |
| H1F1.M5 | H1F1.H1 | H1F1.L1 |
| H1F1.M6 | H1F1.H1 | H1F1.L2 |
| H1F1.M7 | H1F1.H1 | H1F1.L3 |
| H1F1.M8 | H1F1.H2 | H1F1.WT |
| H1F1.M9 | H1F1.H2 | H1F1.L1 |
| H1F1.M10 | H1F1.H2 | H1F1.L2 |
| H1F1.M11 | H1F1.H2 | H1F1.L3 |
| H1F1.M12 | H1F1.H3 | H1F1.WT |
| H1F1.M13 | H1F1.H3 | H1F1.L1 |
| H1F1.M14 | H1F1.H3 | H1F1.L2 |
| H1F1.M15 | H1F1.H3 | H1F1.L3 |
| H1F1.M16 | H1F1.H4 | H1F1.WT |
| H1F1.M17 | H1F1.H4 | H1F1.L1 |
| H1F1.M18 | H1F1.H4 | H1F1.L2 |
| H1F1.M19 | H1F1.H4 | H1F1.L3 |
| H1F1.M20 | H1F1.H5 | H1F1.WT |
| H1F1.M21 | H1F1.H5 | H1F1.L1 |
| H1F1.M22 | H1F1.H5 | H1F1.L2 |
| H1F1.M23 | H1F1.H5 | H1F1.L3 |
| H1F1.M24 | H1F1.H2 | LC-A1 |
| H1F1.M25 | H1F1.H2 | LC-A2 |
| H1F1.M26 | H1F1.H2 | LC-A3 |
| H1F1.M27 | H1F1.H2 | LC-A4 |
| H1F1.M28 | H1F1.H2 | LC-A5 |
| H1F1.M29 | H1F1.H2 | LC-A6 |
| H1F1.M30 | H1F1.H2 | LC-A7 |
| H1F1.M31 | HIFl.WT.HC.SH | H1F1.WT.LC.SH |
| H1F1.M32 | JLHC1.A.HC.SH | JLHC1.A.LC.SH |
| H1F1.M33 | HIFl.OM.A.HC.SH | HIFl.OM.A.LC.SH |
| H1F1.M34 | H1F1.H2 | H1F1.L4 |
| H1F1.M35 | H1F1.H6 | H1F1.WT.LC.SH |
| H1F1.M36 | H1F1.H6 | H1F1.L2 |
| H1F1.M37 | H1F1.H6 | H1F1.L4 |
| H1F1.M38 | H1F1.H7 | H1F1.L5 |
| H1F1.M39 | H1F1.H7 | H1F1.L6 |
| H1F1.M40 | H1F1.H8 | H1F1.L5 |
| H1F1.M41 | H1F1.H8 | H1F1.L6 |
| H1F1.M42 | H1F1.H2.J1 | H1F1.WT(A27VL) |
| H1F1.M43 | H1F1.H2.J1 | H1F1.L2 |
| H1F1.M44 | H1F1.H2.J1 | H1F1.L3 |
| H1F1.M45 | H1F1.H2.J1 | H1F1.L4 |
| H1F1.M46 | H1F1.H2.J1 | H1F1.L5 |
| H1F1.M47 | H1F1.H2.J1 | H1F1.L6 |
| H1F1.M48 | H1F1.H2 | H1F1.L3.J3 |
| H1F1.M49 | H1F1.H2.J1 | H1F1.L3.J3 |
| H1F1.M50 | H1F1.H6 | H1F1.L3.J3 |
| H1F1.M51 | H1F1.H7 | H1F1.L3.J3 |
| H1F1.M52 | H1F1.H8 | H1F1.L3.J3 |
| H1F1.M53 | H1F1.H2.J2 | H1F1.WT(A27VL) |
| H1F1.M54 | H1F1.H2.J2 | H1F1.L2 |
| H1F1.M55 | H1F1.H2.J2 | H1F1.L4 |
| H1F1.M56 | H1F1.H2.J2 | H1F1.L5 |
| H1F1.M57 | H1F1.H2.J2 | H1F1.L6 |
| H1F1.M58 | H1F1.H2 | H1F1.L3.J1 |
| H1F1.M59 | H1F1.H6 | H1F1.L3.J1 |
| H1F1.M60 | H1F1.H7 | H1F1.L3.J1 |
| H1F1.M61 | H1F1.H8 | H1F1.L3.J1 |
| H1F1.M62 | H1F1.H2.J1 | H1F1.L3.J1 |
| H1F1.M63 | H1F1.H2.J2 | H1F1.L3.J1 |
| H1F1.M64 | H1F1.H2.J1 | H1F1.WT.LC.SH |
| H1F1.M65 | H1F1.H2.J2 | H1F1.WT.LC.SH |
| H1F1.M66 | HIFl.WT.HC.SH | H1F1.L3.J1 |
| H1F1.M67 | HIFl.WT.HC.SH | H1F1.L3.J3 |
| H1F1.M68 | H1F1.H2.J2 | H1F1.L3.J3 |
| H1F1.M69 | H1F1.H2.J1 | H1F1.L3.J1 |
| H1F1.M70 | H1F1.H2.J2 | H1F1.L3.J1 |
| H1F1.M71 | H1F1.H8 | H1F1.L3.J1 |
| H1F1.M72 | H1F1.H2.J1 | H1F1.L3.J2 |
| H1F1.M73 | H1F1.H2.J2 | H1F1.L3.J2 |
| H1F1.M74 | H1F1.H8 | H1F1.L3.J2 |

TABLE 12

| mAb name (Clone) | Heavy Chain Variable Region SEQ ID NO: | Light Chain Variable Region SEQ ID NO: | Heavy Chain | | | Light Chain | | |
|---|---|---|---|---|---|---|---|---|
| | | | HCDR1 SEQ ID NO: | HCDR2 SEQ ID NO: | HCDR3 SEQ ID NO: | LCDR1 SEQ ID NO: | LCDR2 SEQ ID NO: | LCDR3 SEQ ID NO: |
| H1F1.M69 (H1F1.H2.J1/ H1F1.L3.J1) | 21 | 22 | 24 | 25 | 16 | 11 | 12 | 13 |
| H1F1.M74 (H1F1.H8/ H1F1.L3.J2) | 20 | 23 | 8 | 25 | 16 | 11 | 12 | 18 |

H1F1 Mutant Antibody Sequences

H1F1.H8
(SEQ ID NO: 20)
QVQLVQSGAQVKMPGESLKVSCKASGYTFDDYGMGWVRQAPGQCLEWMGW
ISPYTGRTNSSDKFQGRVTMTRDTSTSTAYMELRSLRSEDTAVYYCARDG
TYYDFWSGYFDNNAFDIWGQGTLVTVSS

H1F1.H2.J1
(SEQ ID NO: 21)
QVQLVQSGAQVKMPGESLKVSCKASGYTFTDYGMGWVRQAPGQGLEWMGW
ISPYTGRTNSSDKFQGRVTMTRDTSTSTAYMELRSLRSEDTAVYYCARDG
TYYDFWSGYFDNNAFDIWGQGTLVTVSS

H1F1.L3.J1
(SEQ ID NO: 22)
QSVVTQPPSVSGAPGQRVTISCSGSTSNIGNNYVSWYQQLPGTAPKLLIY
DNYKRPSGVPDRFSGSKSGTSASLAITGLQTEDEADYYCGTWDSSLNAWV
FGGGTKLTVL

H1F1.L3.J2
(SEQ ID NO: 23)
QSVVTQPPSVSGAPGQRVTISCSGSTSNIGNNYVSWYQQLPGTAPKLLIY
DNYKRPSGVPDRFSGSKSGTSASLAITGLQSEDEADYYCGSWESGSNAYK
FGGGTKLTVL

CDR1 of H1F1.H2.J1
(SEQ ID NO: 24)
GYTFTDYG

CDR2 of H1F1.H2.J1 and H!F1.H8
(SEQ ID NO: 25)
ISPYTGRT hIgG1_3mu
(SEQ ID NO: 26)
ASTKGPSVFPLAPSSKSTSGGTAALGCLVKDYFPEPVTVSWNSGALTSGV
HTFPAVLQSSGLYSLSSWT VPSSSLGTQTYICNVNHKPSNTKVDKKVEP
KSCDKTHTCPPCP APEAAGGPSVFLFPPKPKDTLMISRTPEVTCVVVDV
SHEDPEVKFNWYVDGVEVHNAKTKPREEQYNSTYRVVSVLTVLHQDWLNG
KEYKCAVSNKALPAPIEKTISKAKGQPREPQVYTLPPSRDELTKNQVSLT
CLVKGFYPSDIAVEWESNGQPENNYKTTPPVLDSGSFFLYSKLTVDKSR
WQQGNVFSCSVMHEALHNHYTQKSLSLSPGK Anti-AITR Antibody Purification Chromatography Column Preparation The column (20 ml-volume) was filled with 20% ethanol and washed once. The column was filled with binding buffer and washed once. Any remaining buffer was removed completely from the column using a pipette. 3-5 ml of 20% ethanol was added, and 1 ml of Mab Select SuRe LX resin was added slowly, with the amount of eluting ethanol was checked during the procedure. The procedure continued until all of 20% ethanol was drained and Select SuRe LX resin reached 2 ml.

Preparation of Antibody Mixture

The antibody mixture obtained from transfected Expi293 cells were centrifuged (10,000 rpm, 10 min), and cells and impurities were pelleted (10,000 rpm, 10 min). The supernatant was filtered using a 0.22 μm syringe filter.

Antibody Purification (for Open-Column)

20%) ethanol filled in the column packaged with Mab Select SuRe LX was drained completely, and the column was washed with 18 ml of Binding buffer once. The entire antibody mixture was loaded. The column was washed with 18 ml Binding buffer once. Once the buffer was drained completely, a 1.5 ml tube with 100 μï of the neutralization buffer was placed under the column, and antibodies attached to the column were purified using 1 ml of Elution buffer each time.

Antibody Purification (for FPLC)

The Mab select SURE (1 ml) column was connected to the FPLC and stabilized with buffer A (1×PBS). After stabilizing until no other peaks were detected, antibody binding was performed by applying the sample to the column at the flow rate of 1 ml/min. Apply Buffer A to the column until the UV graph increased from approximately 1500 mAU to 2000 mAU and decreased to below 10 mAU. After this, antibodies were eluted by applying Buffer B (0.1M glycine pH 3.0), and the elution peak was confirmed by the UV graph. The fraction of the applicable peak was obtained.

Antibody Dialysis

After antibody purification, 5μï of Bradford solution was added to 250 μï of the eluted sample for a color reaction, and the antibody product was concentrated to a volume between 1-1.5 ml using 4 units of Amicon Ultra filters. The concentrated antibody product was added to a conical tube with 43 ml of 1×DPBS in a Dialysis device and dialyzed using a shaker (120 rpm, 2 hr). This step was repeated 2 times by replacing with new 1×DPBS. The antibody product was moved from the dialysis device to a Spin-X centrifuge tube filter unit, centrifuged (10000 rpm, 2 min), put into a 2 ml storage glass bottle, and stored at −20° C. and −80° C. until use.

Example 10: Characterization of Improved Anti-AITR Antibodies

Determining AITR Binding Affinity of Improved Anti-AITR Antibodies

A cell line overexpressing AITR was cultured in complete medium (H-DMEM+10% FBS+1× Penicillin-Streptomycin) at 37° C. in a 5% $CO_2$ incubator. Subcultures were made every 3 days while monitoring the morphology, number, and growth rate of the cell line.

Once cells were prepared using a 1× Trypsin/EDTA solution of the cell line overexpressing AITR, cells were aliquoted at $5 \times 10^5$ per FACS tube. After adding 10 μg, 5 μg, 2.5 μg, or 1.25 μg of the H1F1 mutant antibody, the reaction was performed for 30 min at 4° C. After adding 3 ml of FACS buffer (1×DPBS+1% FBS), centrifugation, and washing, a secondary antibody (Goat Anti-Human DyLight® 488) was added and incubated at 2-8° C. for 30 minutes. After centrifuging and washing with 3 mL of FACS buffer, FACS analysis was performed after adding FACS storage buffer (1×DPBS+2.5% FBS). For controls, cells without antibodies, cells with secondary antibody only, and cells with AITR-PE antibody were used.

Example 11: Analysis of Binding Ability Between AITR Antigen and Anti-AITR Antibodies H1F1M69 and H1F1M74

This example assesses the ability of mutant anti-AITR antibodies to bind to an AITR antigen recognized by the parent antibody, H1F1. Surface plasmon resonance was used in order to determine the ability of mutant anti-AITR antibodies to bind to AITR.

A Biacore T200 with a CM5 sensor chip was run using HBS-EP running buffer at pH 7.4 and 3M magnesium chloride regeneration buffer. Anti-human IgG(Fc) antibodies were immobilized to the CM5 chip via amine coupling and 6 minute injections at a flow rate of 5 μL/ηιηυïe were performed with an immobilization buffer of 10 mM sodium acetate at pH 5.0. The capture antibodies tested were parent antibody H1F1 and mutant antibodies M69 and M74. Glutathione S-transferase (GST)-tagged AITR analyte was injected at concentrations of 3.12, 6.25, 12.5, 25, 50 and 100 nM, with an association time of 150 seconds and a dissociation time of 240 seconds. Regeneration was achieved with 3M magnesium chloride for 30 seconds and 1:1 74 binding was evaluated.

As shown in Table 12 below, H1F1 mutants M69 and M74 bound the GST-AITR analyte with an affinity comparable to that of the parent antibody H1F1.

TABLE 12

| Antibody | $K_D$ (M) |
| --- | --- |
| H1F1M69 | $6.574 \times 10^{-10}$ |
| H1F1M74 | $9.655 \times 10^{-10}$ |
| H1F1 | $7.892 \times 10^{-10}$ |

Figure 16A:
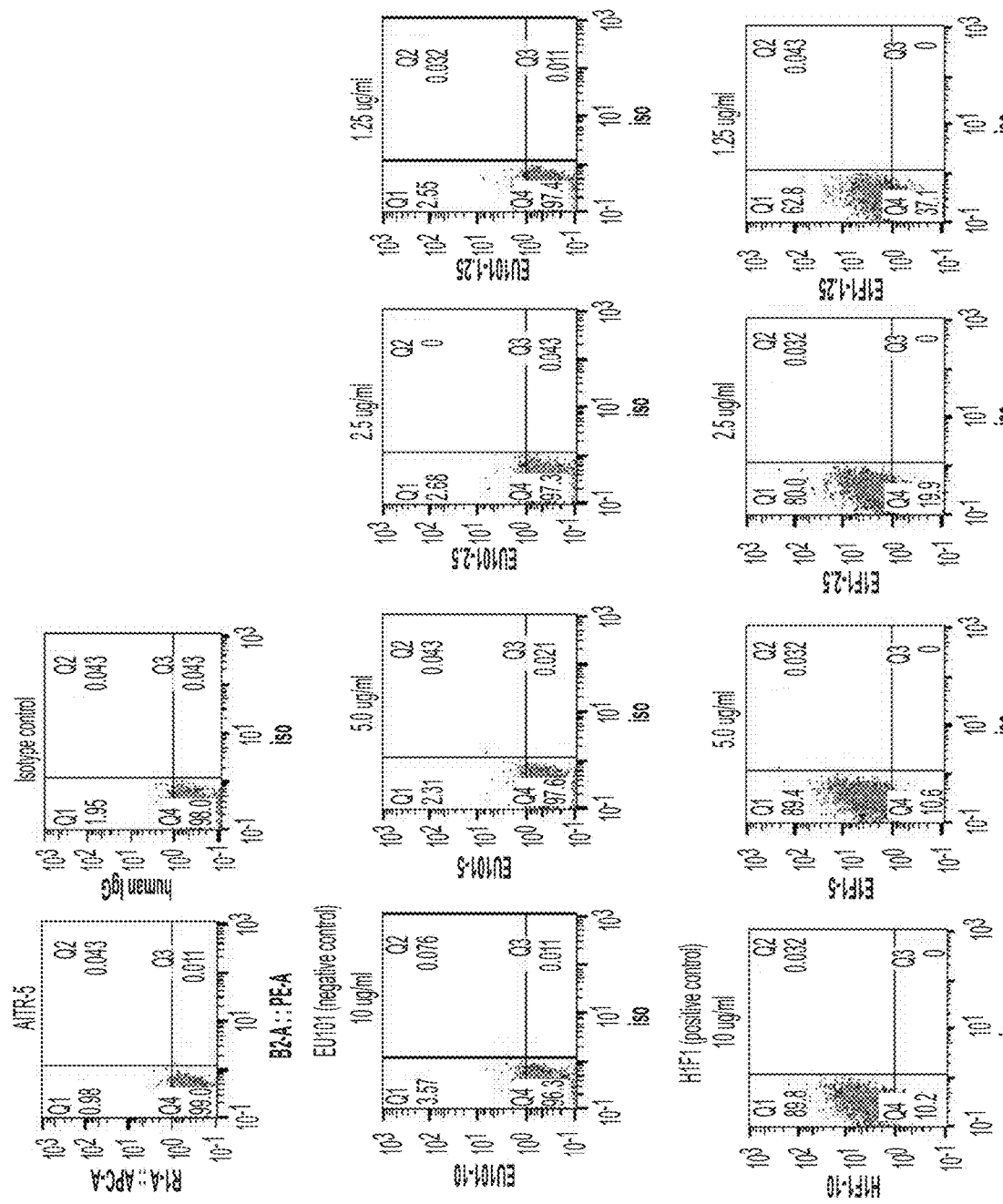
FIG. 16A depicts binding of H1F1 to AITR-5 at concentrations of 10, 5, 2.5 and 1.25 µg/mL, as compared to the negative control mAb EU1O1, which did not bind to AITR-5.
Figure 16B:
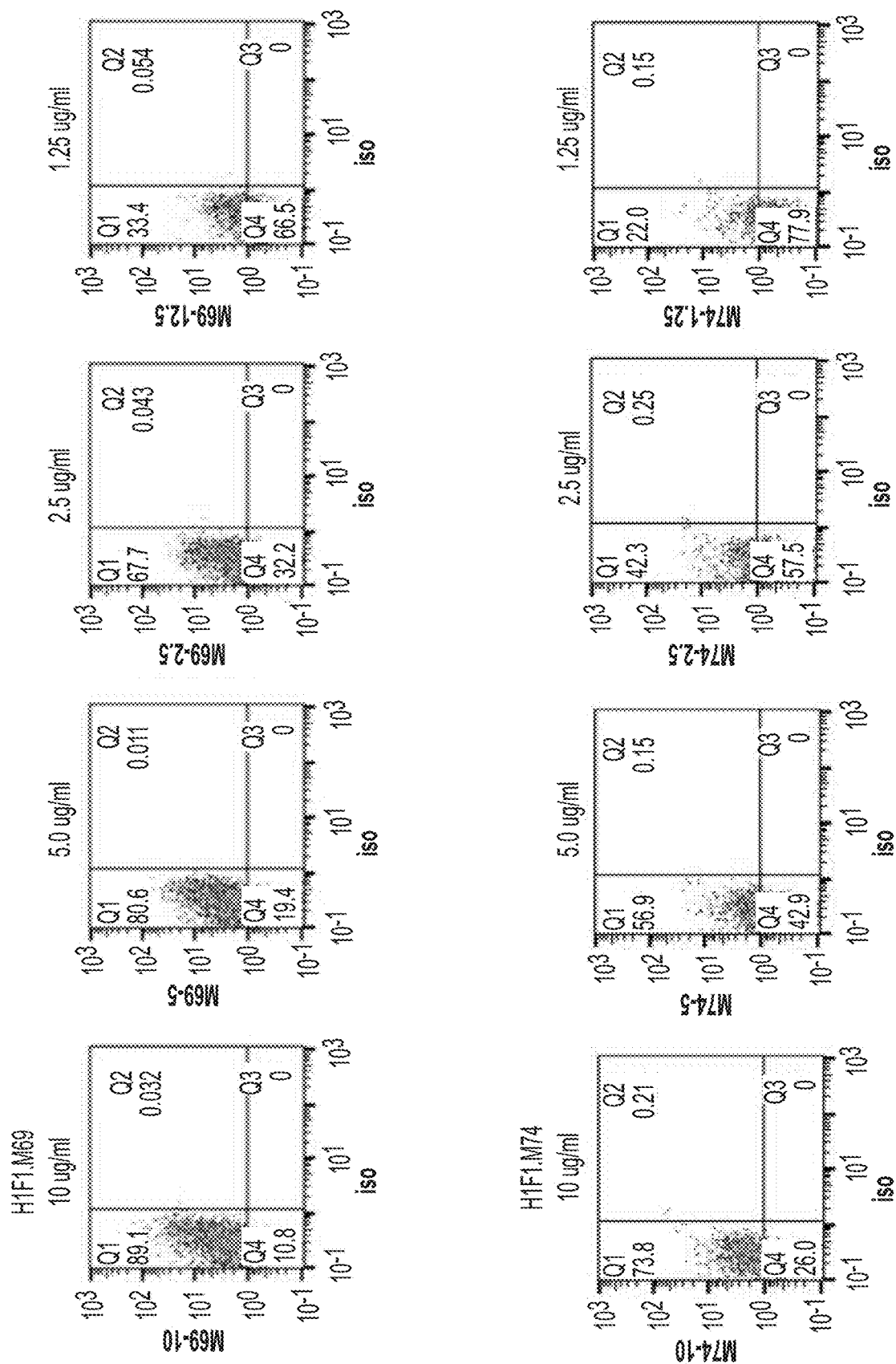
FIG. 16B depicts binding of H1F1M69 and H1F1M74 to AITR-5 in a dose dependent manner.

The anti-AITR antibodies M69 and M74 were further analyzed for binding to AITR using a HEK293 cell line that overexpressed human AITR (AITR-5). As shown in FIG. 16A, the negative control mAb EU101 did not bind to AITR-5 (3.6%), while 89.8% of AITR-5 cells were stained with H1F1 in 10 μg/mL of concentration. Additionally, as shown in FIG. 16B, 89.1% of AITR-5 cells were stained with M69 and 73.8% of the cells were stained with M74.

These data indicate that H1F1, M69 and M74 all bind to the human AITR molecule that was expressed on the cell surface in a dose dependent manner.

Example 12: Effect of Anti-AITR Antibodies H1F1M69 and H1F1M74 on $nT_{reg}$ Cells (Regulatory T Cells)

In this example, mutant anti-AITR antibodies were tested for their ability to convert $nT_{reg}$ $nT_r$ cells to $T_H1$ cells.

Peripheral blood mononuclear cells (PBMCs) were collected via Ficoll-Paque density gradient centrifugation and then FACS was used to isolate $CD4^+CD25^{++}CD127^-$ ($nT_{reg}$) cells. The $nT_{reg}$ cells were then treated for 5 days with 100 U/mL IL-2 every 2-3 days and with monoclonal antibodies H1F1M69, H1F1M74, TRX518, and MK4166 at concentrations of 2.5 and 10 μg/mL, with 10 μg/mL of hIgG used as a negative control. After the 5 days of treatment, the cells were tested for intracellular staining of IFN-γ and by ELISA for IFN-γ and TGF-β secretion.

Figure 17:
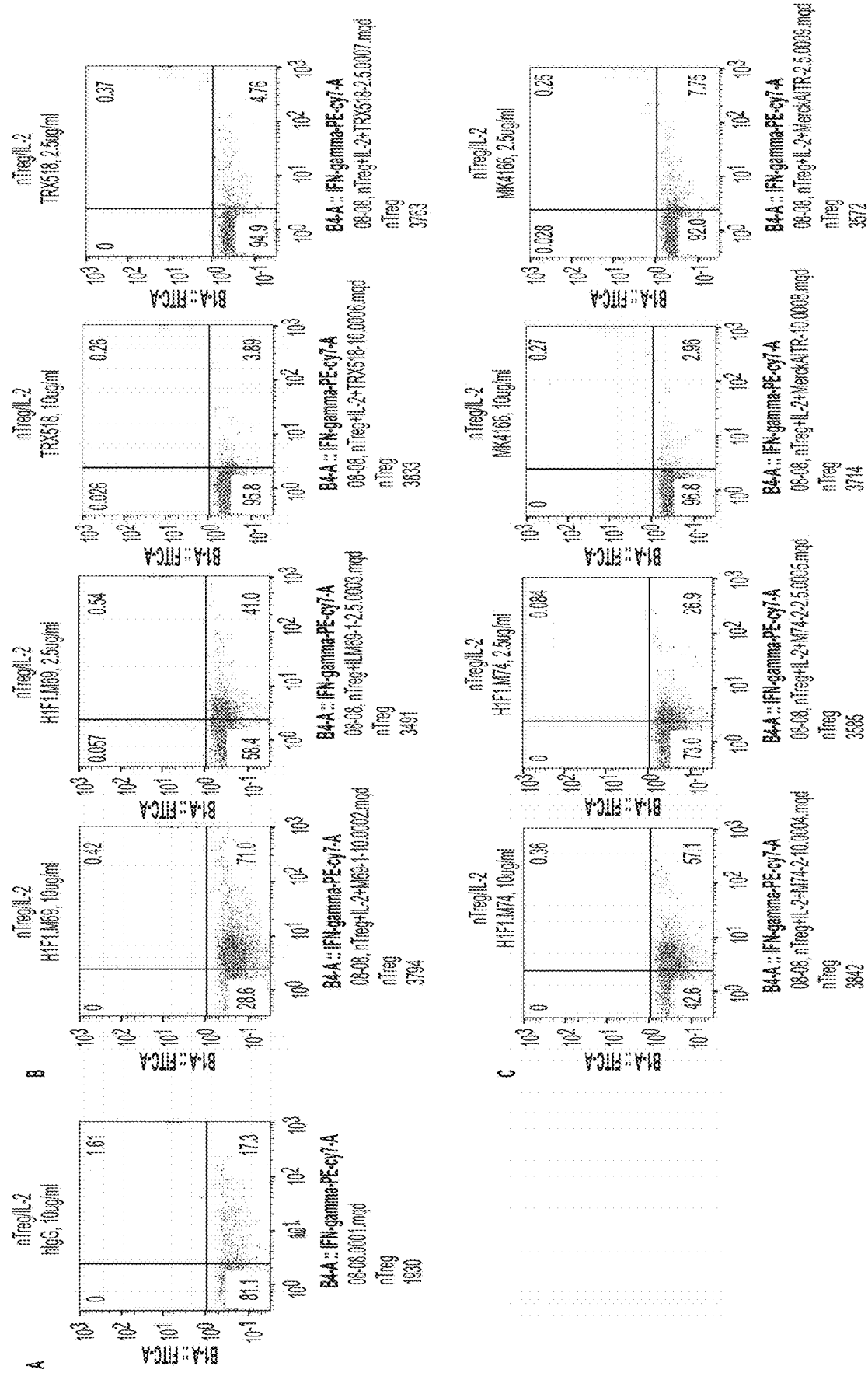
FIG. 17 depicts the conversion of $nT_{reg}$ cells to $T_H1$-like cells upon stimulation with H1F1M69 (B) and H1F1M74 (C) relative to an hIgG control (A). The numbers in each panel indicate the percentage of positive cells.

As shown in FIG. 17, the $nT_{reg}$ cells were converted to $T_H1$-like cells upon stimulation with H1F1M69 and H1F1M74. 71% of $T_{reg}$ were converted to IFN-γ-positive cells by M69 and 57% of $T_{reg}$ were converted to IFN-γ-positive cells by M74. The numbers in each panel indicate the percentage of positive cells.

Figure 18:
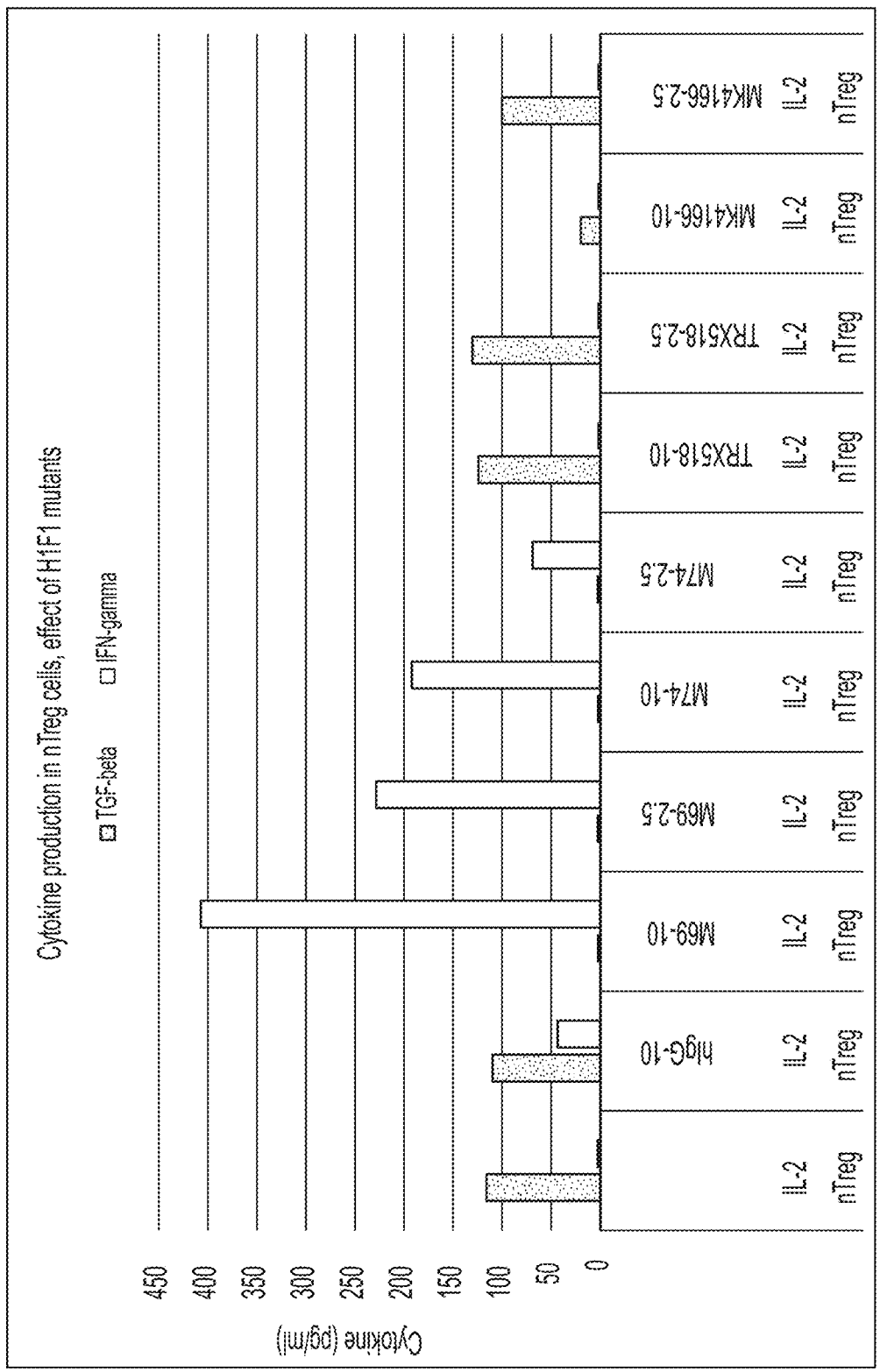
FIG. 18 depicts a graph quantifying the dose-dependent effect of H1F1M69 and H1F1M74 on TGF-β and IFN-γ in $nT_{reg}$ cells.

For testing secretion of IFN-γ and TGF-β from T cells after stimulation with IL-2 and anti-AITR antibodies, culture supernatants were used to measure IFN-γ and TGF-β. The graph in FIG. 18 summarizes the results obtained by ELISA assay. H1F1M69 and H1F1M74 stimulated secretion of the $T_H1$ cytokine, IFN-γ (gray bars) and, conversely, lead to decreased secretion of the $T_{reg}$ cytokine, TGF-β (black bars). $5 \times 10^4$ $nT_{reg}$ cells per well were used for this assay.

Example 13: Effect of Anti-AITR Antibodies H1F1M69 and H1F1M74 on $iT_{reg}$ Cells (Inducible Regulatory T Cells)

In this example, mutant anti-AITR antibodies were tested for their ability to convert inducible $T_{reg}$ ($iT_{reg}$) cells to $T_H1$ cells.

Peripheral blood mononuclear cells (PBMCs) were collected via Ficoll-Paque density gradient centrifugation and then magnetic-activated cell sorting (MACS) with CD4 microbeads (Miltenyi) was used to isolate $CD4^+$ T cells according to the manufacturer's instructions. The $CD4^+$ T cells were then stimulated for 6 days with anti-CD3/anti-CD28 beads (25 μL, Invitrogen), 100 U/mL IL-2 (Novartis) and 5 ng/mL TGF-βI. After the 6 days of stimulation, the cells were then stained for CD4-BB515 and Foxp3-APC. The CD3/CD28 beads were then removed via MACS. The $CD4^+$ T cells were then treated for 5 days with 100 U/mL IL-2 every 2-3 days and with monoclonal antibodies H1F1M69, H1F1M74, TRX518, and MK4166 at concentrations of 2.5, 5, and 10 μg/mL, with 10 μg/mL of hIgG used as a negative control. After the 5 days of treatment, the cells were tested for intracellular staining of IFN-γ and by ELISA for IFN-γ and TGF-β secretion.

Figure 19:
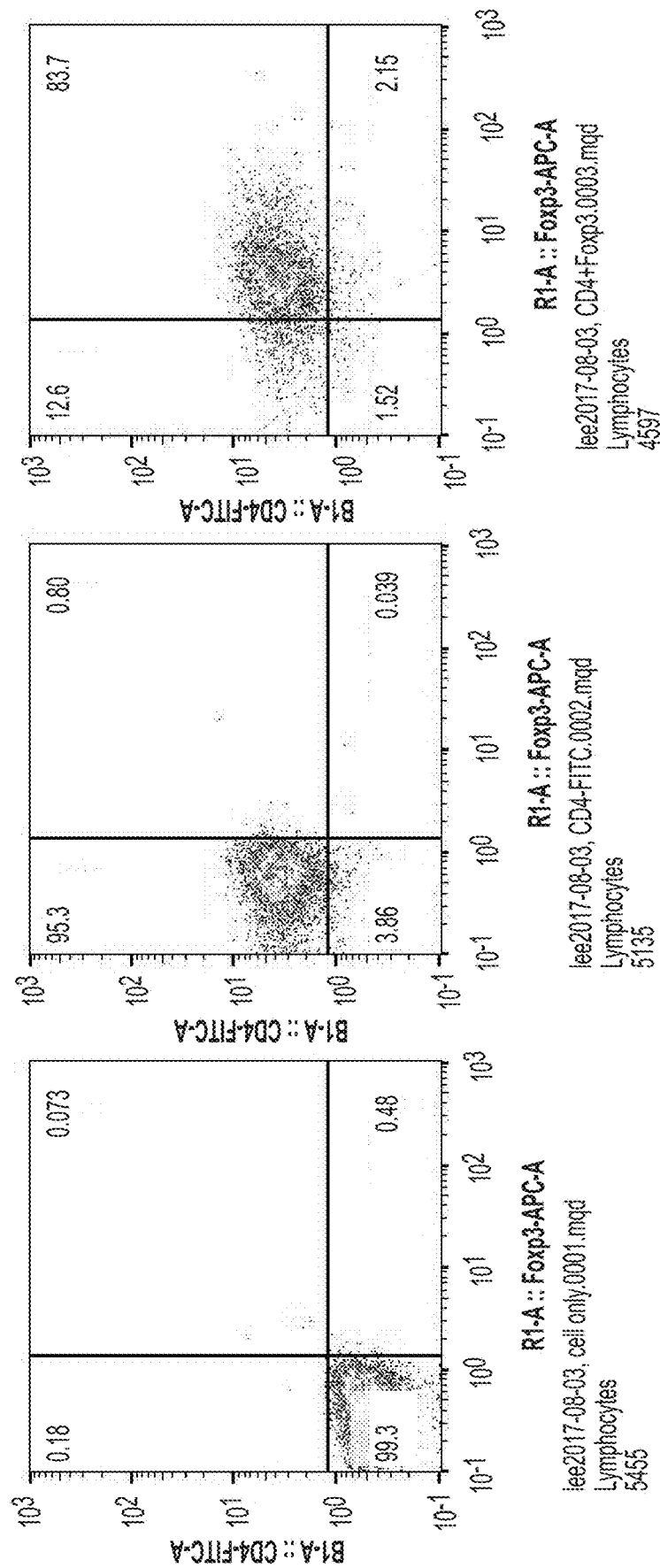
FIG. 19 depicts the generation of $iT_{reg}$ cells from $CD4^+$ T cells after stimulation with anti-CD3, CD28 beads, IL-2 and TGF-β for 6 days.

The transcription factor forkhead box protein P3 (Foxp3) is a specific marker of regulatory T cells and plays a pivotal role in the suppressive activity of $nT_{reg}$ and $iT_{reg}$ cells. To evaluate effect of AITR signaling in $T_{reg}$, regulatory T cells were induced in vitro and Foxp3 expression was measured. As shown in FIG. 19, $iT_{reg}$ cells were generated from the $CD4^+$ T cells after stimulation with anti-CD3, CD28 beads, IL-2 and TGF-β for 6 days. 83.7% of $iT_{reg}$ were confirmed by Foxp3-positive staining (right panel). These data indicate that the CD4+ T cell population was differentiated into iTreg by the conditions described above.

Figure 20:
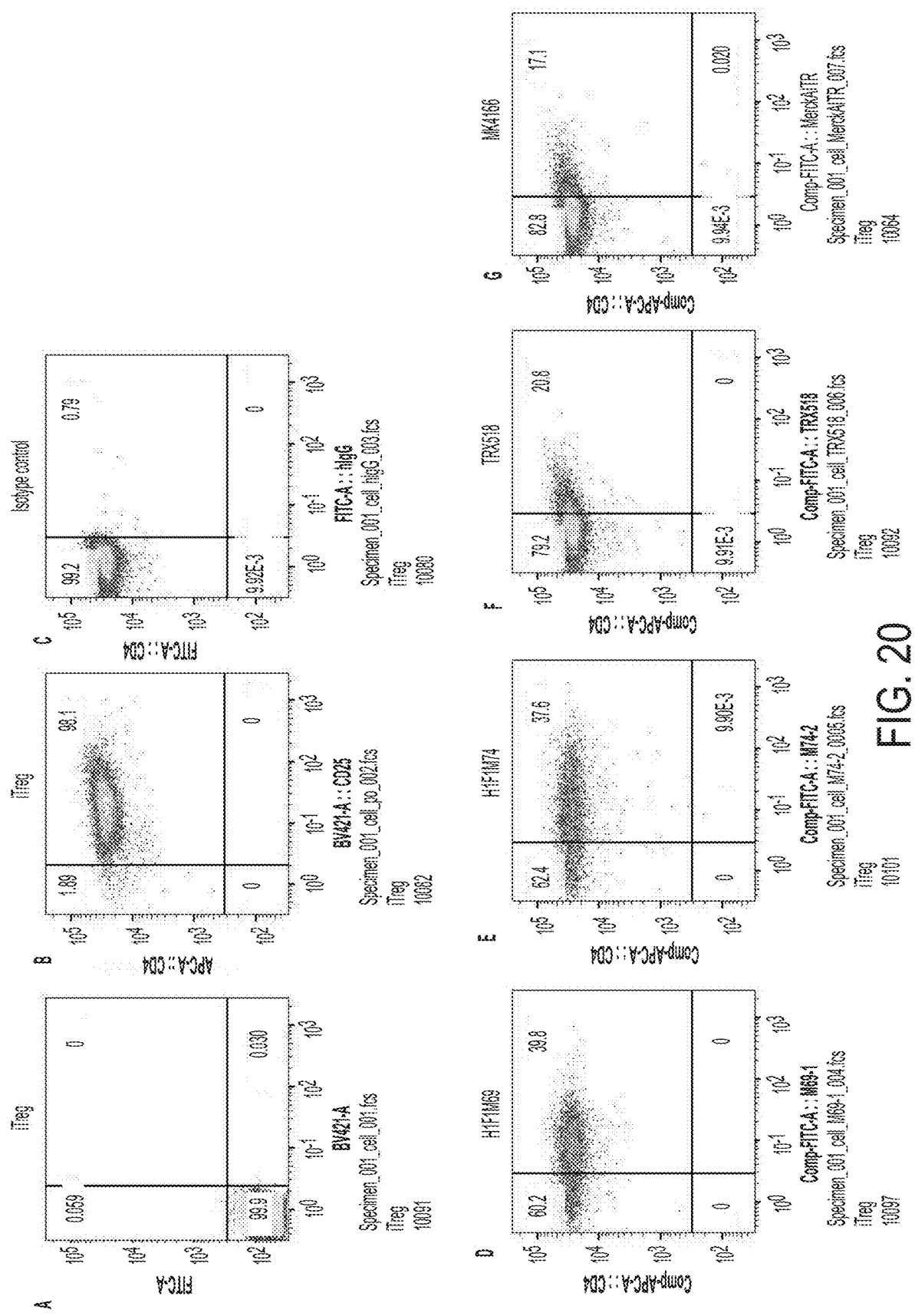
FIG. 20 depicts the binding efficiency of H1F1M69 and H1F1M74 for AITR on iTreg cells. Panels A and B illustrate gating parameters. Panel C illustrates an isotype control. Panels D-G show that surface AITR was detected by H1F1M69 (D) and H1F1M74 (E) more frequently than by competitor's anti-AITR antibodies TRX518 (F) and MK4166 (G).

Although AITR expression on CD4+ T cells is dependent on activation, naive or inducible regulatory T cell express AITR constitutively. Prior to measuring Foxp3 expression, the binding efficiency of H1F1 for AITR on $iT_{reg}$ cells was determined. As shown in FIG. 20, surface AITR was detected by mutant H1F1 antibodies (M69—panel D and M74—panel E). Furthermore, H1F1M69 and H1F1M74 recognized approximately 39% of the cells as positive for human AITR, which was more frequently than competitor's anti-AITR antibodies (19% of cells in average—FIG. 20, panels F and G).

Figure 21:
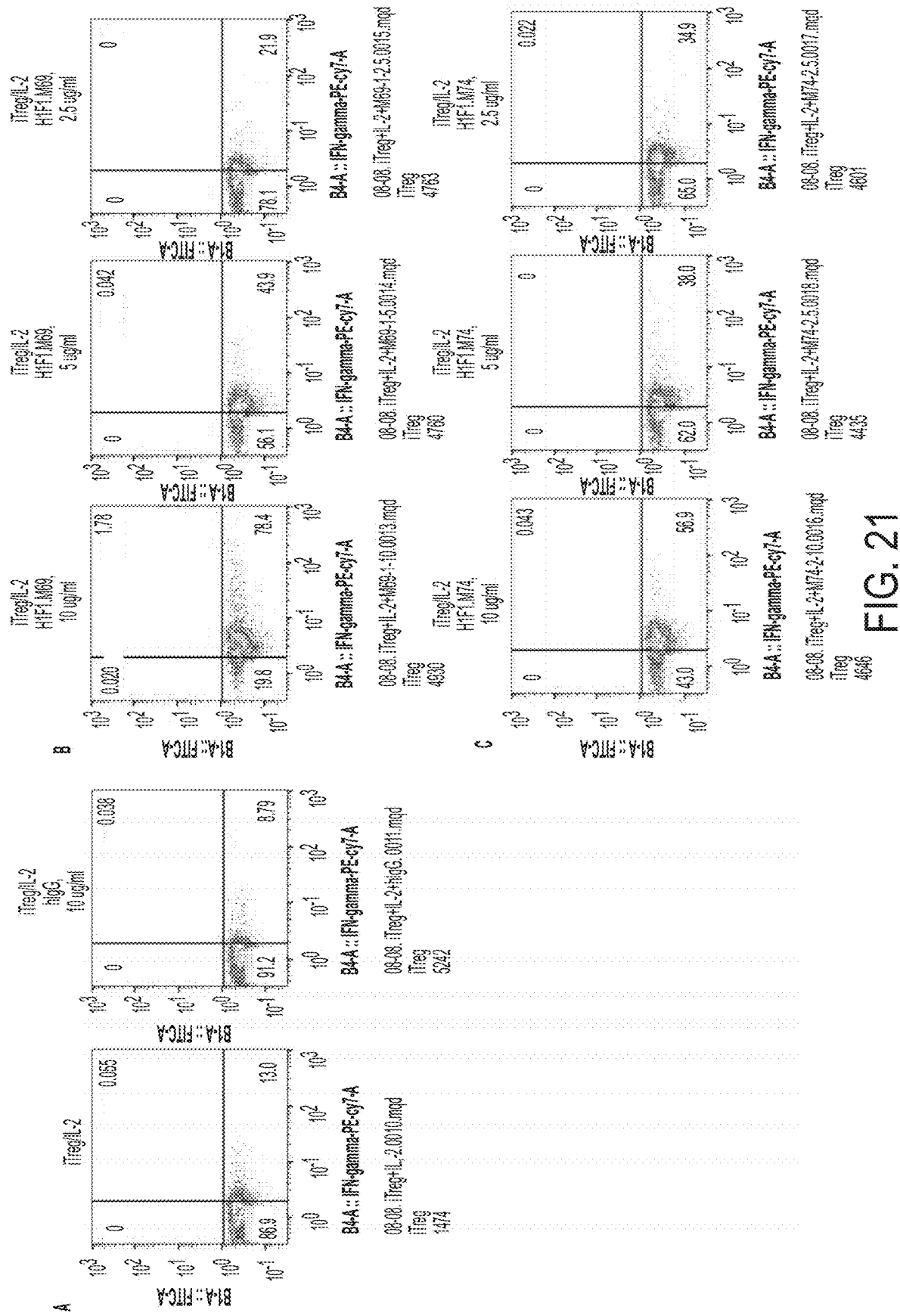
FIG. 21 depicts the conversion of $iT_{reg}$ cells to $T_H1$-like cells upon stimulation anti-AITR antibodies. Panel A show an hIgG control. Panels B-E show the effect of H1F1M69 (B), H1F1M74 (C), TRX518 (D) and MK4166 (E) on $iT_{reg}$ cells.
Figure 21:
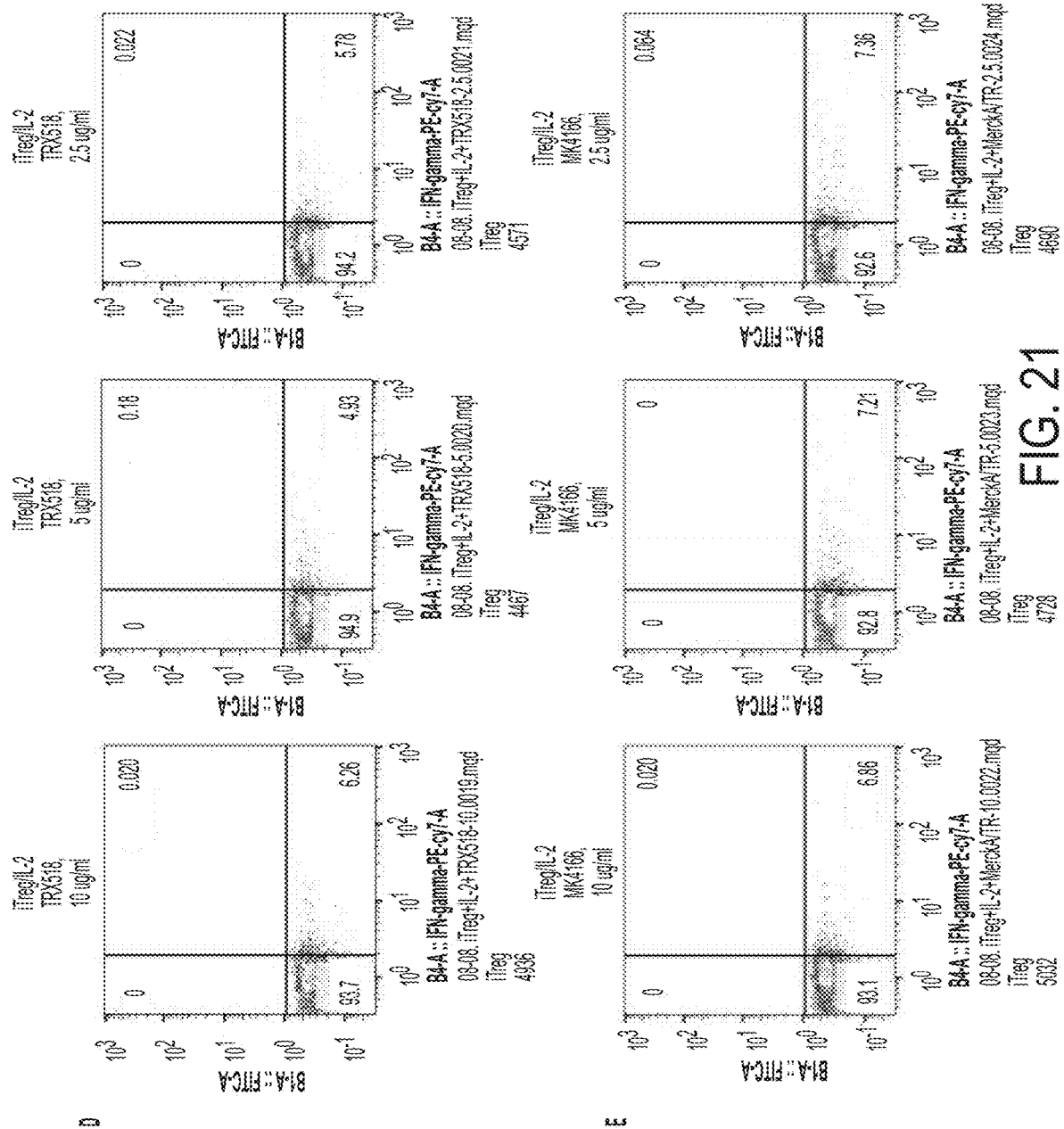

Additionally, as shown in FIG. 21, the $iT_{reg}$ cells were converted to $T_H1$-like cells upon stimulation with H1F1M69 and H1F1M74. 78% of $iT_{reg}$ were converted to IFN-γ-positive cells by M69 and 57% of $iT_{reg}$ were converted to IFN-γ-positive cells by M74. The numbers in each panel indicate the percentage of positive cells.

Figure 22:
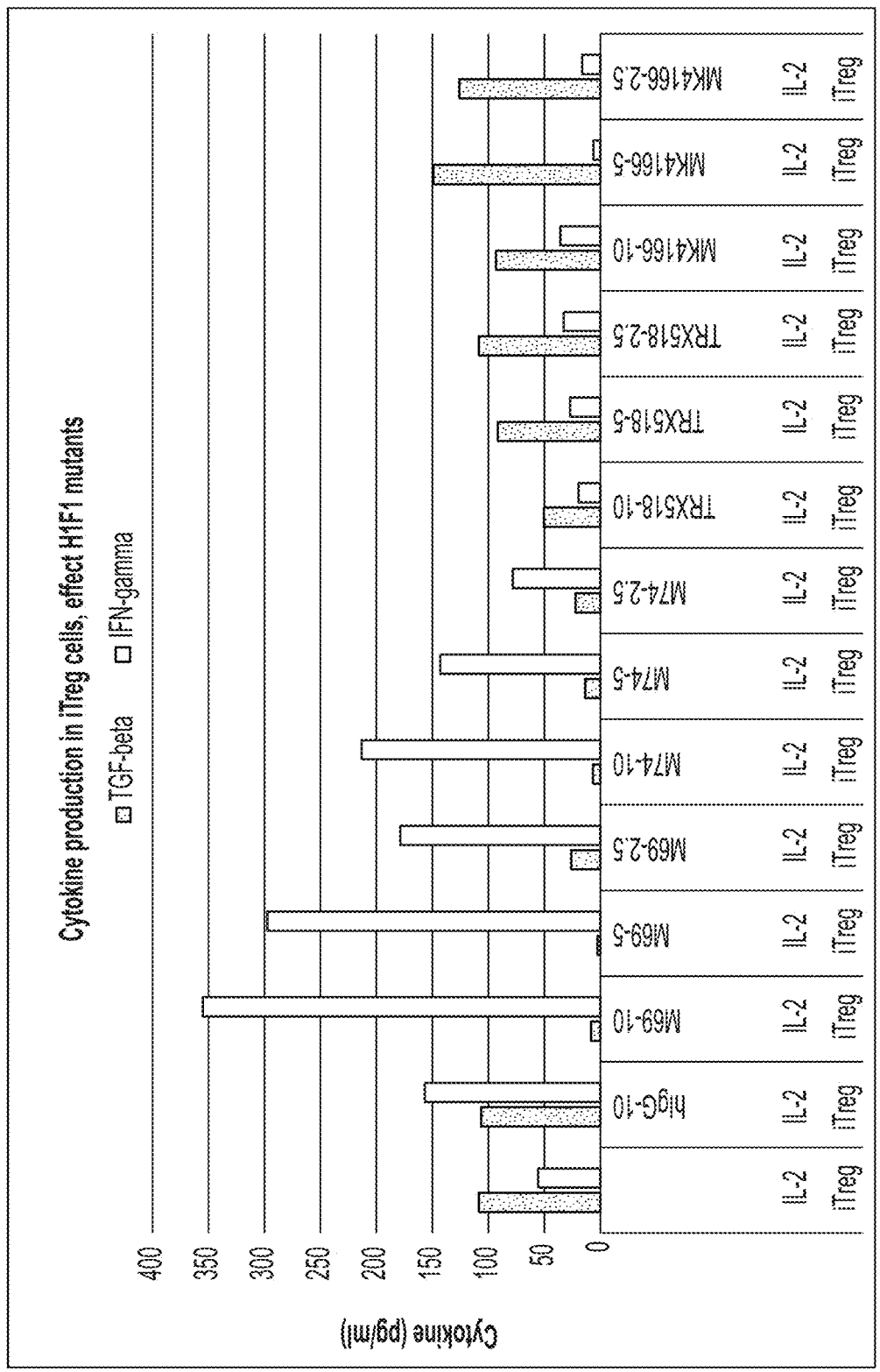
FIG. 22 depicts a graph quantifying the dose-dependent effect of H1F1M69 and H1F1M74 on TGF-β and IFN-γ in $iT_{reg}$ cells.

For testing secretion of IFN-γ and TGF-β from T cells after stimulation with IL-2 and anti-AITR antibodies, culture supernatants were used to measure IFN-γ and TGF-β. The graph in FIG. 22 summarizes the results obtained by ELISA assay. H1F1M69 and H1F1M74 stimulated secretion of the $T_H1$ cytokine, IFN-γ (gray bars) and, conversely, lead to decreased secretion of the $T_{reg}$ cytokine, TGF-β (black bars). $1 \times 10^5$ $iT_{reg}$ cells per well were used for this assay.

Example 14: Effect of Immobilized Anti-AITR Antibodies H1F1M69 and H1F1M74 on $iT_{reg}$ Cells (Inducible Regulatory T Cells)

In this example, immobilized mutant anti-AITR antibodies were tested for their ability to convert inducible $T_{reg}$ ($iT_{reg}$) cells to $T_H1$ cells.

Peripheral blood mononuclear cells (PBMCs) were collected via Ficoll-Paque density gradient centrifugation and then magnetic-activated cell sorting (MACS) with CD4 microbeads (Miltenyi) was used to isolate CD4+ T cells according to the manufacturer's instructions. The CD4+ T cells were then stimulated for 6 days with anti-CD3/anti-CD28 beads (25 µL, Invitrogen), 100 U/mL IL-2 (Novartis) and 5 ng/mL TGF-βI. After the 6 days of stimulation, the cells were then stained for CD4-BB515 and Foxp3-APC. The CD3/CD28 beads were then removed via MACS. The CD4+ T cells were then treated over 5 days with 100 U/mL IL-2 every 2-3 days and with immobilized monoclonal antibodies M69 and M74 at concentrations of 2.5, 5, and 10 µg/mL for approximately 1 day. After the 5 days of treatment, the cells were tested for intracellular staining of IFN-γ and by ELISA for IFN-γ and TGF-β secretion.

Figure 23:
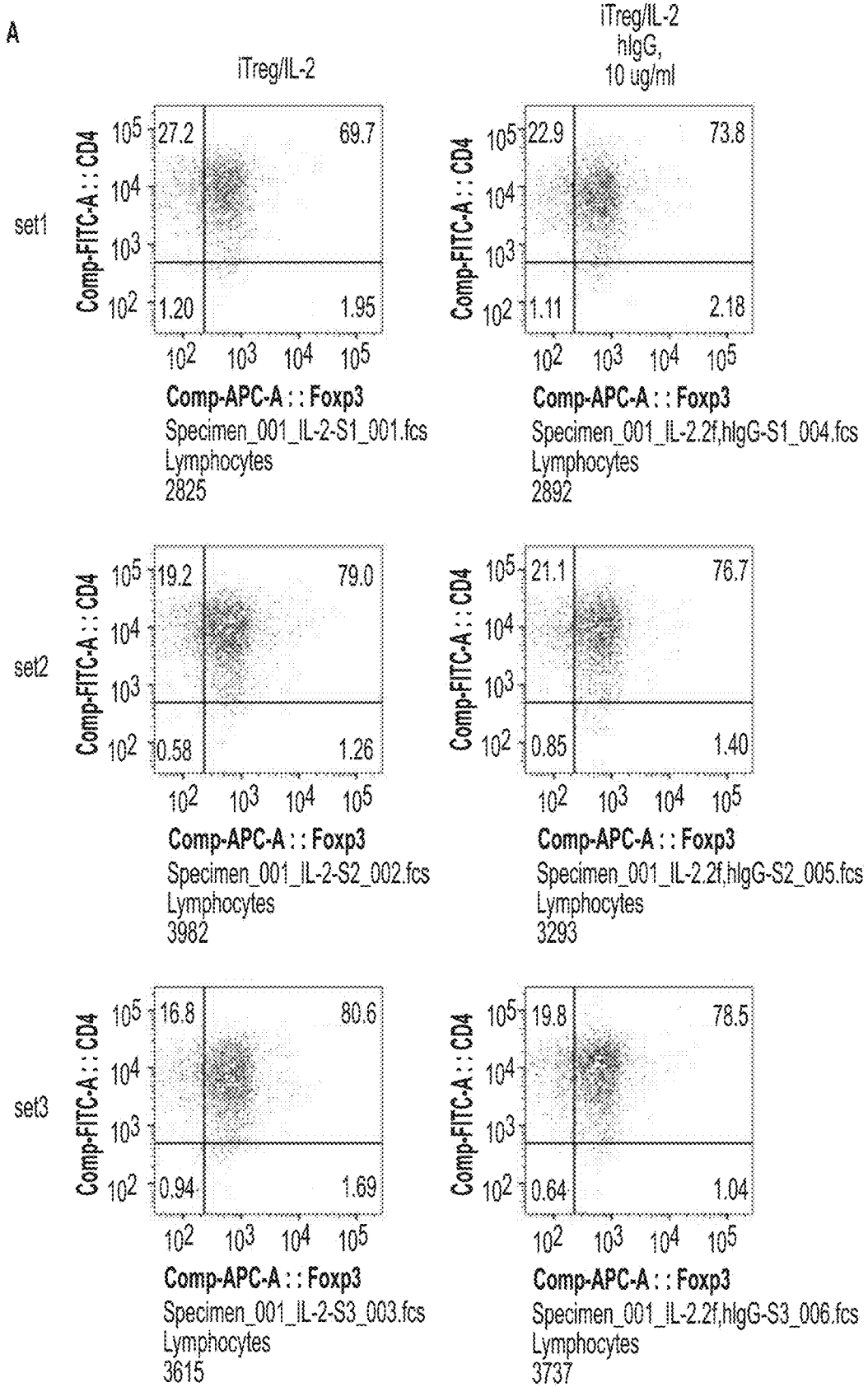
FIG. 23 depicts the effect of immobilized monoclonal antibodies hIgG (A), H1F1M69 (B), H1F1M74 (C), TRX518 (D) and MK4166 (E) on Foxp3 in $iT_{reg}$ cells.
Figure 23:
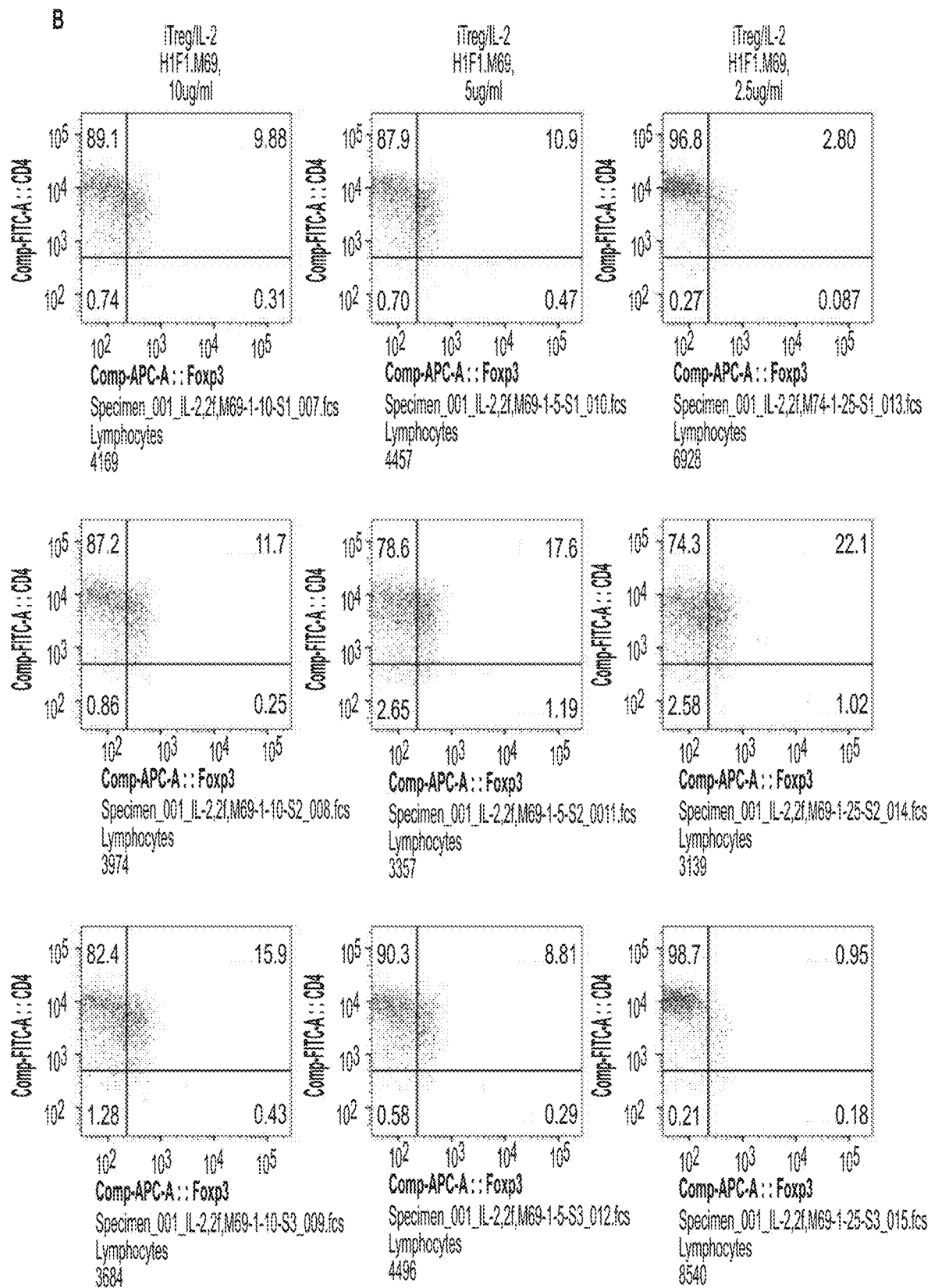
Figure 23:
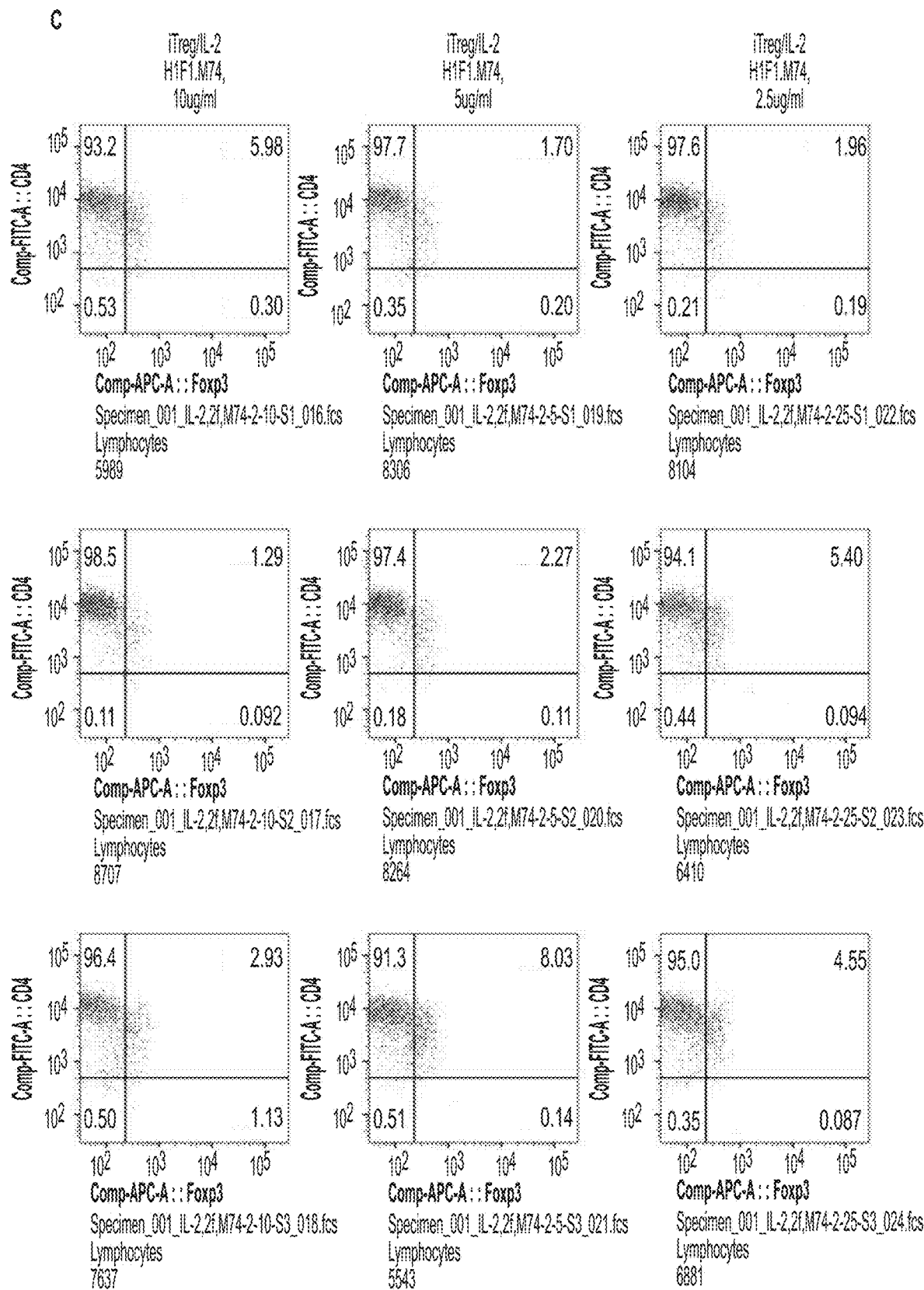
Figure 23:
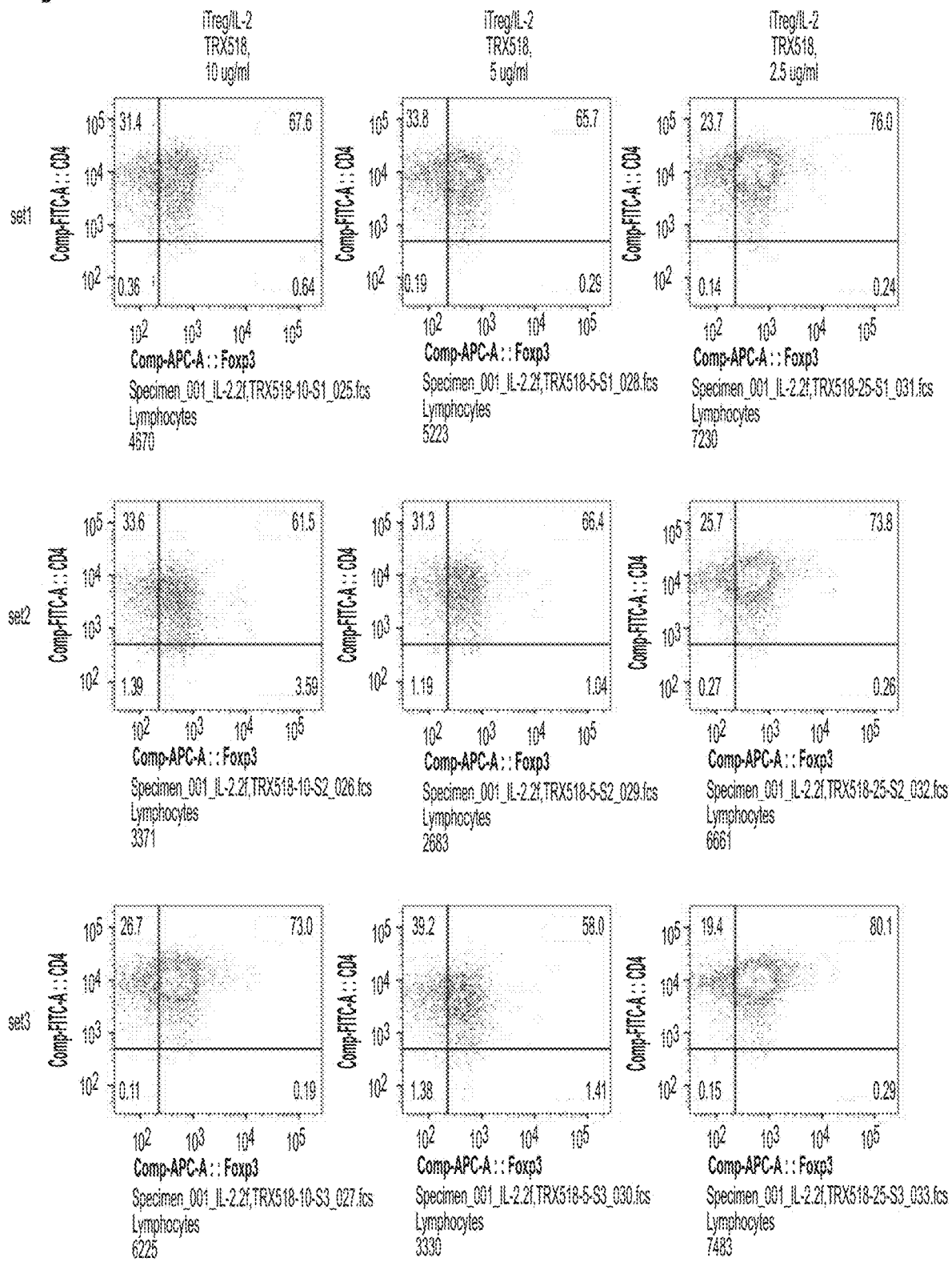
Figure 23:
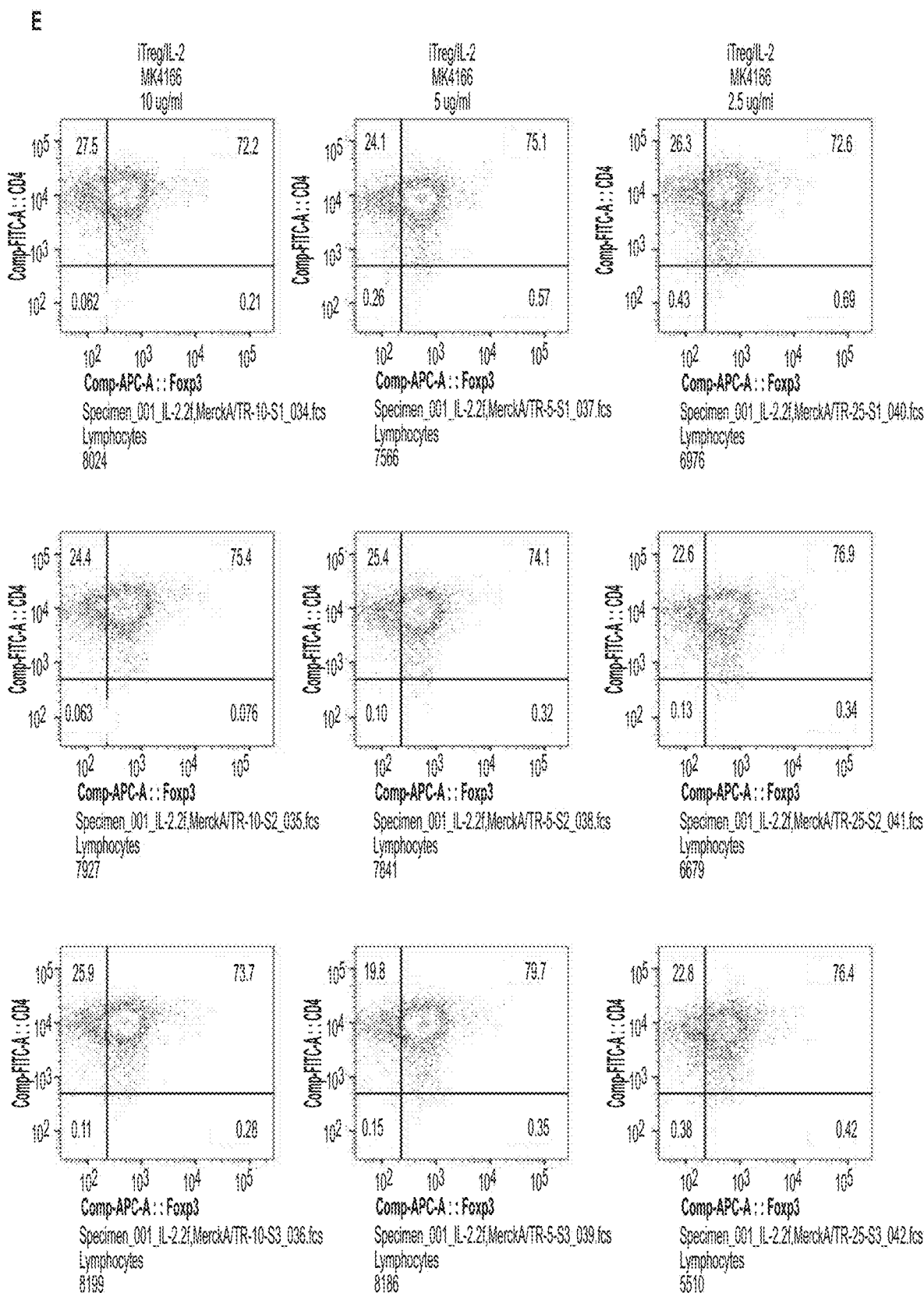

Since down-regulation of Foxp3 reduces suppressive activity of $iT_{reg}$, $iT_{reg}$ cells were prepared and the effect of H1F1M69 and H1F1M74 on expression of Foxp3 was evaluated. As described above, to created $iT_{reg}$ cells, CD4+ T cells were stimulated with anti-CD3 and anti-CD28 beads and polarized to $iT_{reg}$ in vitro. As shown in FIG. 23 (panels B and C), immobilized H1F1M69 and H1F1M74 inhibited expression of Foxp3 in $iT_{reg}$. In addition, although TRX518 or MK4166 failed to reduce Foxp3 expression (FIG. 23, panels D and E), H1F1M69 and H1F1M74 decreased Foxp3 expression even at their lowest concentrations (2.5 µg/mL). Thus, H1F1M69 and H1F1M74 induced loss of Foxp3, which is an essential transcription factor for maintaining immune-suppressive activity of regulatory T cell.

Figure 24:
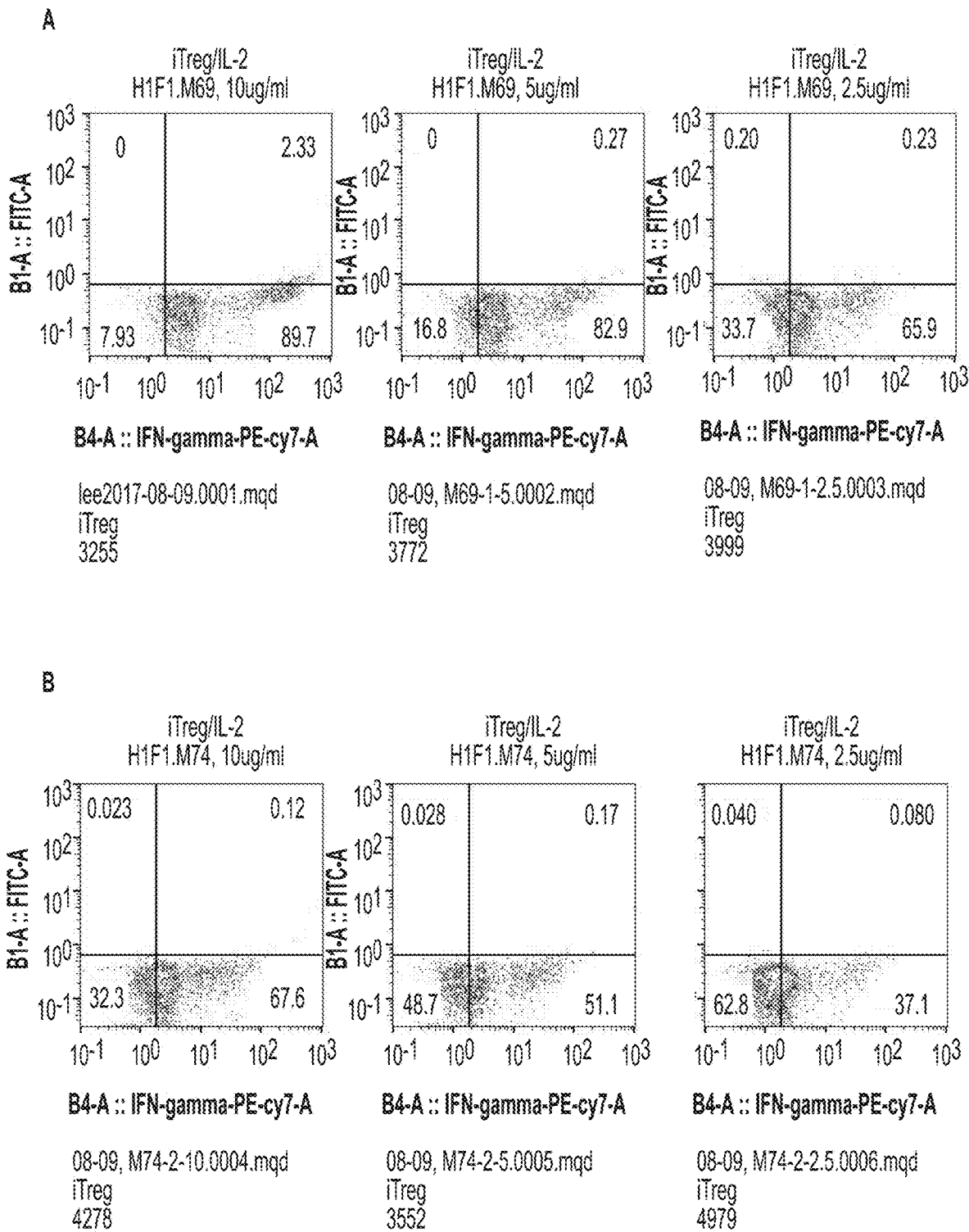
FIG. 24 depicts the conversion of $iT_{reg}$ cells to $T_H1$-like cells after being added to wells coated with IL-2 and H1F1M69 (A) or H1F1M74 (B). The numbers in each panel indicate the percentage of positive cells.

As shown in FIG. 24, the $iT_{reg}$ cells were converted to $T_H1$-like cells after being added to wells coated with IL-2 and the anti-AITR antibodies H1F1M69 and H1F1M74. 90% of $iT_{reg}$ were converted to IFN-γ-positive cells by M69 and 68% of $iT_{reg}$ were converted to IFN-γ-positive cells by M74 in a dose-dependent manner. The numbers in each panel indicate the percentage of positive cells.

Example 15: Effect of Anti-AITR Antibodies M69 and M74 on $T_{eff}$ Cells (Effector T Cells)

In this example, mutant anti-AITR antibodies were tested for their ability to convert $T_{eff}$ cells to $T_H1$ cells.

Whole blood was collected from healthy donors and PBMCs were separated out in the buffy coat by Ficoll-Paque density gradient centrifugation. PBMCs were collected from the interface between the plasma layer and the Ficoll-RBC layer and washed with RPMI1640 media. PBMCs were resuspended with pre-sorting buffer and stained with anti-human CD4, anti-CD25 and anti-CD127. CD4+CD25−CD127+ ($T_{eff}$) cells were sorted by FACS.

Figure 25:
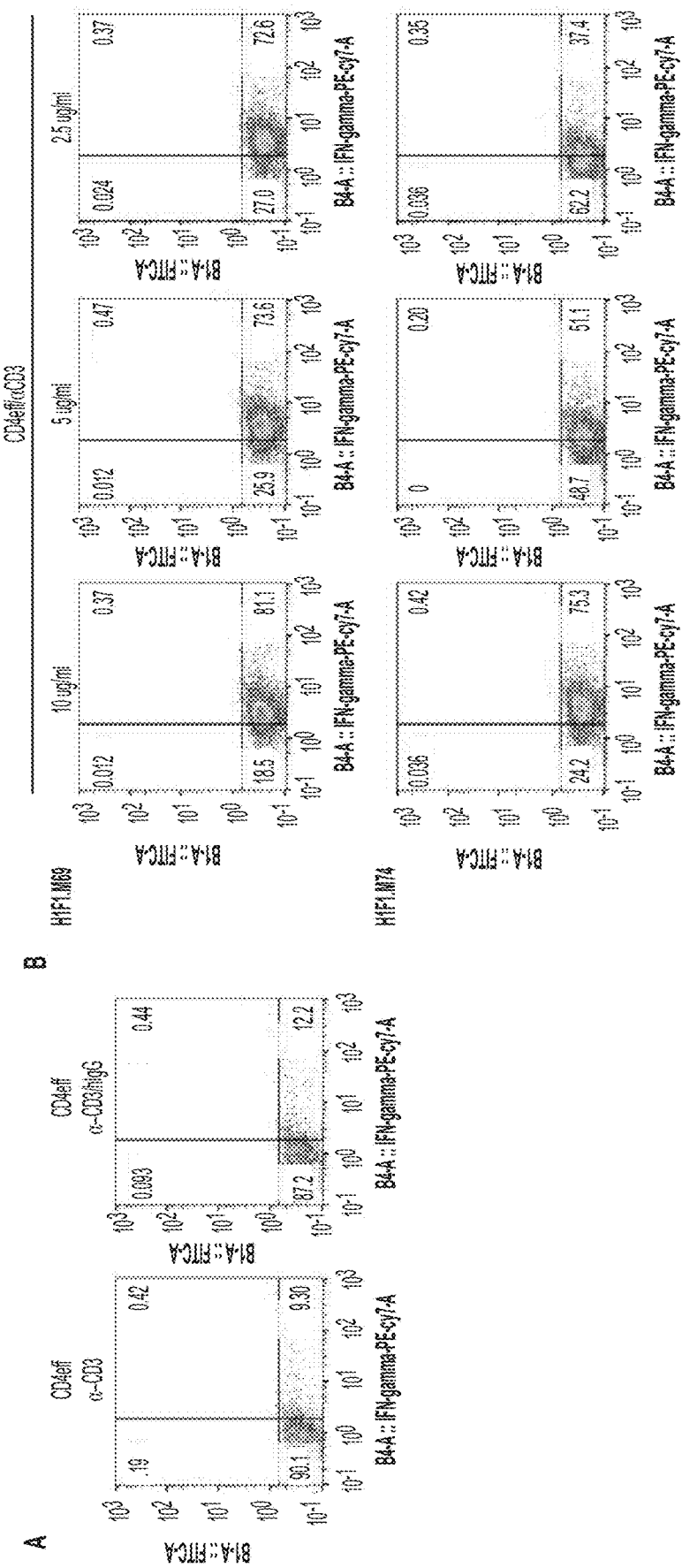
FIG. 25 depicts the polarization of $T_{eff}$ cells to $T_H1$ cells after treatment with antibodies. Panel A shows the effect of a control hIgG. Panel B shows the effect of H1F1M69 and H1F1M74. Panel C shows the effect of antibodies TRX518 and MK4166.
Figure 25:
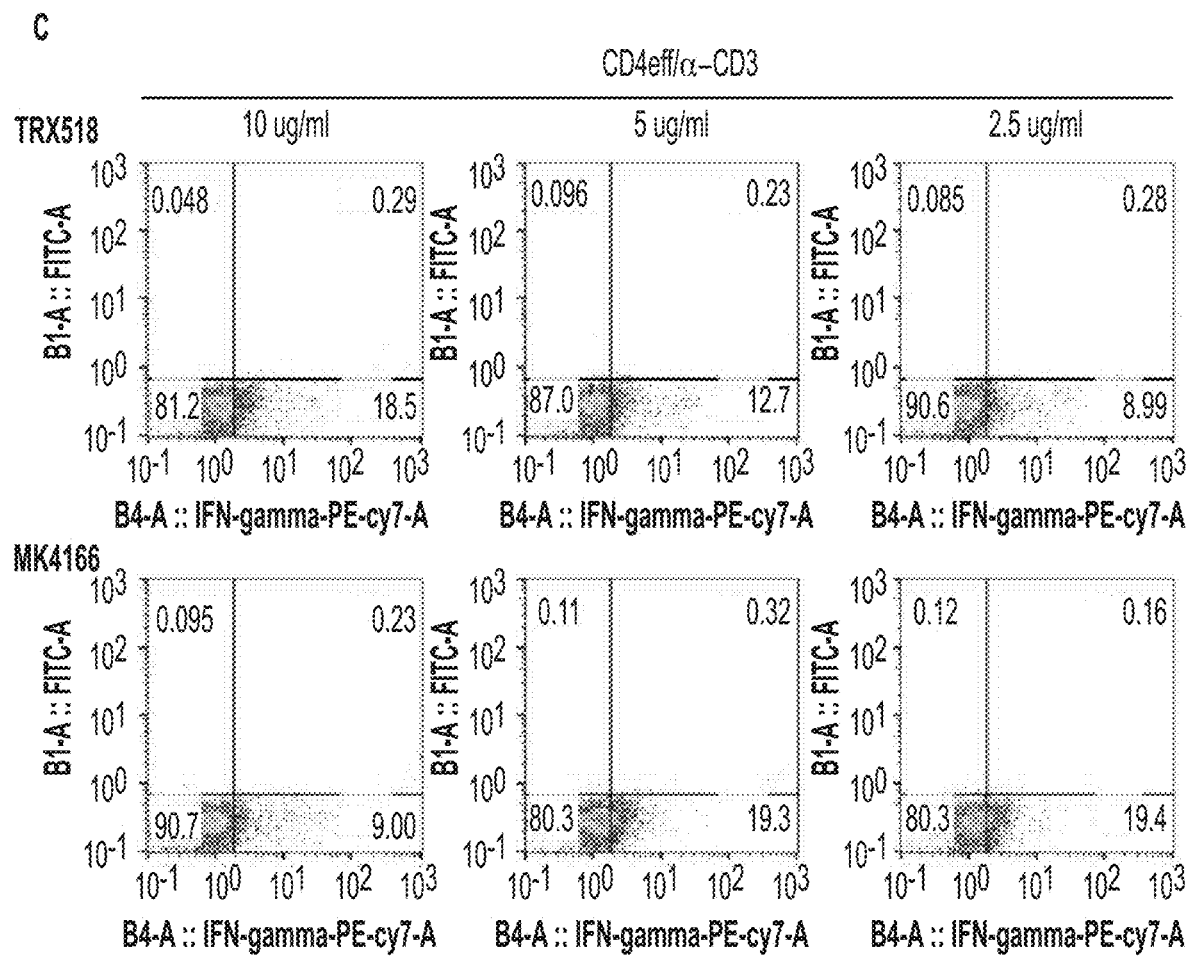

As shown in FIG. 25, the anti-AITR antibodies H1F1M69 and H1F1M74 polarized the $T_{eff}$ cells to $T_H1$ cells. 81.1% of $T_{eff}$ cells were polarized to IFN-γ-positive cells by H1F1M69 (10 µg/mL) and 75.3% of $T_{eff}$ cells were polarized to IFN-γ-positive cells by H1F1M74 (10 µg/mL). The numbers in each panel indicate the percentage of positive cells.

Figure 26:
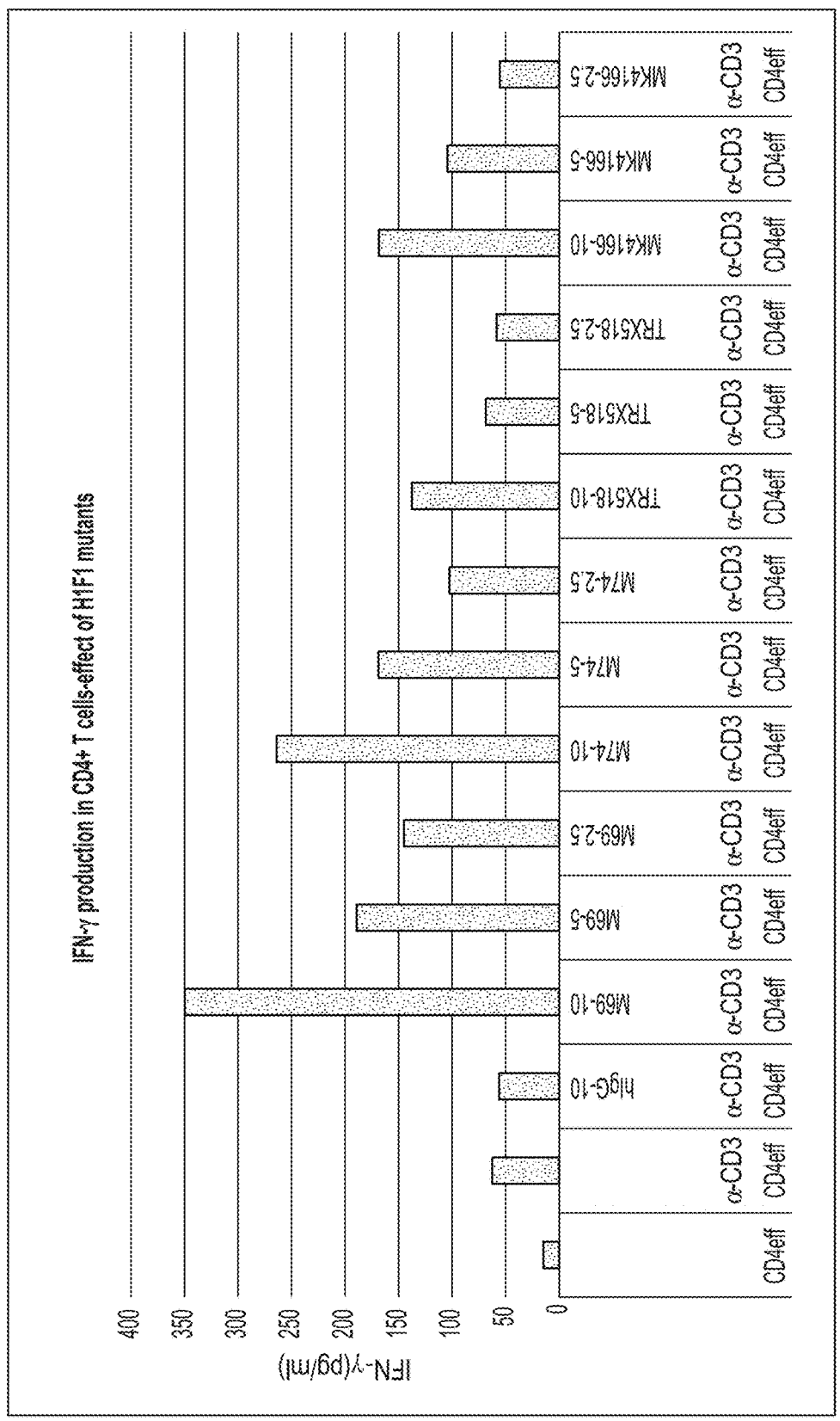
FIG. 26 depicts a graph quantifying the dose-dependent effect of H1F1M69 and H1F1M74 on IFN-γ in $T_{eff}$ cells.

Additionally, the polarized $T_{eff}$ cells were tested for IFN-γ secretion. The graph in FIG. 26 summarizes the results obtained by ELISA assay. H1F1M69 and H1F1M74 stimulated secretion of the $T_H1$ cytokine, IFN-γ, indicating that the $T_{eff}$ cells were polarized to $T_H1$ cells.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the claims.

What is claimed is:

1. An IFN-γ-Inducible Regulatory T Cell Convertible Anti-Cancer (IRTCA) antibody or antigen-binding fragment thereof, comprising:
   (a) a heavy chain CDR1 comprising a sequence of SEQ ID NO: 8 or 24, a heavy chain CDR2 comprising a sequence of SEQ ID NO: 9 or 25, and a heavy chain CDR3 comprising at least one sequence selected from SEQ ID NO: 14, 15, 16, and 17; and
   (b) a light chain CDR1 comprising a sequence of SEQ ID NO: 11, a light chain CDR2 comprising a sequence of SEQ ID NO: 12 and a light chain CDR3 comprising a sequence of SEQ ID NO: 13 or 18,
      wherein the IRTCA antibody or antigen-binding fragment thereof does not comprise each of: (i) a heavy chain CDR1 comprising a sequence of SEQ ID NO: 8; (ii) a heavy chain CDR2 comprising a sequence of SEQ ID NO: 9; (iii) a heavy chain CDR3 comprising a sequence of SEQ ID NO: 10; (iv) a light chain CDR1 comprising a sequence of SEQ ID NO: 11; (v) a light chain CDR2 comprising a sequence of SEQ ID NO: 12; and (vi) a light chain CDR3 comprising a sequence of SEQ ID NO: 13.

2. The IRTCA antibody or antigen-binding fragment of claim 1, wherein the antibody or antigen-binding fragment comprises any one of the following:
   (a) a heavy chain variable domain comprising a sequence at least 90% identical to a sequence selected from SEQ ID NOs: 3, 4, 5, 6, 20, and 21;
   (b) a light chain variable domain comprising a sequence at least 90% identical to a sequence selected from SEQ ID NOs: 7, 22, and 23; or
   (c) a heavy chain variable domain comprising a sequence at least 90% identical to a sequence selected from SEQ ID NOs: 3, 4, 5, 6, 20, and 21 and a light chain variable domain comprising a sequence at least 90% identical to a sequence selected from SEQ ID NOs: 7, 22, and 23.

3. The IRTCA antibody or antigen-binding fragment of claim 1, wherein the antibody or antigen-binding fragment comprises any one of the following:
   (a) a heavy chain variable domain comprising a sequence at least 98% identical to a sequence selected from SEQ ID NOs: 3, 4, 5, 6, 20, and 21;
   (b) a light chain variable domain comprising a sequence at least 98% identical to a sequence selected from SEQ ID NOs: 7, 22, and 23; or
   (c) a heavy chain variable domain comprising a sequence at least 98% identical to a sequence selected from SEQ ID NOs: 3, 4, 5, 6, 20, and 21 and a light chain variable domain comprising a sequence at least 98% identical to a sequence selected from SEQ ID NOs: 7, 22, and 23.

4. The IRTCA antibody or antigen-binding fragment of claim 1, wherein the antibody or antigen-binding fragment comprises any one of the following:
   (a) a heavy chain variable domain comprising a sequence selected from SEQ ID NOs: 3, 4, 5, 6, 20, and 21;
   (b) a light chain variable domain comprising a sequence selected from SEQ ID NOs: 7, 22, and 23; or
   (c) a heavy chain variable domain comprising a sequence selected from SEQ ID NOs: 3, 4, 5, 6, 20, and 21 and a light chain variable domain comprising a sequence selected from SEQ ID NOs: 7, 22, and 23.

5. The IRTCA antibody or antigen-binding fragment of claim 1, wherein the antibody or antigen-binding fragment has a binding affinity ($K_D$) for a human Activation-Inducible Tumor Necrosis Factor Receptor (AITR) molecule of $1 \times 10^{-7}$ to $1 \times 10^{-12}$ M.

6. The IRTCA antibody or antigen-binding fragment of claim 1, wherein the antibody or antigen-binding fragment binds to an epitope within the extracellular domain of human AITR polypeptide.

7. The IRTCA antibody or antigen-binding fragment of claim 6, wherein epitope within the extracellular domain of human AITR polypeptide comprises SEQ ID NO: 19.

8. The IRTCA antibody or antigen-binding fragment of claim 1, wherein the antibody includes an immunoglobulin constant domain, wherein the constant domain is selected from an IgG1 or a variant thereof, an IgG2 or a variant thereof, an IgG4 or a variant thereof, an IgA or a variant thereof, an IgE or a variant thereof, an IgM or a variant thereof, and an IgD or a variant thereof.

9. The IRTCA antibody or antigen-binding fragment of claim 1, wherein the antibody is or comprises a human IgG1.

10. The IRTCA antibody or antigen-binding fragment of claim 9, wherein the IgG1 is or comprises a sequence that is at least 95% identical to SEQ ID NO: 26.

11. The IRTCA antibody or antigen-binding fragment of claim 1, wherein the antibody or antigen-binding fragment is a monoclonal antibody.

12. The IRTCA antibody or antigen-binding fragment of claim 1, wherein the antibody fragment is a Fab fragment, a Fab' fragment, a F(ab')2 fragment, a Fv fragment, a disulfide-bonded Fv fragment, a scFv fragment, a single domain antibody, humabody, nanobody, or a diabody.

13. A nucleic acid molecule encoding an IRTCA antibody or antigen-binding fragment of claim 1.

14. A recombinant vector comprising the nucleic acid molecule of claim 13.

15. A host cell comprising the nucleic acid molecule of claim 13.

16. The host cell of claim 15, wherein the host cell is selected from a bacterial, yeast, insect or mammalian cell.

17. The host cell of claim 16, wherein the host cell is selected from the group consisting of E. coli, P. pastoris, Sf9, COS, HEK293, Expi293, CHO-S, CHO-DG44, CHO-K1, and a mammalian lymphocyte.

18. A pharmaceutical composition comprising:
   (a) the IRTCA antibody or antigen-binding fragment of claim 1; and
   (b) a pharmaceutically acceptable carrier.

19. A method of treating a subject in need thereof, the method comprising the steps of:
   administering to the subject a composition that comprises or delivers the IRTCA antibody or antigen-binding fragment of claim 1, wherein the IRTCA antibody or antigen-binding fragment comprises (a) a heavy chain CDR1 comprising a sequence of SEQ ID NO: 8, a heavy chain CDR2 comprising a sequence of SEQ ID NO: 9, and a heavy chain CDR3 comprising a sequence of SEQ ID NO: 16; and (b) a light chain CDR1 comprising a sequence of SEQ ID NO: 11, a light chain CDR2 comprising a sequence of SEQ ID NO: 12 and a light chain CDR3 comprising a sequence of SEQ ID NO: 13.

20. A method of inducing an immune response in a subject in need thereof, the method comprising the steps of:
   administering to the subject a composition that comprises or delivers the IRTCA antibody or antigen-binding fragment of claim 1.

21. A method of enhancing an immune response or increasing the activity of an immune cell in a subject in need thereof, the method comprising the steps of: administering to the subject a composition that comprises or delivers the IRTCA antibody or antigen-binding fragment of claim 1.

22. The method of claim 19, wherein the subject has, or is at risk for developing, cancer.

23. The method of claim 22, wherein the cancer is selected from a colon cancer, melanoma, breast cancer and gastric cancer.

24. The method of claim 19, wherein the subject has been administered or will be administered one or more additional anticancer therapies selected from ionizing radiation, a chemotherapeutic agent, an antibody agent, and a cell-based therapy, such that the subject receives treatment with both.

25. The method of claim 24, wherein the one or more additional anticancer therapies comprise an immune checkpoint inhibitor, IL-12, GM-CSF, an anti-CD4 agent, cisplatin, fluorouracil, doxorubicin, irinotecan, paclitaxel, indoleamine 2,3-dioxygenase-1 (IDO1) inhibitor, or cyclophosphamide.

26. A method for increasing secretion of IFN-γ by a T cell and/or decreasing secretion of TGF-β by a T cell in vivo or in vitro, the method comprising: contacting the cell with the IRTCA antibody or antigen-binding fragment of claim 1.

27. A method of converting a T cell into a Type 1 helper T ($T_H1$) cell, the method comprising: contacting the cell with the IRTCA antibody or antigen-binding fragment of claim 1.

28. The method of claim 26, wherein the T cell expresses AITR protein.

29. The method of claim 26, wherein the T cell is a regulatory T cell ($T_{reg}$ cell) or an effector T cell ($T_{eff}$ cell).

30. The IRTCA antibody or antigen-binding fragment of claim 1, comprising:
  (a) a heavy chain CDR1 comprising a sequence of SEQ ID NO: 24, a heavy chain CDR2 comprising a sequence of SEQ ID NO: 25, and a heavy chain CDR3 comprising a sequence of SEQ ID NO: 16; a light chain CDR1 comprising a sequence of SEQ ID NO: 11, a light chain CDR2 comprising a sequence of SEQ ID NO: 12 and a light chain CDR3 comprising a sequence of SEQ ID NO: 13; or
  (b) a heavy chain CDR1 comprising a sequence of SEQ ID NO: 8, a heavy chain CDR2 comprising a sequence of SEQ ID NO: 25, and a heavy chain CDR3 comprising a sequence of SEQ ID NO: 16; a light chain CDR1 comprising a sequence of SEQ ID NO: 11, a light chain CDR2 comprising a sequence of SEQ ID NO: 12 and a light chain CDR3 comprising a sequence of SEQ ID NO: 18.

* * * * *